(12) United States Patent
Boddington et al.

(10) Patent No.: US 11,937,888 B2
(45) Date of Patent: *Mar. 26, 2024

(54) ARTIFICIAL INTELLIGENCE INTRA-OPERATIVE SURGICAL GUIDANCE SYSTEM

(71) Applicant: Orthogrid Systems Inc., Salt Lake City, UT (US)

(72) Inventors: Richard Boddington, Salt Lake City, UT (US); Edouard Saget, Boise, ID (US); Joshua Cates, Salt Lake City, UT (US); Hind Oulhaj, Strasbourg (FR); Erik Noble Kubiak, Las Vegas, NV (US)

(73) Assignee: Orthogrid Systems Holding, LLC, Midvale, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/099,601

(22) Filed: Jan. 20, 2023

(65) Prior Publication Data

US 2023/0157765 A1 May 25, 2023

Related U.S. Application Data

(63) Continuation of application No. 16/916,876, filed as application No. PCT/US2019/050745 on Sep. 12, 2019, now Pat. No. 11,589,928.

(Continued)

(51) Int. Cl.
*A61B 34/20* (2016.01)
*A61B 17/17* (2006.01)
(Continued)

(52) U.S. Cl.
CPC .......... *A61B 34/20* (2016.02); *A61B 17/1703* (2013.01); *A61B 17/1721* (2013.01);
(Continued)

(58) Field of Classification Search
CPC .......... A61B 6/463; A61B 6/12; A61B 6/487; A61B 6/505; A61B 2090/061;
(Continued)

(56) References Cited

U.S. PATENT DOCUMENTS

| 5,052,035 A | 9/1991 | Krupnick |
| 6,078,699 A | 6/2000 | Lobregt et al. |

(Continued)

FOREIGN PATENT DOCUMENTS

| WO | 2017083768 A1 | 5/2017 |
| WO | 2017219149 A1 | 12/2017 |

(Continued)

OTHER PUBLICATIONS

Lin et al. Three-dimensional computer-assisted surgical simulation and inoperative navigation in Orthognathic Surgery: A Literature Review. In J of the Formosan Med. Asso. (2015).

(Continued)

*Primary Examiner* — Solomon G Bezuayehu
(74) *Attorney, Agent, or Firm* — Veritay Group IP PLLC; Susan Fentres

(57) ABSTRACT

The inventive subject matter is directed to an artificial intelligence intra-operative surgical guidance system and method of use. The artificial intelligence intra-operative surgical guidance system is made of a computer executing one or more automated artificial intelligence models trained on data layer datasets collections to calculate surgical decision risks, and provide intra-operative surgical guidance; and a display configured to provide visual guidance to a user.

13 Claims, 57 Drawing Sheets
(3 of 57 Drawing Sheet(s) Filed in Color)

Related U.S. Application Data

(60) Provisional application No. 62/730,112, filed on Sep. 12, 2018.

(51) Int. Cl.

| | | |
|---|---|---|
| *A61B 34/00* | (2016.01) | |
| *A61B 34/10* | (2016.01) | |
| *A61B 34/30* | (2016.01) | |
| *G06N 3/08* | (2023.01) | |
| *G06N 20/00* | (2019.01) | |
| *G06V 10/426* | (2022.01) | |
| *G16H 20/40* | (2018.01) | |
| *G16H 30/40* | (2018.01) | |
| *G16H 50/20* | (2018.01) | |
| *G16H 50/70* | (2018.01) | |
| *G16H 70/20* | (2018.01) | |
| *A61B 90/00* | (2016.01) | |

(52) U.S. Cl.
CPC ............ *A61B 34/10* (2016.02); *A61B 34/30* (2016.02); *A61B 34/76* (2016.02); *G06N 3/08* (2013.01); *G06N 20/00* (2019.01); *G06V 10/426* (2022.01); *G16H 20/40* (2018.01); *G16H 30/40* (2018.01); *G16H 50/20* (2018.01); *G16H 50/70* (2018.01); *G16H 70/20* (2018.01); *A61B 2034/104* (2016.02); *A61B 2034/107* (2016.02); *A61B 2034/2065* (2016.02); *A61B 34/25* (2016.02); *A61B 2034/252* (2016.02); *A61B 2090/365* (2016.02); *A61B 2090/376* (2016.02)

(58) Field of Classification Search
CPC ...... A61B 2090/365; A61B 2090/3966; A61B 2090/502; A61B 90/37; A61B 34/25; A61B 2017/00203; A61B 2017/00207; A61B 2017/00216; A61B 2017/00725; A61B 2034/105; A61B 2034/107; A61B 2090/372; A61B 2090/376; A61B 2576/00; A61B 6/5211; A61B 34/20; A61B 17/1703; A61B 17/1721; A61B 34/10; A61B 34/30; G06T 7/30; G06T 7/60; G06T 11/00; G06T 2200/24; G06T 2207/10064; G06T 2207/10116; G06T 19/00; G06T 2210/41; G06T 2219/004; G06T 2219/012; G06V 10/764; G06V 10/82; G06V 2201/033; G06V 2201/034; G06N 3/045; G06N 3/08
See application file for complete search history.

(56) References Cited

U.S. PATENT DOCUMENTS

| | | | |
|---|---|---|---|
| 6,097,833 A | 8/2000 | Lobregt et al. | |
| 6,269,177 B1 | 7/2001 | Dewaele et al. | |
| 6,438,401 B1 | 8/2002 | Cheng et al. | |
| 6,711,432 B1 | 3/2004 | Krause et al. | |
| 7,130,676 B2 * | 10/2006 | Barrick ................ A61B 90/36 | 606/130 |
| 7,394,946 B2 | 7/2008 | Dewaele | |
| 7,493,153 B2 | 2/2009 | Ahmed et al. | |
| 7,664,289 B2 | 2/2010 | Worthington et al. | |
| 7,664,298 B2 | 2/2010 | Lang et al. | |
| 7,764,293 B2 | 7/2010 | Kakuta et al. | |
| 7,852,355 B2 | 12/2010 | Friedrich et al. | |
| 7,935,048 B2 | 5/2011 | Yaron et al. | |
| 8,194,936 B2 | 6/2012 | Abramoff et al. | |
| 8,300,764 B2 | 10/2012 | Yamaguchi | |
| 8,484,001 B2 | 7/2013 | Glozman et al. | |
| 8,532,352 B2 | 9/2013 | Ionasec et al. | |
| 8,554,697 B2 | 10/2013 | Claus et al. | |
| 8,611,697 B2 | 12/2013 | Nathaniel et al. | |
| 8,698,843 B2 | 4/2014 | Tseng | |
| 8,810,599 B1 | 8/2014 | Tseng | |
| 8,831,324 B2 | 9/2014 | Penenberg | |
| 8,855,389 B1 | 10/2014 | Hoffmann et al. | |
| 8,890,896 B1 | 11/2014 | Tseng | |
| 8,948,487 B2 | 2/2015 | Sundar | |
| 9,042,621 B2 | 5/2015 | Ashby et al. | |
| 9,064,332 B2 | 6/2015 | Valadez et al. | |
| 9,109,998 B2 | 8/2015 | Nathaniel et al. | |
| 9,111,180 B2 | 8/2015 | Rappaport et al. | |
| 9,153,195 B2 | 10/2015 | Geisner et al. | |
| 9,213,405 B2 | 12/2015 | Perez et al. | |
| 9,277,970 B2 | 3/2016 | Mansi et al. | |
| 9,430,496 B2 | 8/2016 | Tseng | |
| 9,433,390 B2 | 9/2016 | Nathaniel et al. | |
| 9,437,036 B2 | 9/2016 | Yoo et al. | |
| 9,456,874 B2 | 10/2016 | Kubiak et al. | |
| 9,529,424 B2 | 12/2016 | Hilliges et al. | |
| 9,538,962 B1 | 1/2017 | Hannaford et al. | |
| 9,560,291 B2 | 1/2017 | Weiser et al. | |
| 9,610,134 B2 | 4/2017 | Kubiak et al. | |
| 9,737,369 B2 | 8/2017 | Burger et al. | |
| 9,754,371 B2 | 9/2017 | Kateb et al. | |
| 9,788,907 B1 * | 10/2017 | Alvi ...................... | G11B 27/34 |
| 9,861,446 B2 | 1/2018 | Lang | |
| 9,980,780 B2 | 5/2018 | Lang | |
| 10,092,164 B2 | 10/2018 | Sholev et al. | |
| 10,092,362 B2 | 10/2018 | Wasielewski | |
| 10,201,320 B2 | 2/2019 | Saget et al. | |
| 10,338,931 B2 | 7/2019 | Gupta et al. | |
| 10,339,695 B2 | 7/2019 | Petkov et al. | |
| 10,433,914 B2 | 10/2019 | Wollowick et al. | |
| 10,512,451 B2 | 12/2019 | Mahfouz | |
| 10,748,319 B1 | 8/2020 | Tao et al. | |
| 2001/0047132 A1 | 11/2001 | Johnson et al. | |
| 2004/0039259 A1 | 2/2004 | Krause et al. | |
| 2004/0044295 A1 | 3/2004 | Reinert et al. | |
| 2004/0068187 A1 | 4/2004 | Krause et al. | |
| 2004/0087852 A1 | 5/2004 | Chen et al. | |
| 2005/0113846 A1 | 5/2005 | Carson | |
| 2006/0111631 A1 | 5/2006 | Kelliher et al. | |
| 2006/0142739 A1 | 6/2006 | DiSilestro et al. | |
| 2007/0073136 A1 | 3/2007 | Metzger | |
| 2007/0233267 A1 | 10/2007 | Amirouche et al. | |
| 2007/0249967 A1 | 10/2007 | Buly et al. | |
| 2008/0123910 A1 | 5/2008 | Zhu | |
| 2008/0200926 A1 | 8/2008 | Verard et al. | |
| 2008/0319448 A1 | 12/2008 | Lavallee et al. | |
| 2009/0017430 A1 | 1/2009 | Muller-Daniels et al. | |
| 2009/0046906 A1 | 2/2009 | Wohlgemuth et al. | |
| 2009/0093702 A1 | 4/2009 | Vollmer et al. | |
| 2009/0099862 A1 | 4/2009 | Fireman et al. | |
| 2009/0177205 A1 | 7/2009 | McCormack et al. | |
| 2009/0259230 A1 | 10/2009 | Khadem et al. | |
| 2009/0274350 A1 | 11/2009 | Pavlovskaia et al. | |
| 2010/0130871 A1 | 5/2010 | Frykman et al. | |
| 2011/0152676 A1 | 6/2011 | Groszmann et al. | |
| 2011/0160546 A1 | 6/2011 | Madsen | |
| 2011/0295378 A1 | 12/2011 | Bojarski et al. | |
| 2012/0071752 A1 | 3/2012 | Sewell et al. | |
| 2012/0123422 A1 | 5/2012 | Agnihotri et al. | |
| 2013/0113802 A1 | 5/2013 | Weersink et al. | |
| 2013/0118736 A1 | 5/2013 | Usadi et al. | |
| 2013/0211232 A1 | 8/2013 | Murphy et al. | |
| 2013/0211531 A1 | 8/2013 | Steines et al. | |
| 2014/0086394 A1 | 3/2014 | Batkilin et al. | |
| 2014/0093154 A1 | 4/2014 | Penenberg | |
| 2014/0133727 A1 * | 5/2014 | Oktay ..................... | G06T 7/33 |
| | | | 382/131 |
| 2015/0086955 A1 | 3/2015 | Poniatowski et al. | |
| 2015/0088146 A1 | 3/2015 | McCarthy | |
| 2015/0150460 A1 | 6/2015 | Krishnaswamy et al. | |
| 2015/0160322 A1 | 6/2015 | Matthews | |
| 2015/0238271 A1 | 8/2015 | Wollowick et al. | |
| 2015/0257846 A1 | 9/2015 | Kubiak et al. | |
| 2015/0272695 A1 | 10/2015 | Kubiak et al. | |
| 2015/0366628 A1 | 12/2015 | Ingmanson | |

(56) References Cited

U.S. PATENT DOCUMENTS

| | | | |
|---|---|---|---|
| 2016/0005236 A1 | 1/2016 | Lachmanovich et al. | |
| 2016/0038252 A1 | 2/2016 | Barth, Jr. et al. | |
| 2016/0166336 A1 | 6/2016 | Razzaque et al. | |
| 2016/0191887 A1* | 6/2016 | Casas | H04N 13/279 348/47 |
| 2017/0071673 A1 | 3/2017 | Ferro et al. | |
| 2017/0105601 A1 | 4/2017 | Pheiffer et al. | |
| 2017/0105802 A1 | 4/2017 | Taraschi et al. | |
| 2017/0185727 A1* | 6/2017 | Harris | G06N 5/04 |
| 2017/0312032 A1* | 11/2017 | Amanatullah | G09B 23/30 |
| 2017/0340418 A1* | 11/2017 | Raanan | G06V 30/142 |
| 2018/0000339 A1 | 1/2018 | Hipsley | |
| 2018/0114087 A1 | 4/2018 | Kamen et al. | |
| 2018/0233222 A1 | 8/2018 | Daley et al. | |
| 2018/0247128 A1* | 8/2018 | Alvi | H04L 67/12 |
| 2018/0263700 A1 | 9/2018 | Gillman et al. | |
| 2018/0303552 A1 | 10/2018 | Ryan et al. | |
| 2018/0360543 A1 | 12/2018 | Roh et al. | |
| 2018/0366231 A1* | 12/2018 | Wolf | G16H 20/40 |
| 2018/0368930 A1 | 12/2018 | Esterberg et al. | |
| 2019/0000564 A1 | 1/2019 | Navab et al. | |
| 2019/0000570 A1 | 1/2019 | Esterberg et al. | |
| 2019/0013099 A1 | 1/2019 | Esterberg et al. | |
| 2019/0021795 A1 | 1/2019 | Crawford et al. | |
| 2019/0034591 A1 | 1/2019 | Mossin et al. | |
| 2019/0070005 A1 | 3/2019 | Brailovski et al. | |
| 2019/0088360 A1 | 3/2019 | Goble et al. | |
| 2019/0122330 A1 | 4/2019 | Saget et al. | |
| 2019/0142520 A1* | 5/2019 | VanDyken | G09B 23/30 606/1 |
| 2019/0147128 A1* | 5/2019 | O'Connor | G16H 30/20 703/11 |
| 2019/0180466 A1 | 6/2019 | Tao | |
| 2019/0231433 A1* | 8/2019 | Amanatullah | A61B 17/1703 |
| 2019/0236394 A1 | 8/2019 | Price et al. | |
| 2019/0239973 A9 | 8/2019 | Esterberg et al. | |
| 2019/0262084 A1* | 8/2019 | Roh | G16H 20/40 |
| 2019/0286885 A1* | 9/2019 | Liu | G06V 10/145 |
| 2019/0290363 A1 | 9/2019 | Blau et al. | |
| 2020/0027561 A1 | 1/2020 | Rao | |
| 2020/0100751 A1 | 4/2020 | Wollowick et al. | |
| 2020/0168338 A1* | 5/2020 | Forsberg | G16H 40/63 |
| 2020/0237432 A1 | 7/2020 | Sims et al. | |
| 2020/0237452 A1 | 7/2020 | Wolf et al. | |
| 2020/0272864 A1* | 8/2020 | Faust | G06V 10/764 |
| 2020/0352529 A1 | 11/2020 | Wollowick et al. | |
| 2020/0405397 A1* | 12/2020 | Liu | A61B 34/10 |
| 2021/0169576 A1* | 6/2021 | Yoshinaka | G06N 20/00 |
| 2021/0174938 A1 | 6/2021 | Park et al. | |
| 2021/0264601 A1* | 8/2021 | Pasha | G06V 10/454 |
| 2021/0307841 A1* | 10/2021 | Buch | A61B 5/749 |

FOREIGN PATENT DOCUMENTS

| | | |
|---|---|---|
| WO | 2018131044 A1 | 7/2018 |
| WO | 2018144872 A1 | 8/2018 |

OTHER PUBLICATIONS

PCT/US2017/040173 Written Opinion dated Oct. 31, 2017.
PCT/US2019/050745 International Preliminary Report on Patenability.
PCT/US2019/050745 PCT International Search Report dated Dec. 15, 2019.

* cited by examiner

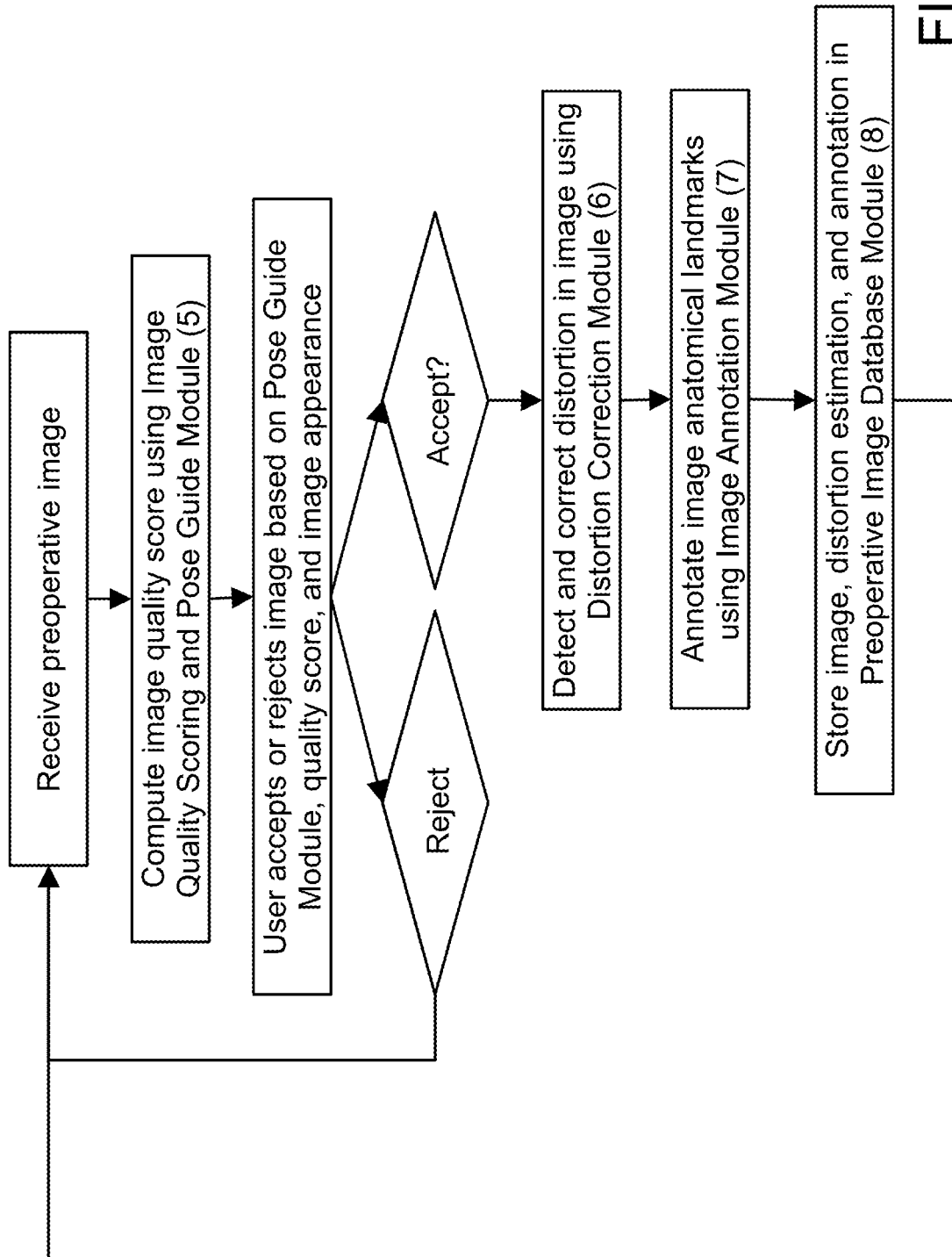

Log-screw cutout predictive analytic algorithm and lag screw placement guidance for optimal and sub-optimal outcome.

ARTIFICIAL INTELLIGENCE INTRA-OPERATIVE SURGICAL GUIDANCE SYSTEM

CROSS REFERENCE TO RELATED APPLICATIONS

This application claims the benefit of benefit of US patent application 16,916,876 filed Jun. 30, 2020, PCT/US2019/050745 filed Sep. 12, 2019, under 35 USC Sec. 371 and US provisional patent application no. 62,730,112 filed Sep. 12, 2018, under 35 U.S.C. Sec. 119(e) (hereby incorporated by reference in their entirety).

FIELD OF THE INVENTION

The subject of this invention is an artificial intelligence intraoperative surgical guidance in joint replacements, spine, trauma fracture reductions and deformity correction and implant placement/alignment. A method is provided for analyzing subject image data, calculating surgical decision risks and autonomously providing recommended pathways or actions that support the decision-making process of a surgeon to predict optimized implant and subject outcomes (ex. implant guidance, fracture reduction, anatomical alignment) by a graphical user interface.

BACKGROUND OF THE INVENTION

Many of the radiographic parameters essential to total hip arthroplasty (THA) model performance, such as wear and stability, can be assessed intraoperatively with fluoroscopy. However even with intraoperative fluoroscopic guidance, the placement of an implant or the reduction of a bone fragment can still not be as close as desired by the surgeon. For example, mal-positioning of the acetabular model during hip arthroplasty can lead to problems. For the acetabular implant to be inserted in the proper position relative to the pelvis during hip arthroplasty requires that the surgeon know the position of the patient's pelvis during surgery. Unfortunately, the position of the patient's pelvis varies widely during surgery and from patient to patient. During trauma surgery, proper fracture management, especially in the case of an intra-articular fracture, requires a surgeon to reduce the bone fragment optimally with respect to the original anatomy in order to: provide the anatomical with joint the best chance to rehabilitate properly; minimize further long-term damage; and, if possible, to regain its normal function. Unfortunately, in a fracture scenario, the original anatomical position of these bone fragments has been compromised and their natural relationship with the correct anatomy is uncertain and requires the surgeon to use his/her best judgment in order to promote a successful repair and subsequent positive outcome. During a surgery, a surgeon is required to make real-time decisions that can be further complicated by the fact that there are multiple decisions needing to be made at the same time. At any given time, there can be a need for a decision made on a fracture reduction guidance for example and simultaneously a decision required on implant placement and an error at any stage will likely increase the potential for a sub-optimal outcome and potential surgical failure. Unfortunately, most of these problems are only diagnosed and detected postoperatively and oftentimes lead to revision surgery. These risks and patterns need to be identified in real-time during the surgical or medical event. As surgeons and medical professionals must often rely solely on themselves to identify hazards and risks or make decisions on critical factors in, and surrounding, a surgical event, a need exists for a system and method that can provide intraoperative automated intelligence guided surgical and medical situational awareness support and guidance.

SUMMARY OF THE INVENTION

This summary describes several embodiments of the presently disclosed subject matter and, in many cases, lists variations and permutations of these embodiments. This summary is merely exemplary of the numerous and varied embodiments. Mention of one or more representative features of a given embodiment is likewise exemplary. Such an embodiment can typically exist with or without the feature (s) mentioned; likewise, those features can be applied to other embodiments of the presently disclosed subject matter, whether listed in this summary or not. To avoid excessive repetition, this summary does not list or suggest all possible combinations of such features.

The novel subject matter includes an artificial intelligence intra-operative surgical guidance system made of: a computing platform configured to execute one or more automated artificial intelligence models, wherein the one or more automated artificial intelligence models are trained on data from a data layer, wherein the data layer includes at least surgical images, to calculate intra-operative surgical decision risks, and to provide an intra-operative surgical guidance to a user. More specifically, the computing platform is configured to provide an intra-operative visual display to the user showing surgical guidance. The computing platform is trained to show intra-operative surgical decision risks by applying an at least one classification algorithm.

The novel subject matter further includes method for generating a dynamic guidance indicator for use in a surgical procedure. The method includes the steps of: receiving an intra-operative image of a subject; generating a grid data predictive map; wherein the grid data predictive map is generated by an artificial intelligence engine; and aligning the intra-operative image with the grid data predictive map to generate a dynamic guidance indicator. In one exemplary embodiment, the dynamic guidance indicator is made of a first color for sub-optimal positioning and second color for optimal positioning of an implant or bone alignment.

The novel subject matter further includes a computer-implemented method for providing surgical guidance. The method steps include obtaining subject image data made of: a preoperative image of a nonoperative side of a subject's anatomy and an intraoperative image of an operative side of the subject's anatomy; dynamically displaying the subject image data on a graphical user interface; selecting an anatomical structure within the subject image data and mapping a grid template to the anatomical structure to register an image for the nonoperative side of the subject's anatomy with an image of the intraoperative image of the operative side of the subject's anatomy to provide a registered composite image; providing a computing platform is made of: an artificial intelligence engine and at least one dataset configured to generate a surgical guidance; providing as a data output, the registered composite image to the artificial intelligence engine to generate an at least one surgical guidance; and dynamically updating, by the computing platform, the registered composite image with the at least one surgical guidance. The surgical guidance can include robotic synchronization, a cutting block, an Internet of Things (IoT) device, and a trackable guide.

The novel subject matter includes: a computer-implemented method for artificial intelligence based surgical guidance. The novel method includes the steps of: providing a computing platform made of a non-transitory computer-readable storage medium coupled to a microprocessor, wherein the non-transitory computer-readable storage medium is encoded with computer-readable instructions that implement functionalities of a plurality of modules, wherein the computer-readable instructions are executed by a microprocessor. The novel method includes the steps of: receiving an at least one preoperative image of a subject; computing an image quality score using an Image Quality Scoring Module; accepting or rejecting the preoperative image based on quality score generated by a Pose Guide Module, if the at least one preoperative image is accepted; correcting for distortion in the at least one preoperative image; annotating an at least one anatomical landmark in the preoperative image using an Image Annotation Module to provide an at least one annotated preoperative image; storing the at least one annotated preoperative image in a preoperative image database; receiving an at least one intraoperative image; computing image quality score using an Image Quality Scoring Module; accepting or rejecting the at least one intraoperative image based on quality score generated by a Pose Guide Module, if the at least one intraoperative image is accepted; correcting for distortion in the at least one intraoperative image; annotating an at least one anatomical landmark using an Image Annotation Module to provide an at least one annotated intraoperative image; registering the at least one annotated intraoperative image to a best matching image in the preoperative image database; computing a matching score using an image registration; if accepted; estimating a three-dimensional shape of an implant or anatomy using a 3D Shape Modeling Module; mapping an alignment grid to the annotated image features using an Image Registration Module to form a composite image and displaying the composite image on a graphical user interface; and dynamically updating, by the computing platform, the composite image to provide an at least one surgical guidance.

More specifically, the method further includes the steps of: receiving an at least one postoperative image of the subject by the computing platform; computing an image quality score of the at least one postoperative image using an Image Quality Scoring Module; accepting or rejecting the at least one postoperative image based on quality score generated by a Pose Guide Module, if image is accepted; correcting for distortion in the at least one post-operative image; annotating an at least one image anatomical landmark using an image annotation module to provide an at least one postoperative annotated image; registering the at least one postoperative annotated image to a prior image in a postoperative image database and computing matching scores; computing a matching score using an image registration metric; if accepted; estimating a three-dimensional shape of an implant or an anatomy using a 3D Shape Modeling Module; mapping an alignment grid to an annotated image features using the Image Registration Module; displaying a composite image on the graphical user interface; computing outcome probability score using the Postoperative Outcomes Prediction Model; and displaying the composite image on the graphical user interface; and dynamically updating, by the computing platform, the composite image with an outcome prediction guidance.

The inventive subject matter further includes a method to provide an orthopedic surgeon conducting an alignment or fixation procedure with a visual display configured to provide intra-operative surgical guidance to the orthopedic surgeon. This method includes the steps of providing a computing platform, wherein the computing platform is further comprised of: a plurality of datasets and at least one outcomes prediction module comprised of multiple trained classifiers each with a weighted contribution to a surgical outcome prediction for an alignment or fixation procedure and providing a visual display configured to provide the intra-operative surgical guidance to a the orthopedic surgeon conducting an alignment or fixation procedure.

BRIEF DESCRIPTION OF THE SEVERAL IMAGES OF THE DRAWINGS

The patent or application file contains at least one drawing executed in color. Copies of this patent or patent application publication with color drawing(s) will be provided by the Office upon request and payment of the necessary fee. The drawings show schematically a fluoroscopic alignment plate apparatus and method of use according to an example form of the present invention. The invention description refers to the accompanying drawings.

Figure 3A:
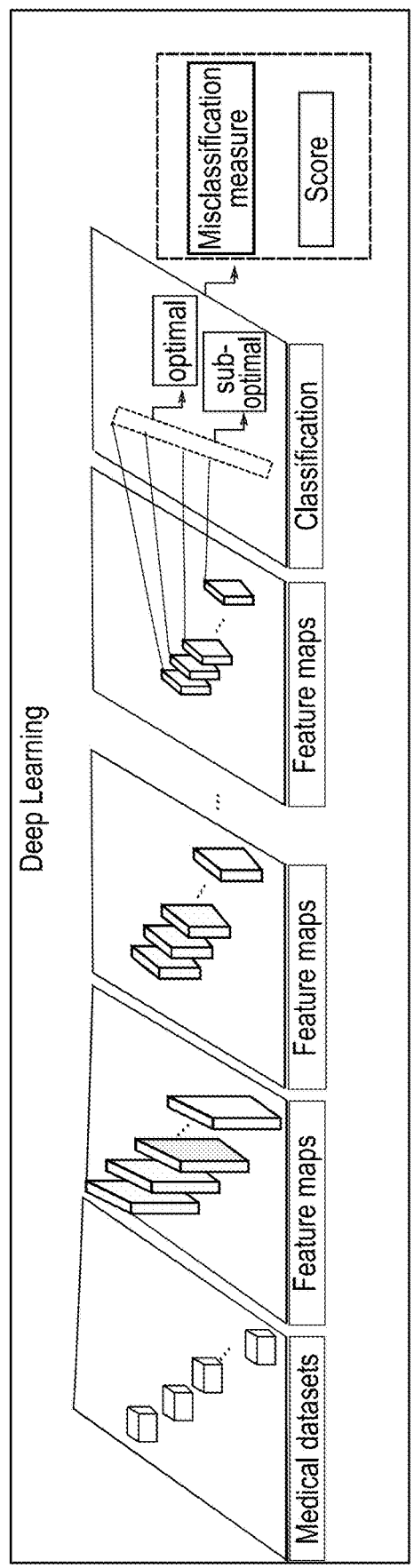

FIG. 3A. is a schematic illustration of Deep Learning as applied to automated intraoperative surgical guidance.

Figure 3B:
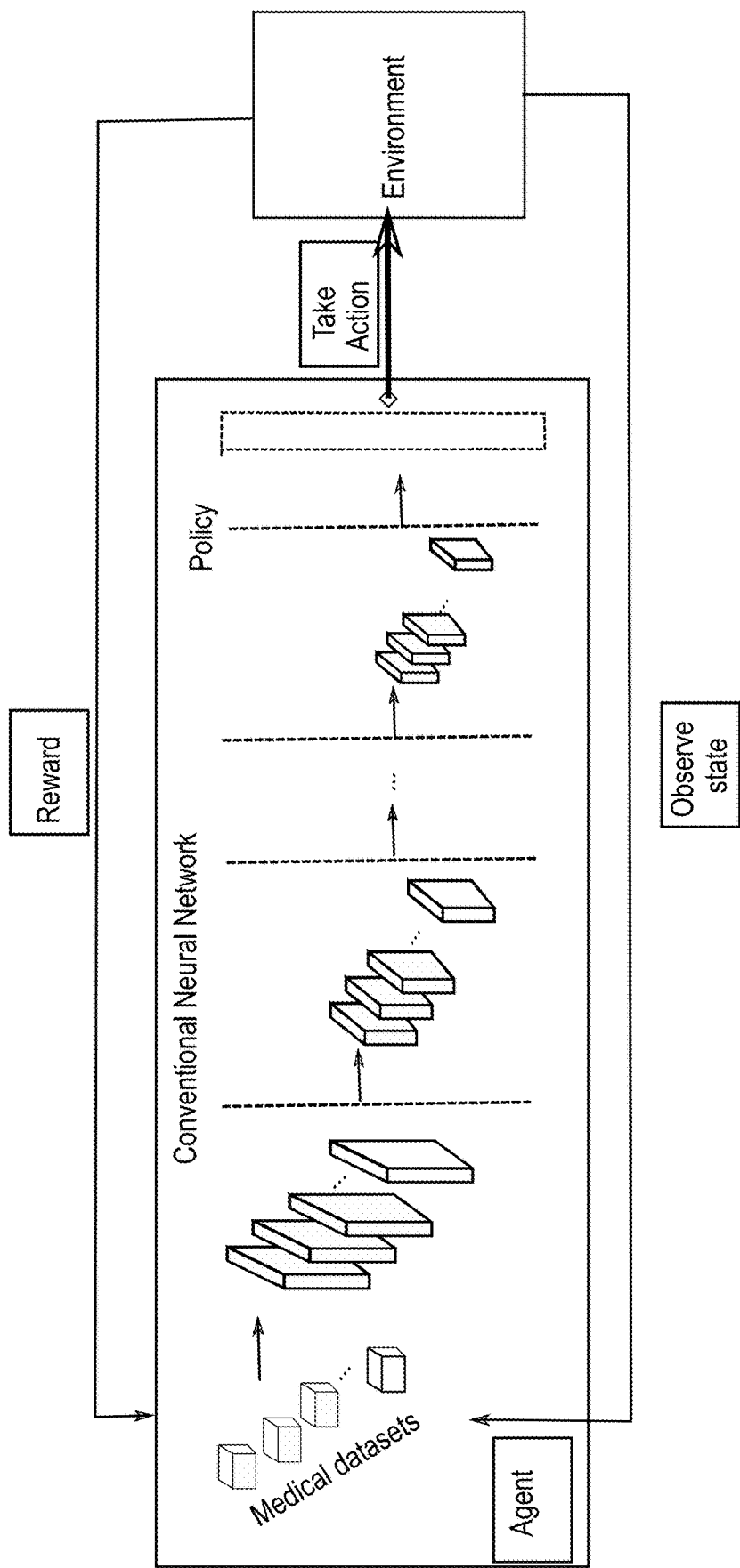

FIG. 3B is a schematic illustration of reinforcement learning automated intraoperative surgical guidance.

Figure 4A:
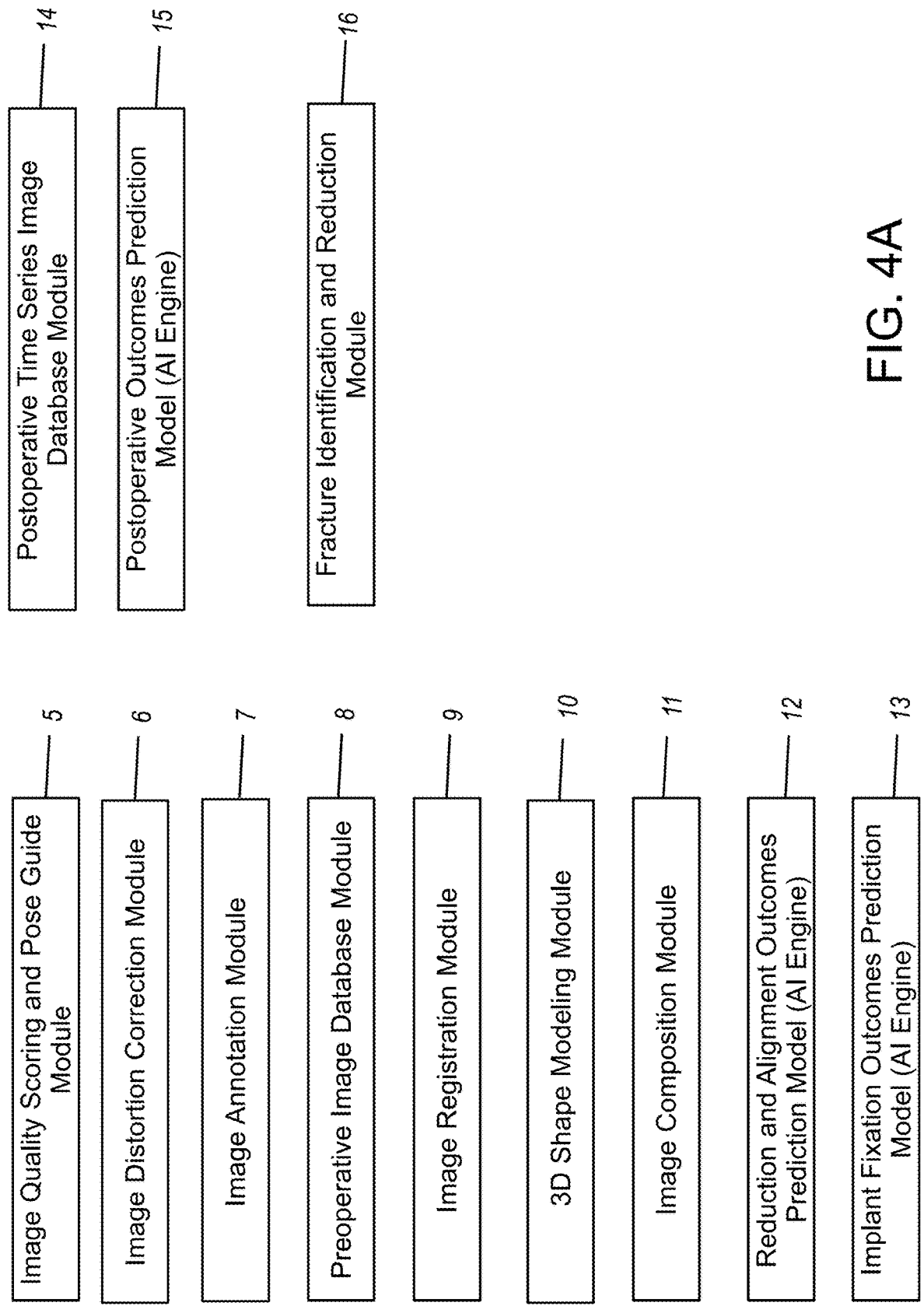

FIG. 4A is a block diagram of the software modules.

Figure 4B:
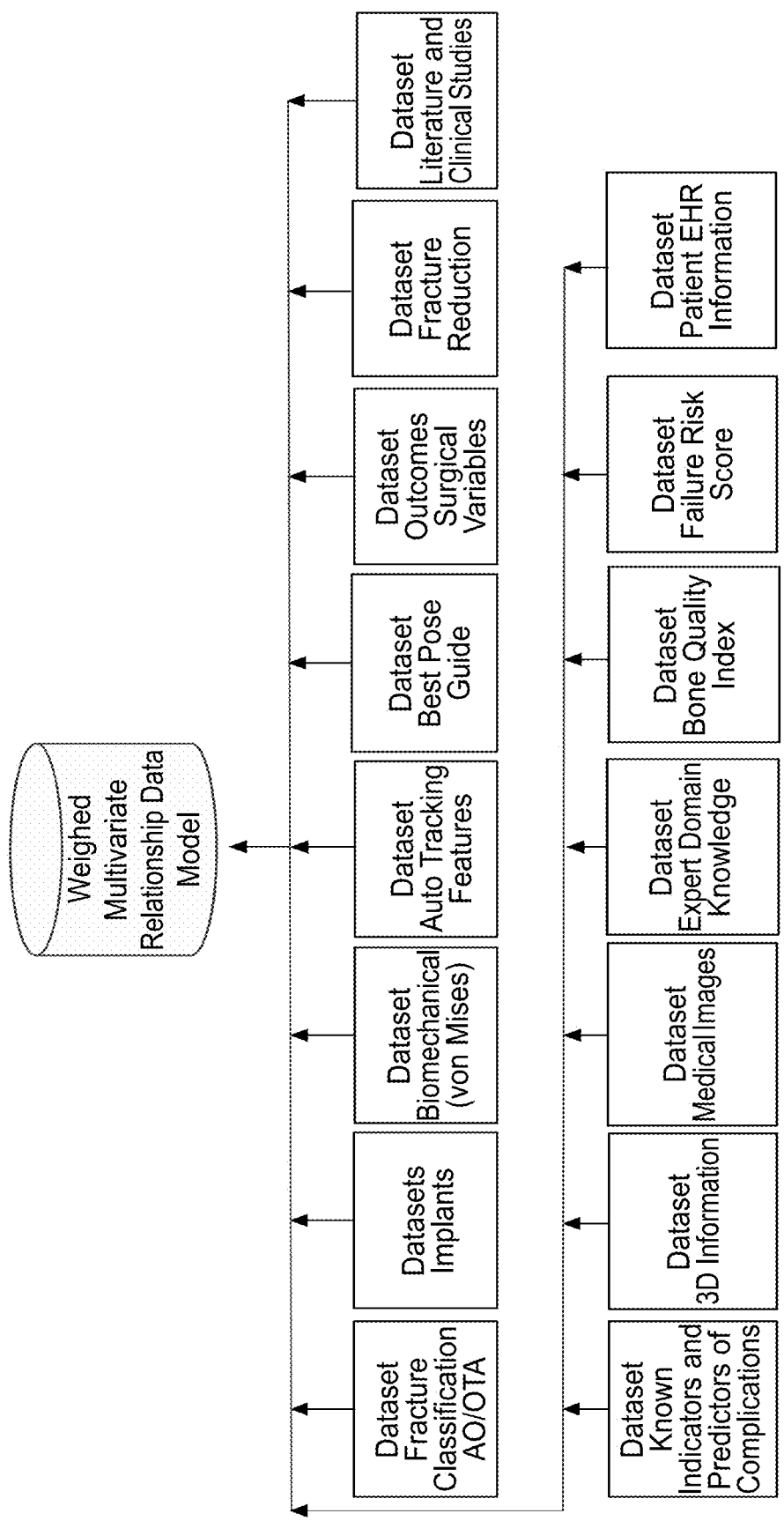

FIG. 4B is a data-set flow-chart.

FIG. 5A is an overview of preoperative workflow of the present invention.

Figure 5B:
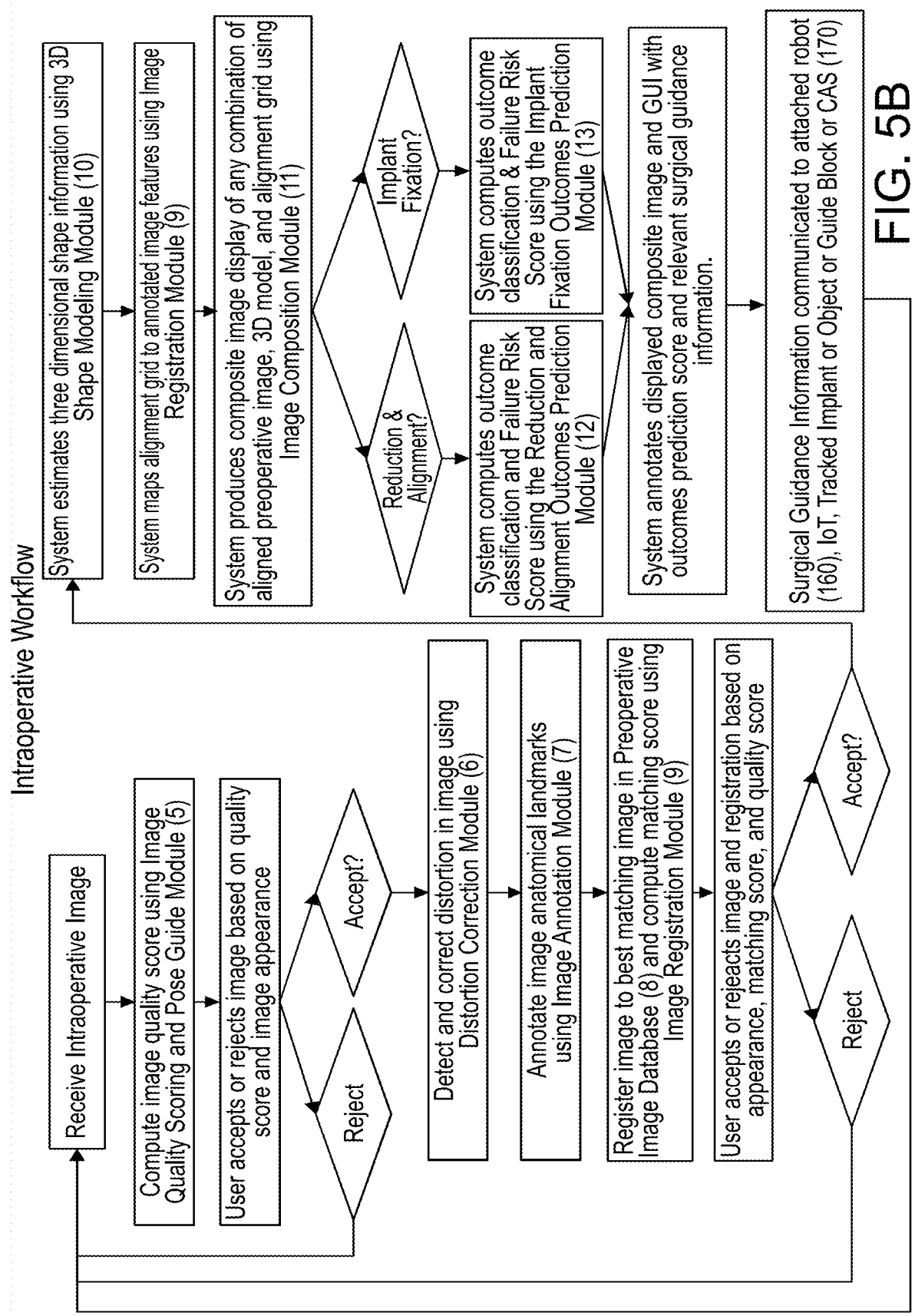

FIG. 5B is an overview of intraoperative workflow of the present invention.

Figure 5C:
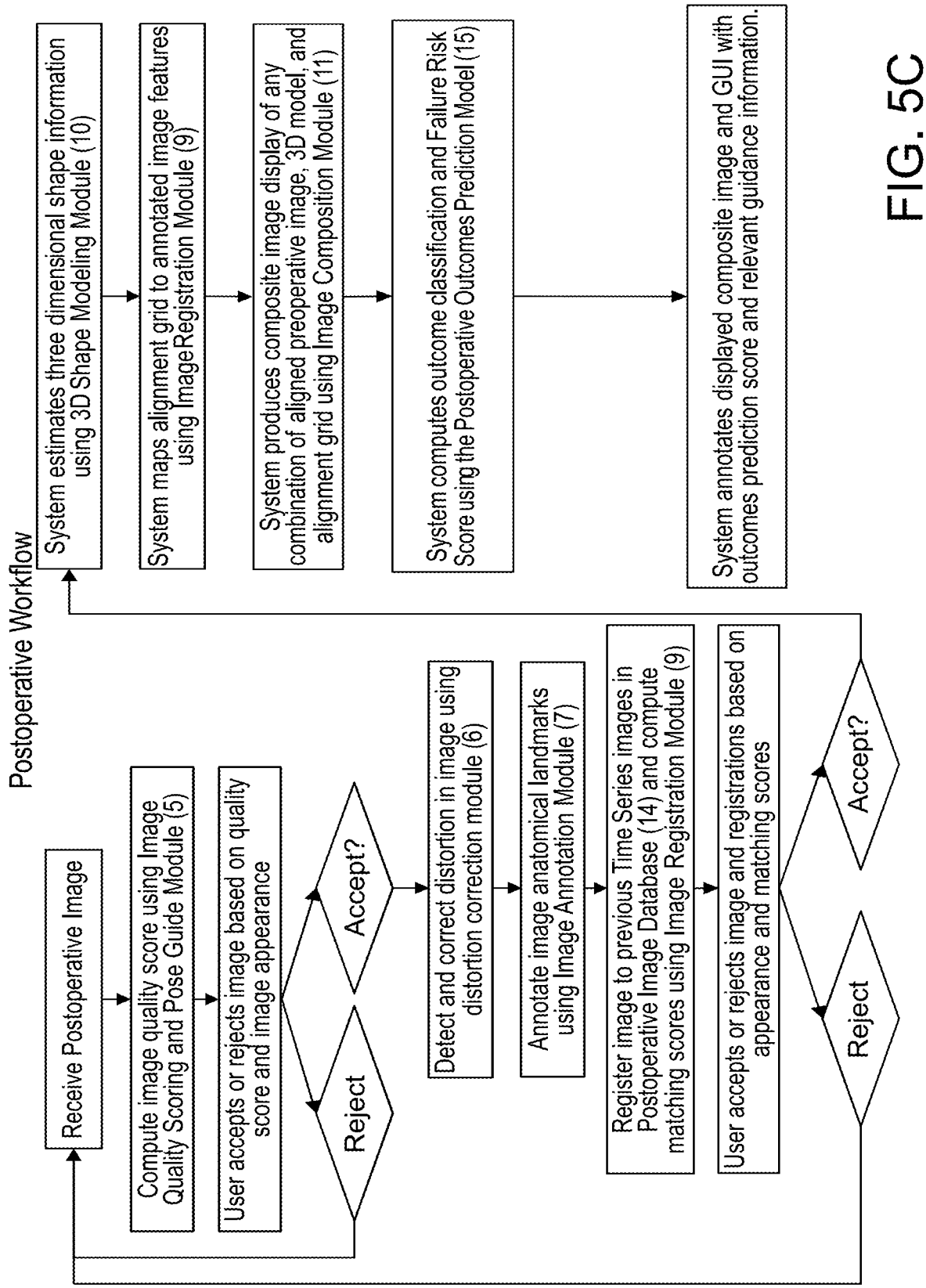

FIG. 5C is an image of a postoperative workflow of the present invention.

Figure 6:
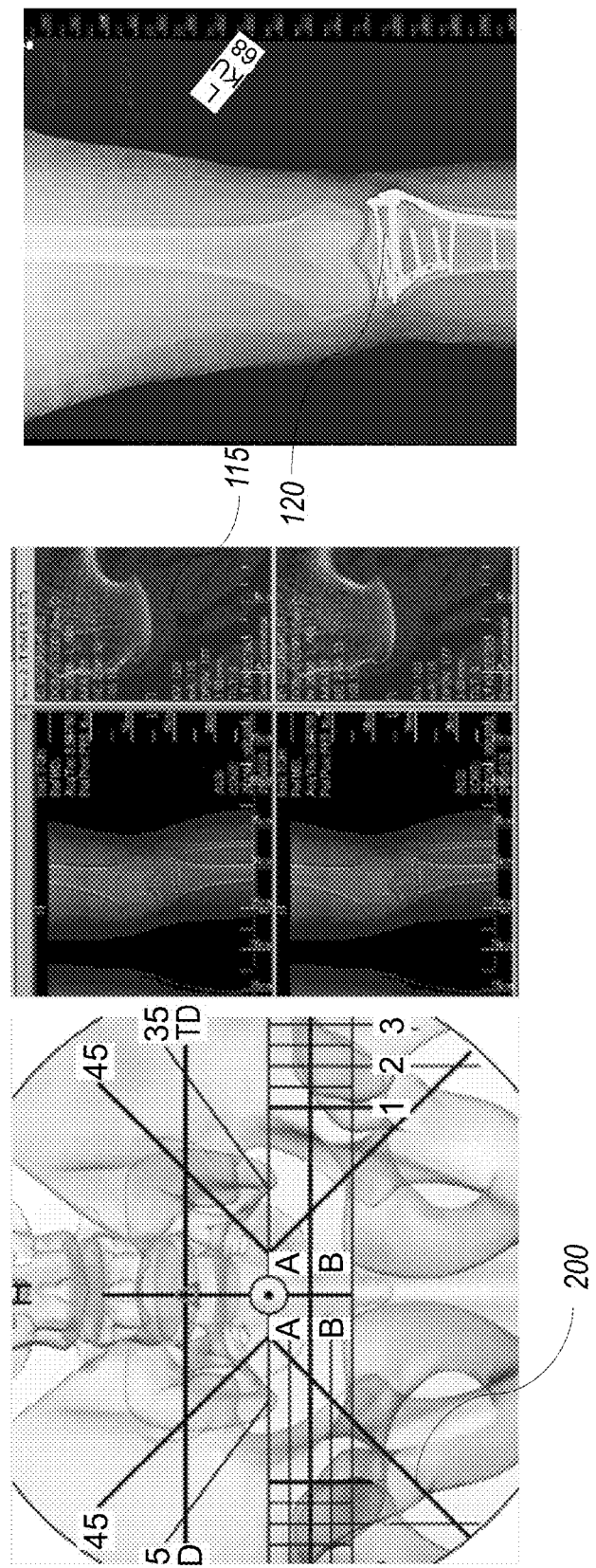

FIG. 6 is a preoperative image.

Figure 7A:
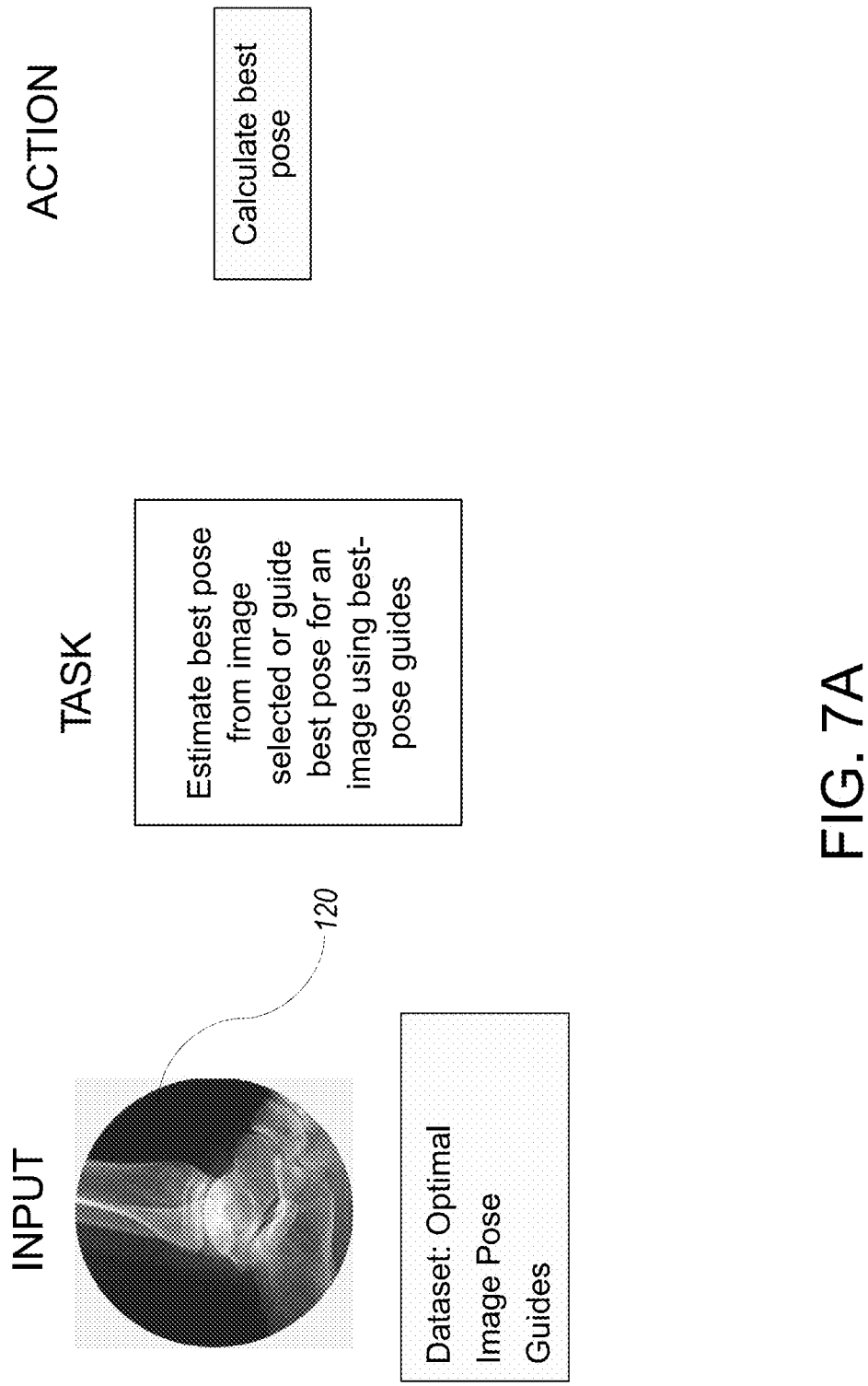

FIG. 7A is a preoperative image shown with procedure specific application relevant information as the input with the resultant tasks and actions.

Figure 7B:
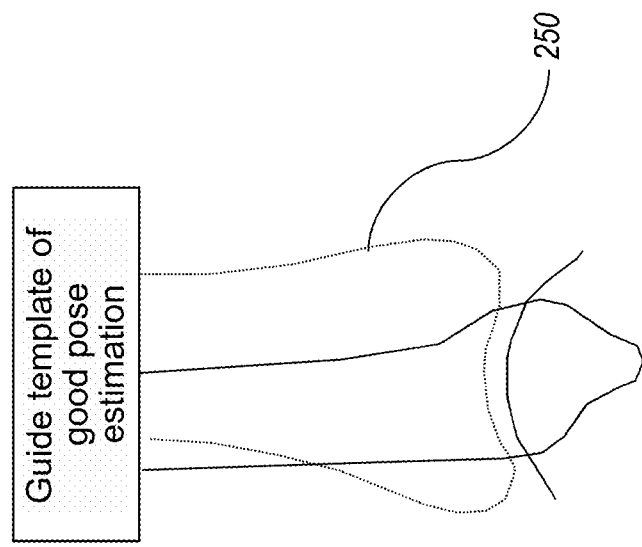

FIG. 7B is the output of the anatomical position model showing a guide template of good pose estimation.

Figure 8A:
Figure 8A:
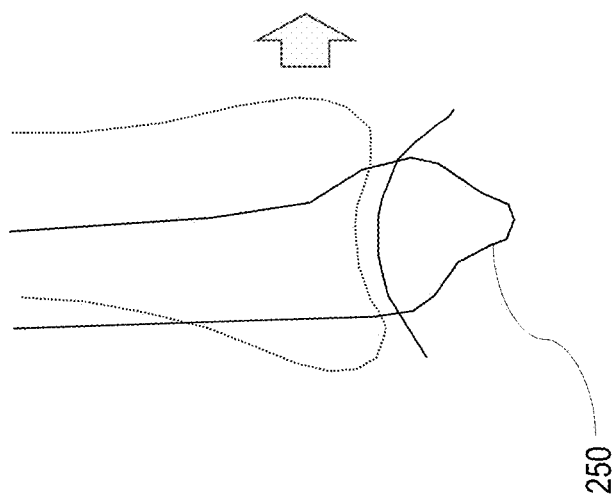

FIG. 8A is a graphical user interface showing image with grid template showing the anatomical outlines of what is a good pose.

Figure 8B:
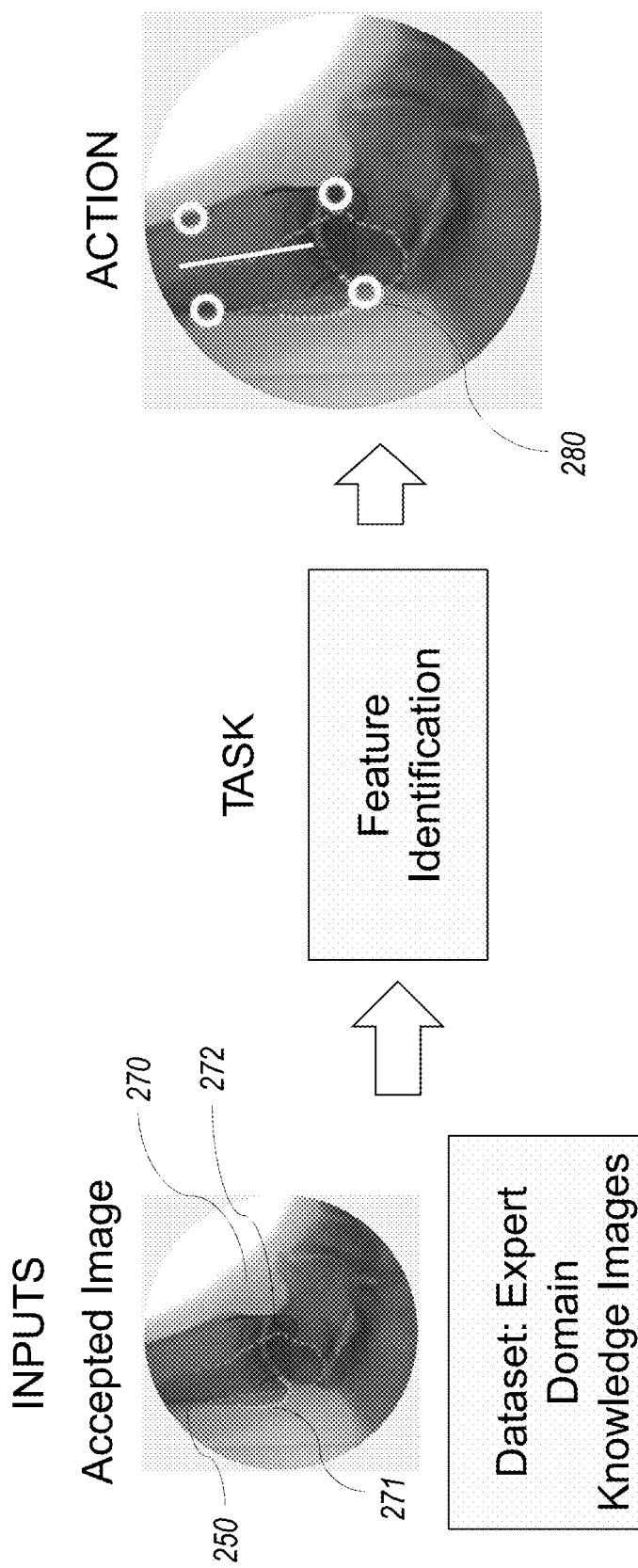

FIG. 8B shows the best image pose guidance process.

Figure 8C:
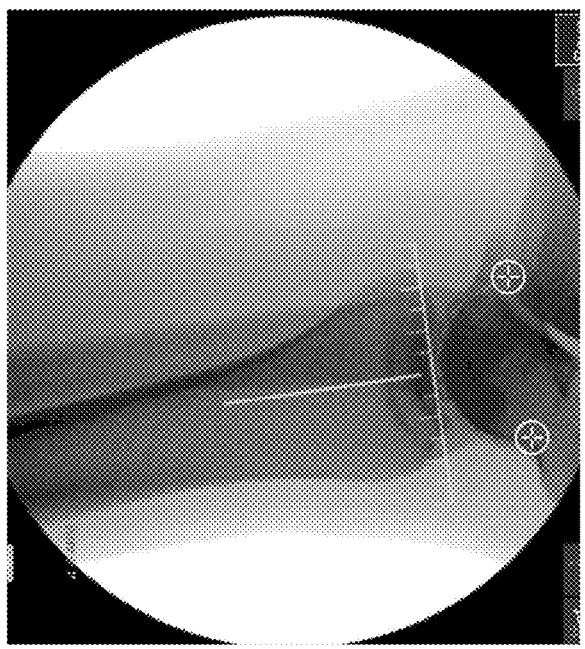
Figure 8C:
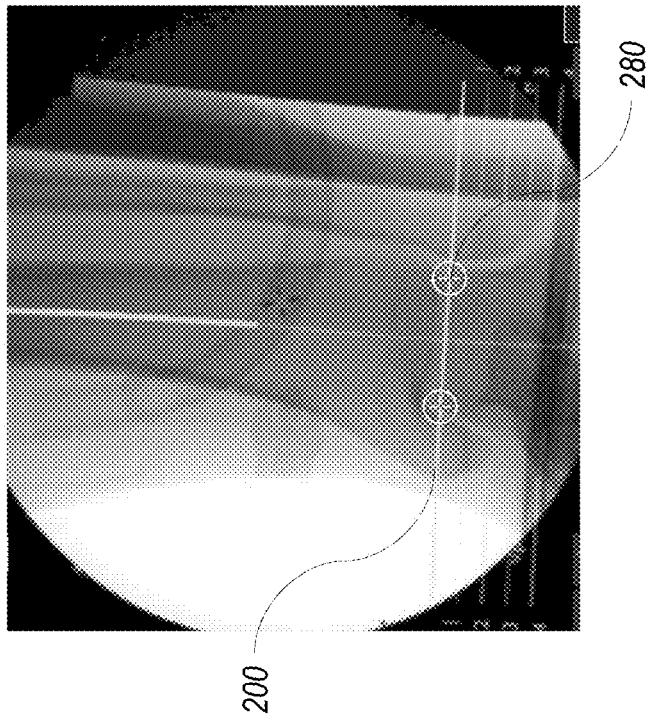

FIG. 8C shows the output of the use of a reference image.

Figure 9A:
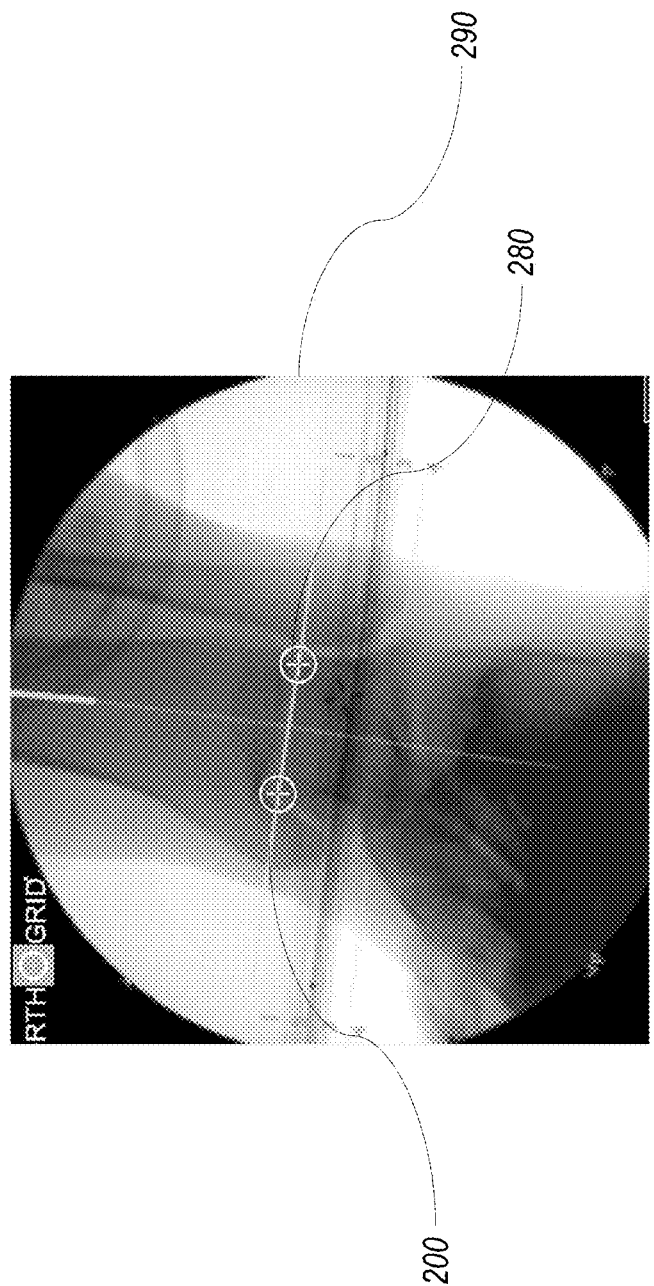

FIG. 9A is a graphical user interface showing an image with anatomical features defined.

Figure 9B:
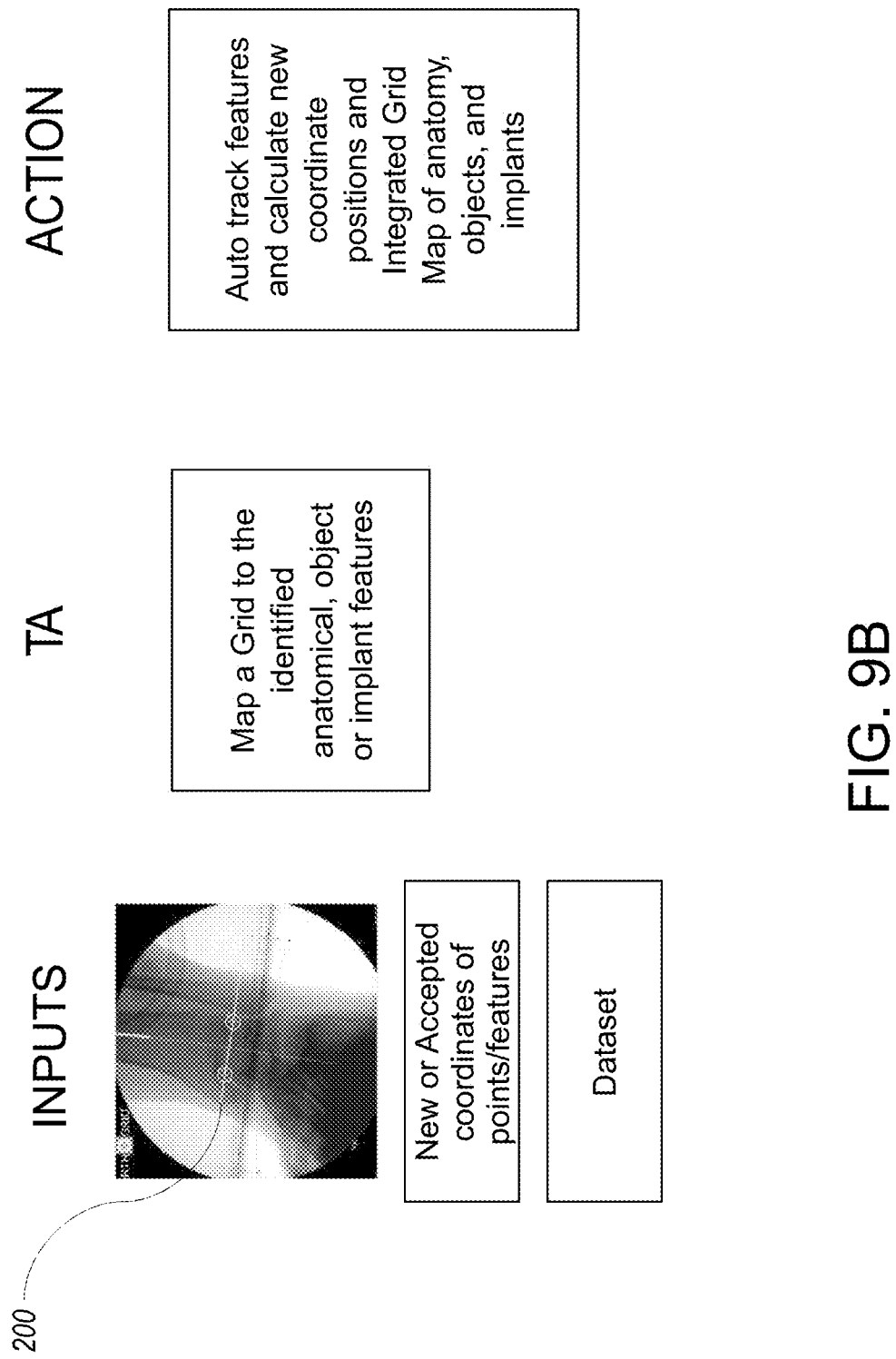

FIG. 9B shows user inputs, task and actions.

Figure 10:
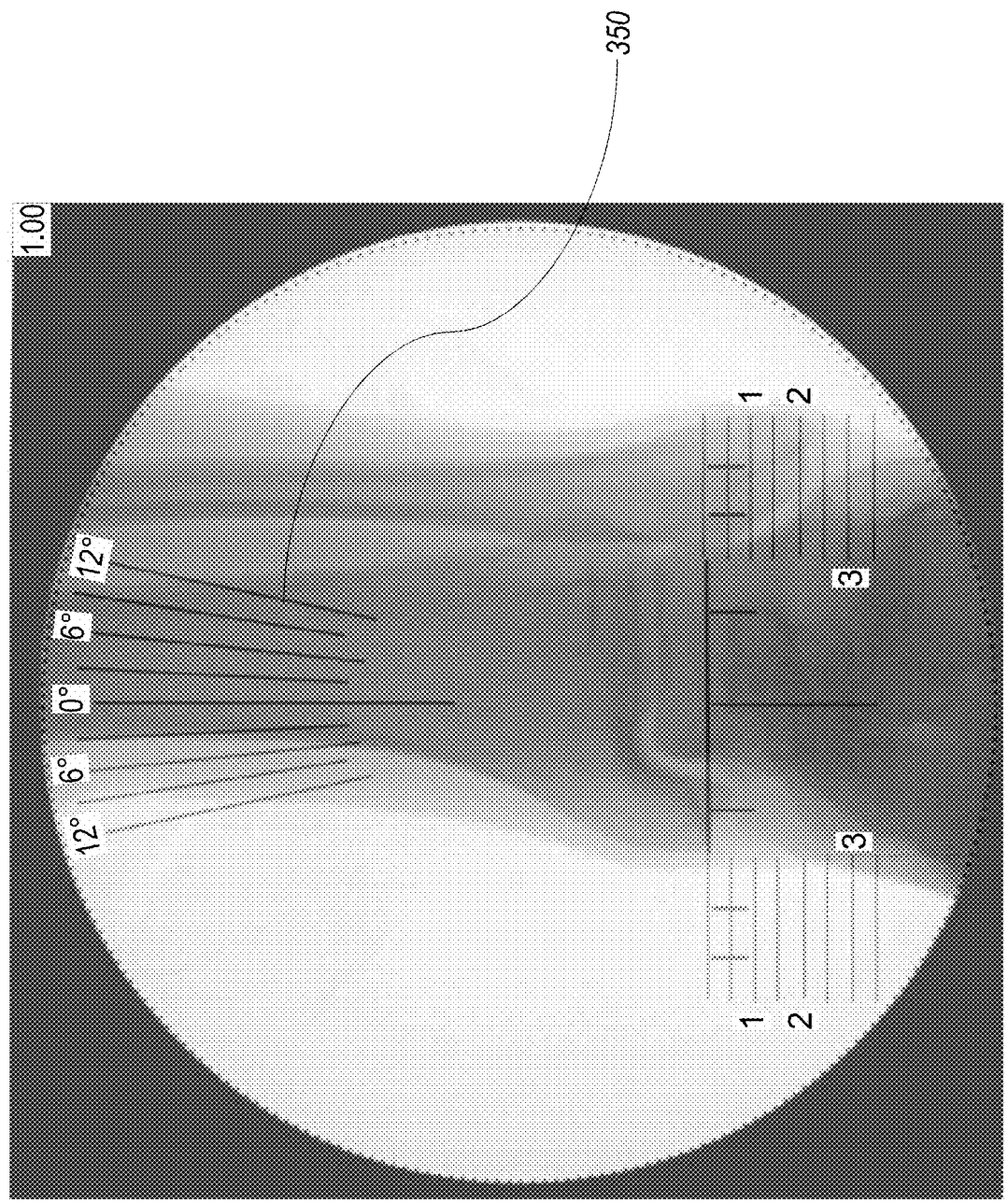

FIG. 10 is a graphical user interface showing anatomical measurement grid positioned on an image.

Figure 11A:
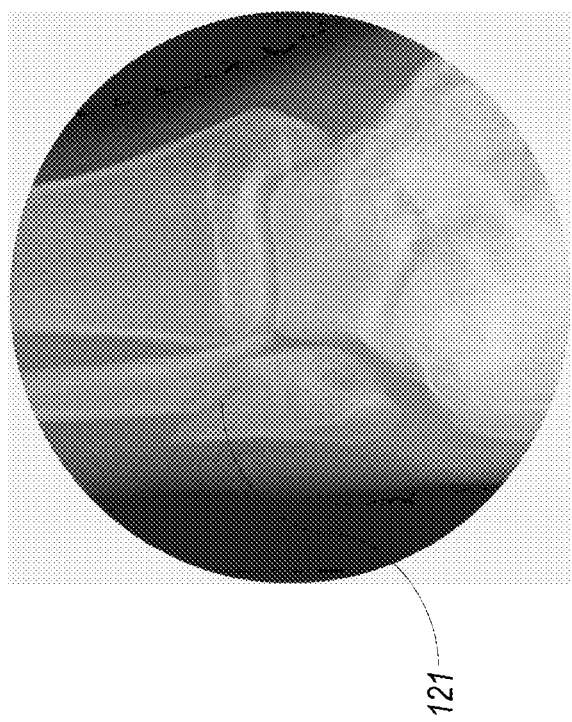

FIG. 11A is a graphical user interface showing an image of the affected side.

Figure 11B:
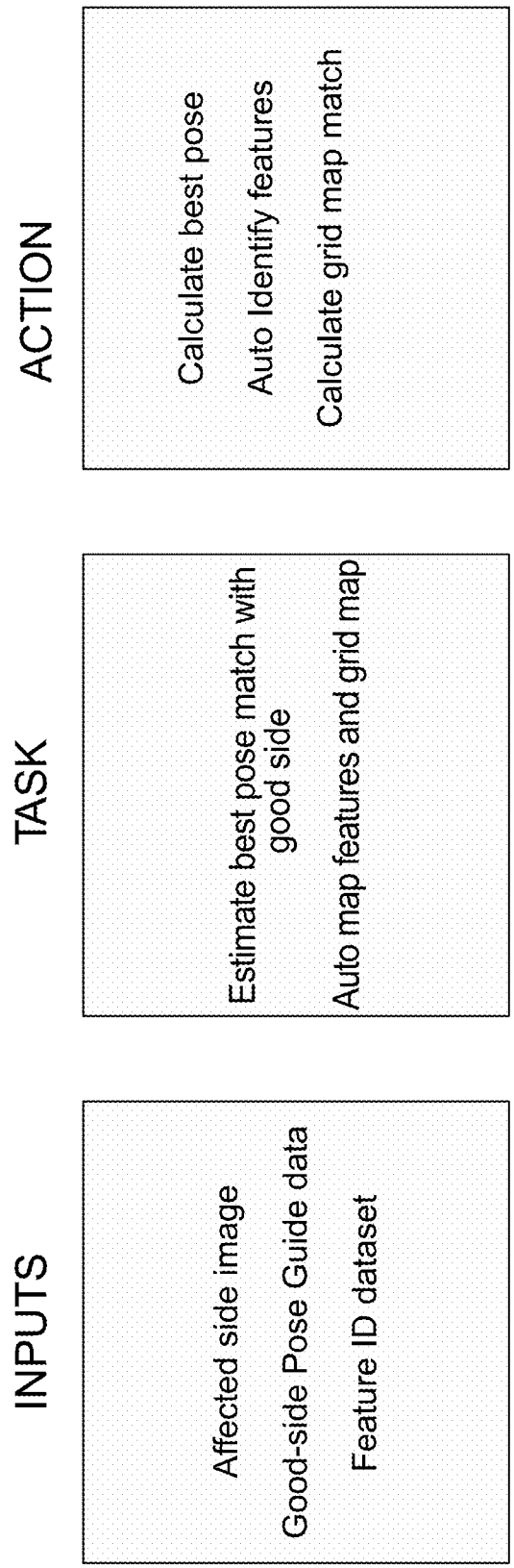

FIG. 11B shows user inputs, task and actions.

Figure 12A:
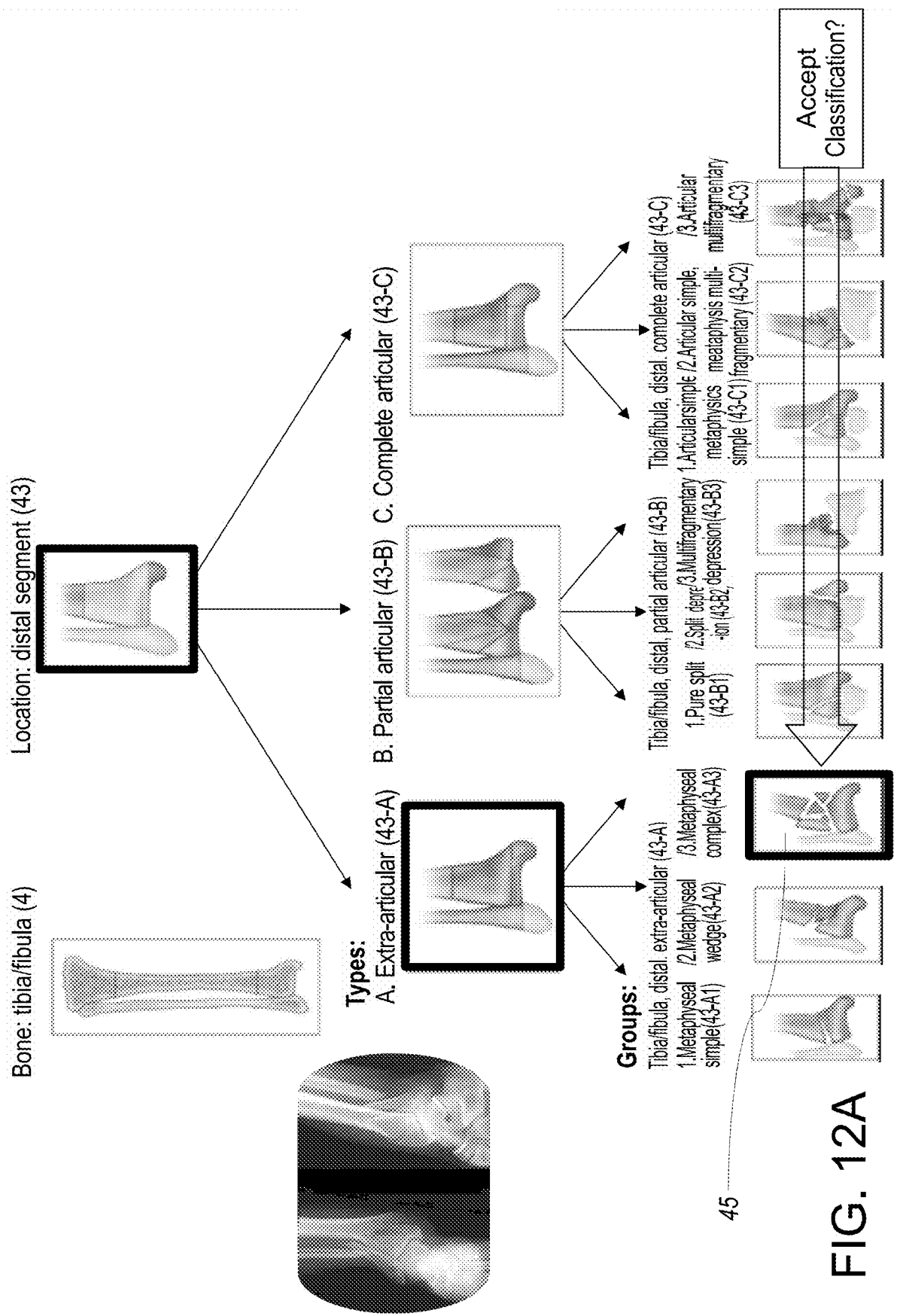

FIG. 12A is a graphical user interface showing a display of accepted image classification.

Figure 12B:
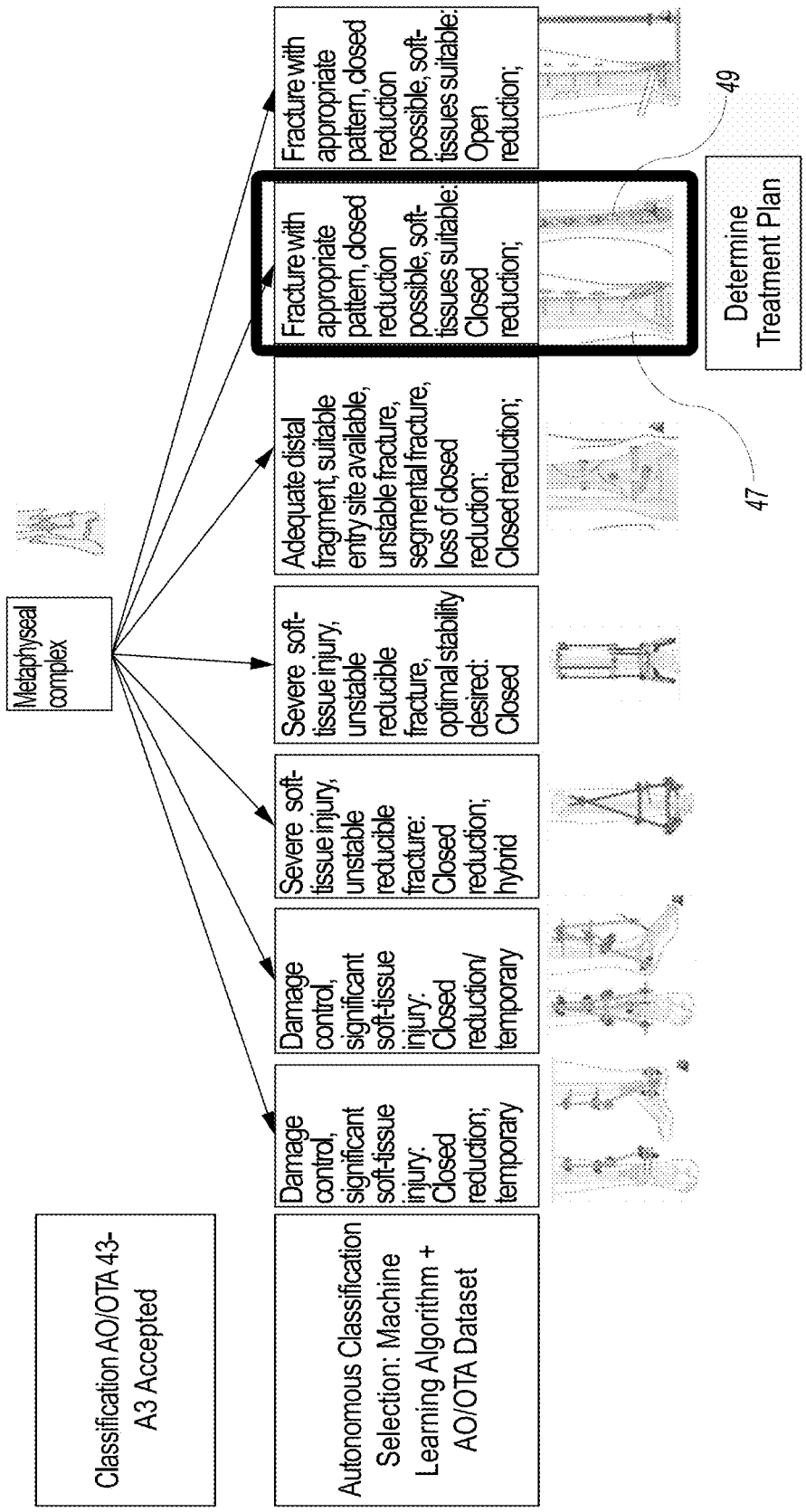

FIG. 12B shows user inputs, task and actions relating to the formulation of a treatment plan.

Figure 13A:
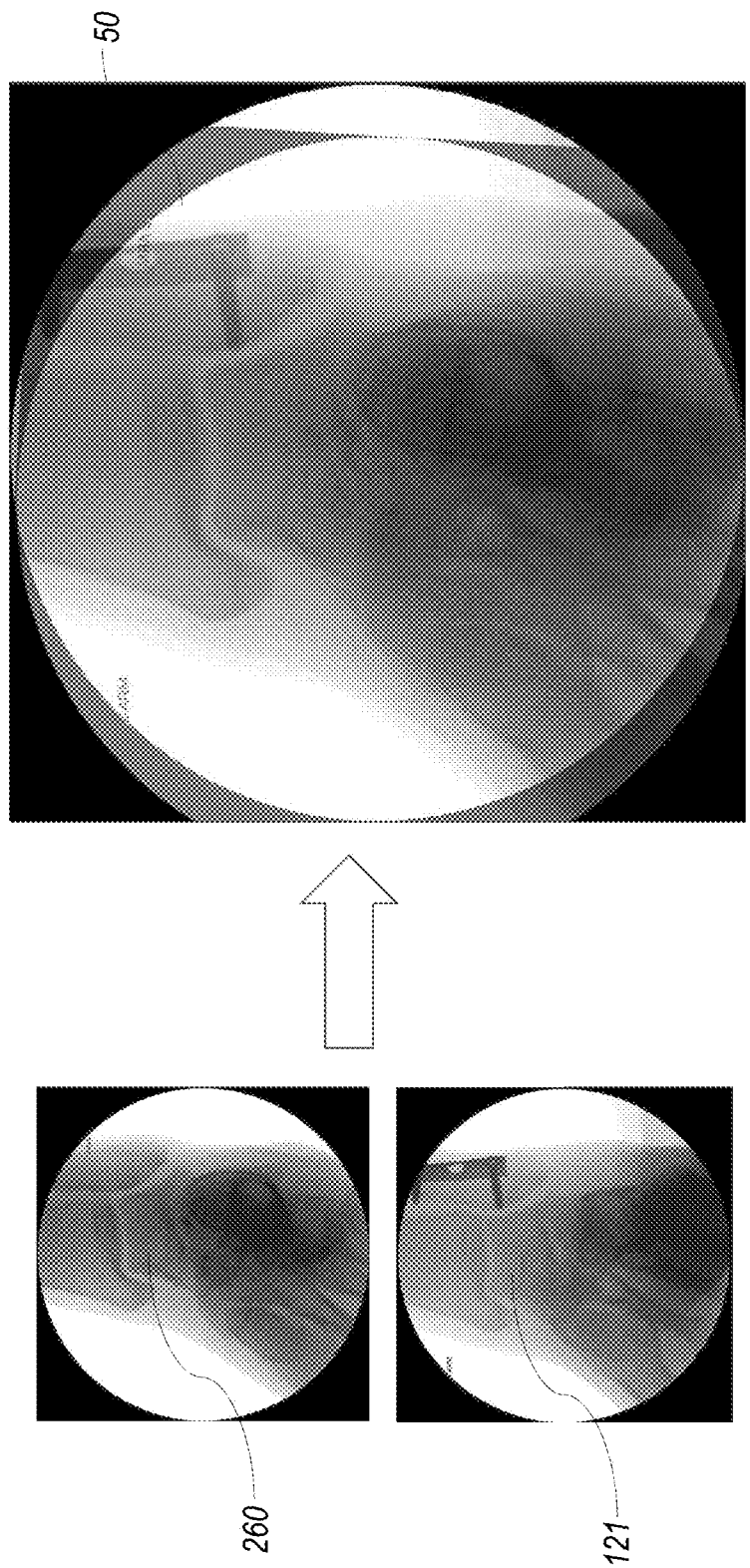

FIG. 13A is a graphical user interface showing ghosting.

Figure 13B:
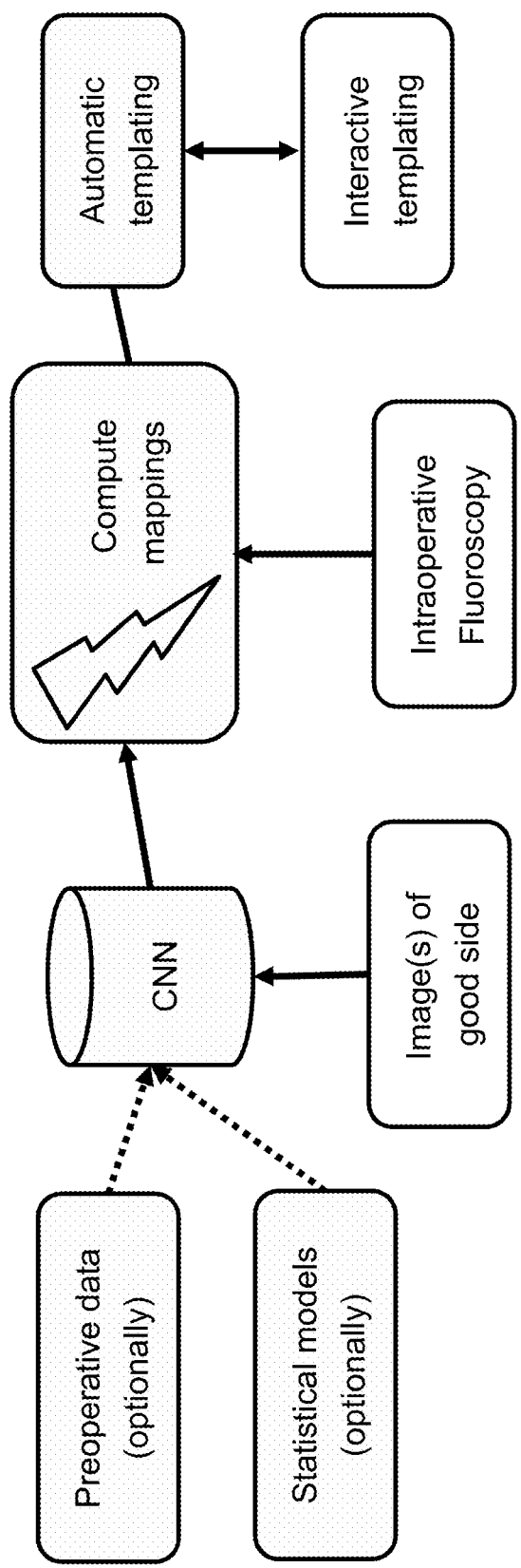

FIG. 13B shows the data flow in ghosting.

Figure 14A:
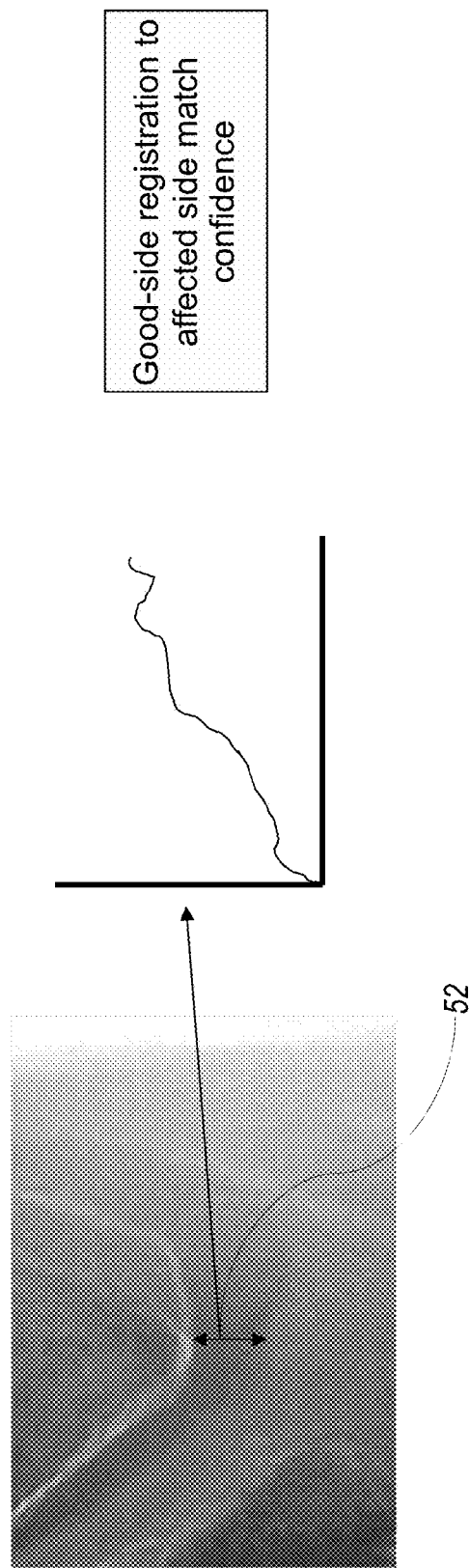

FIG. 14A is a graphical user interface showing grid similarity with match confidence display.

Figure 14B:
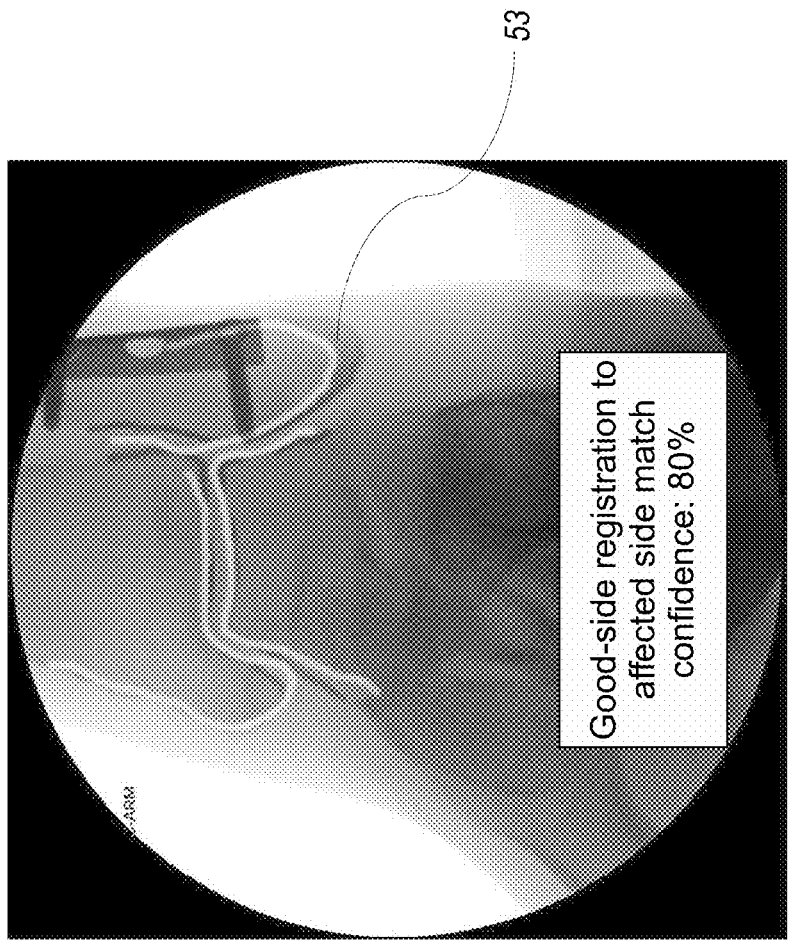

FIG. 14B shows the output of a graphical user interface showing confirmation of good-side for further use.

Figure 14C:
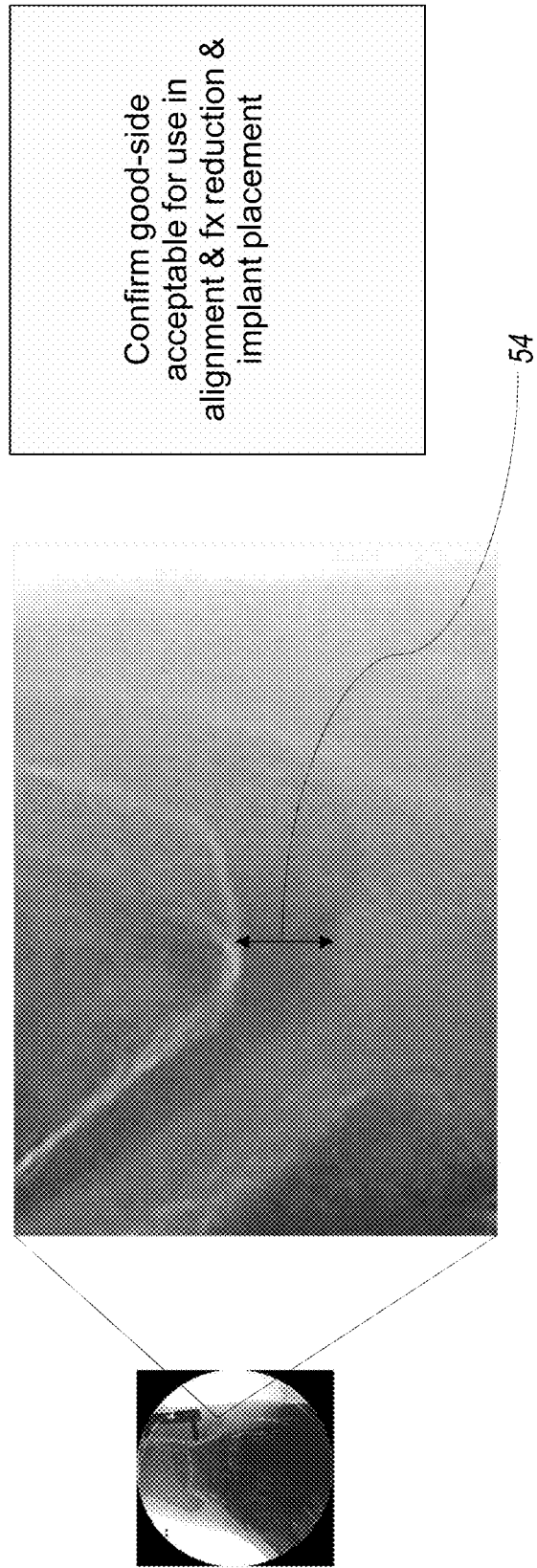

FIG. 14C shows the good side acceptance.

Figure 15A:
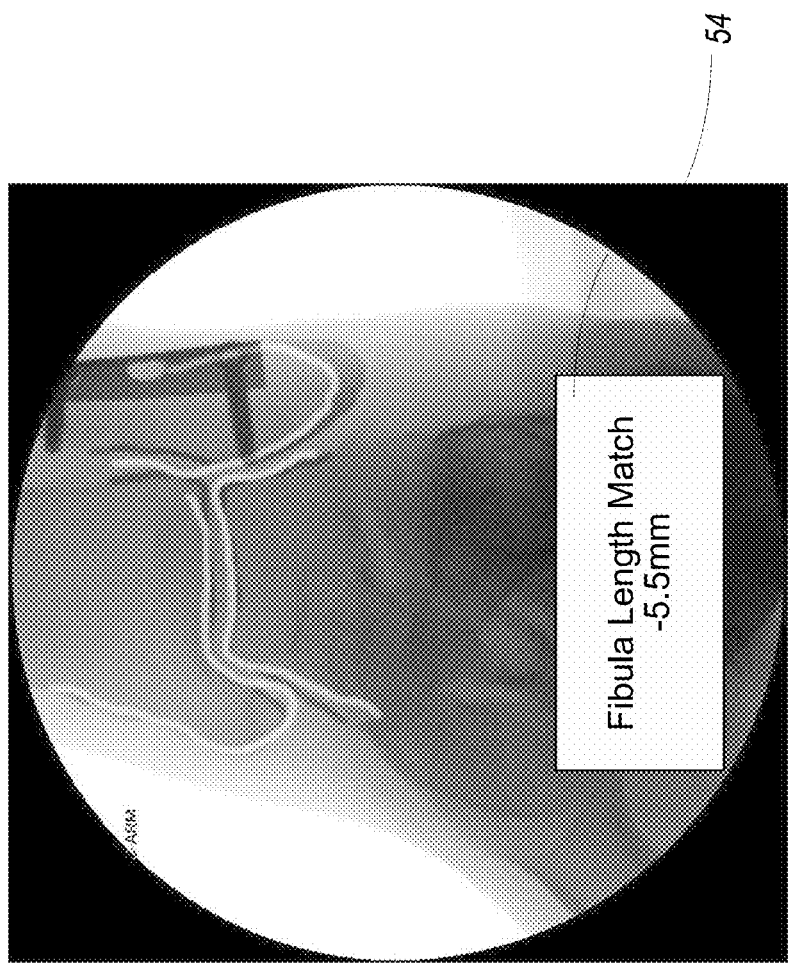

FIG. 15A is a graphical user interface showing an image of the good-side overlay with grid alignment and measurements.

Figure 15B:
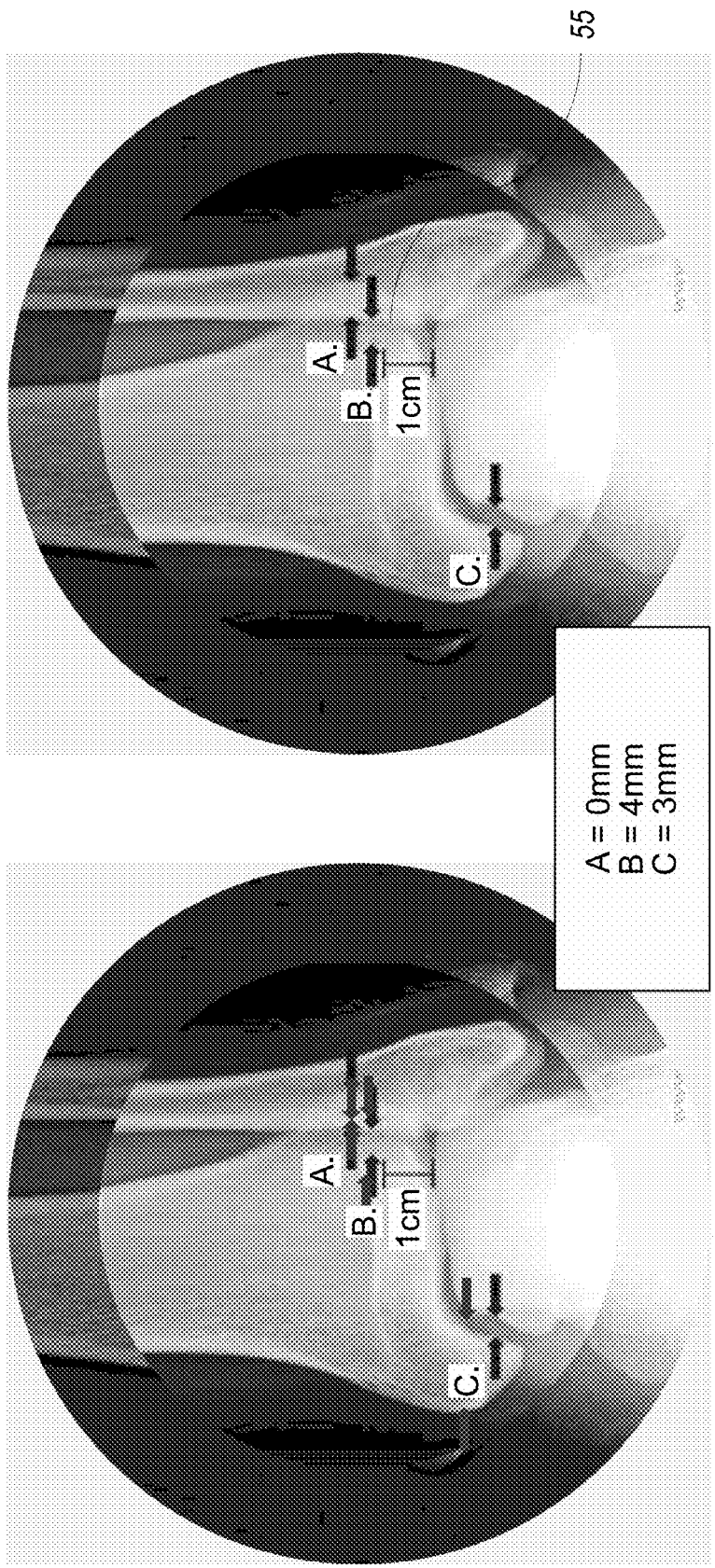

FIG. 15B is a graphical user interface showing an image of the good-side overlay with grid alignment and measurements for an ankle.

Figure 15C:
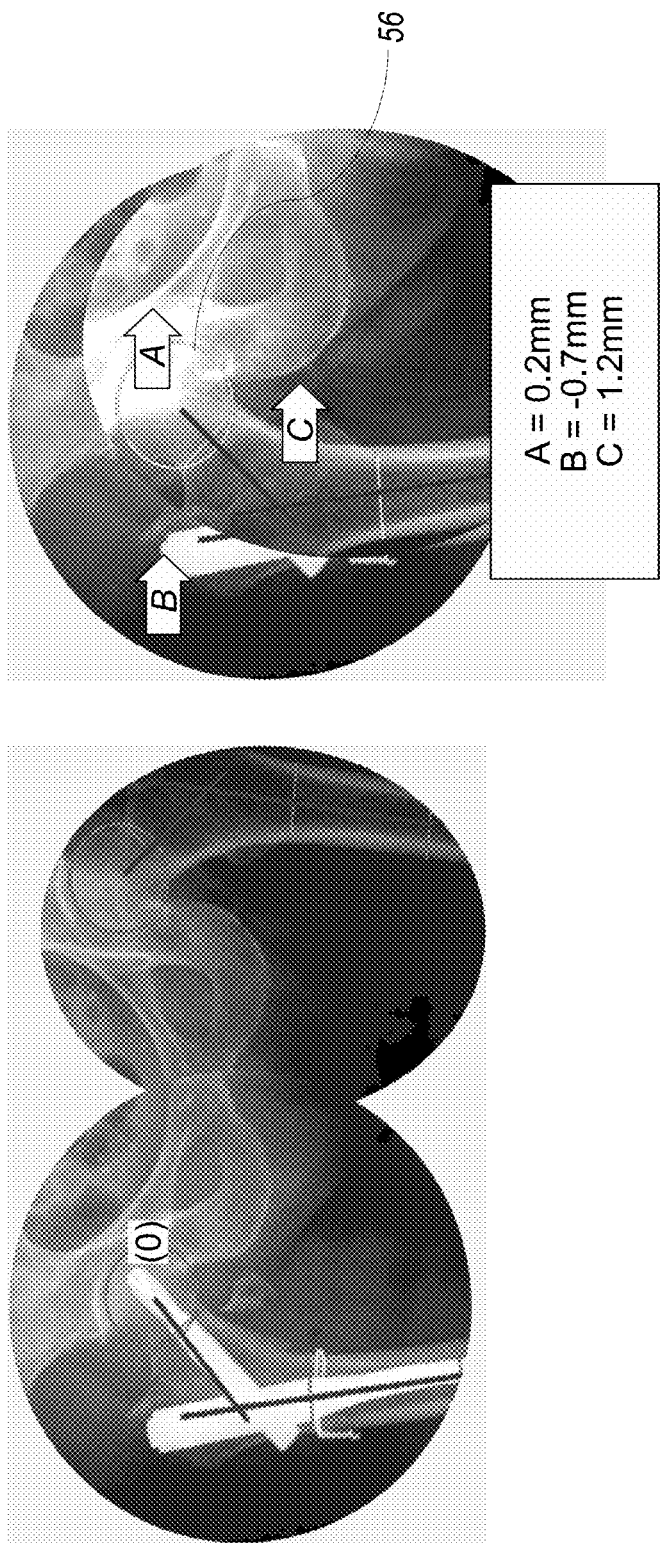

FIG. 15C is a graphical user interface showing an image of the good-side overlay with grid alignment and measurements for a nail.

Figure 16:
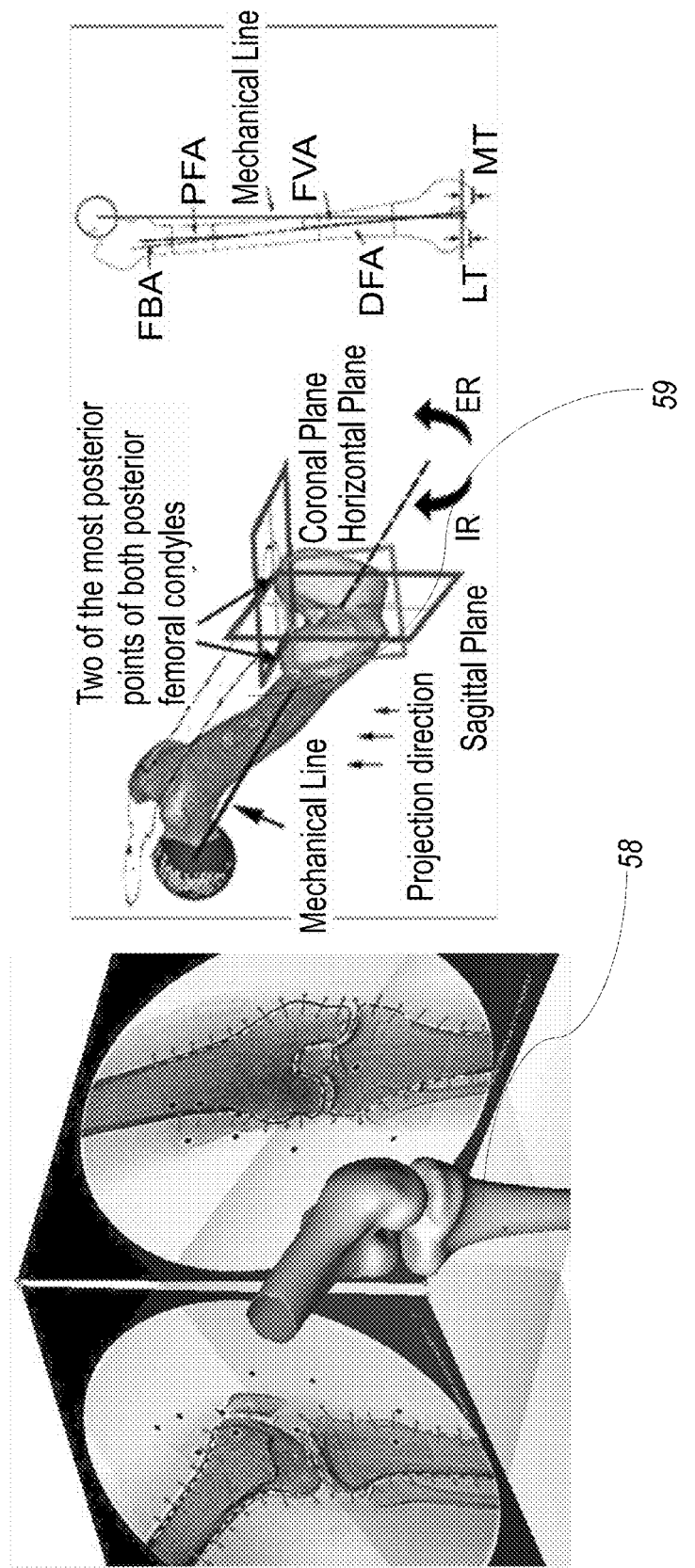

FIG. 16 is a representation of statistical inference of 3D models and an example of the use of representation of statistical inference of 3D models.

Figure 17A:
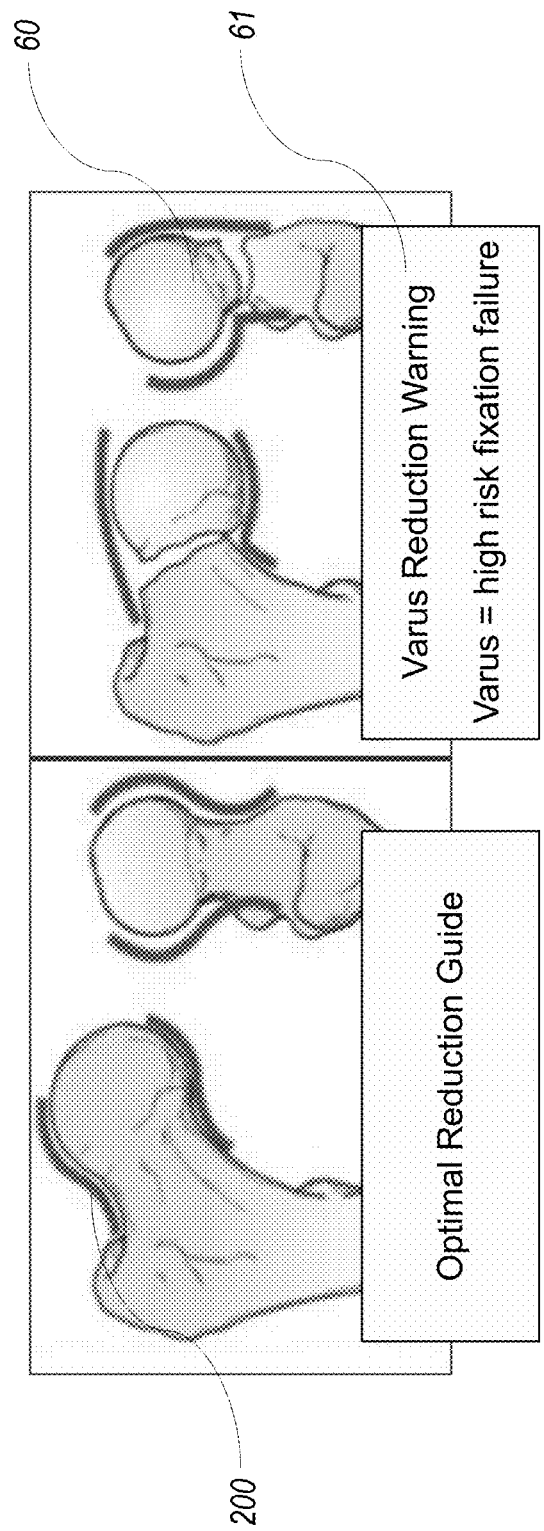

FIG. 17A shows an image of anatomy alignment and fracture reduction guidance.

Figure 17B:
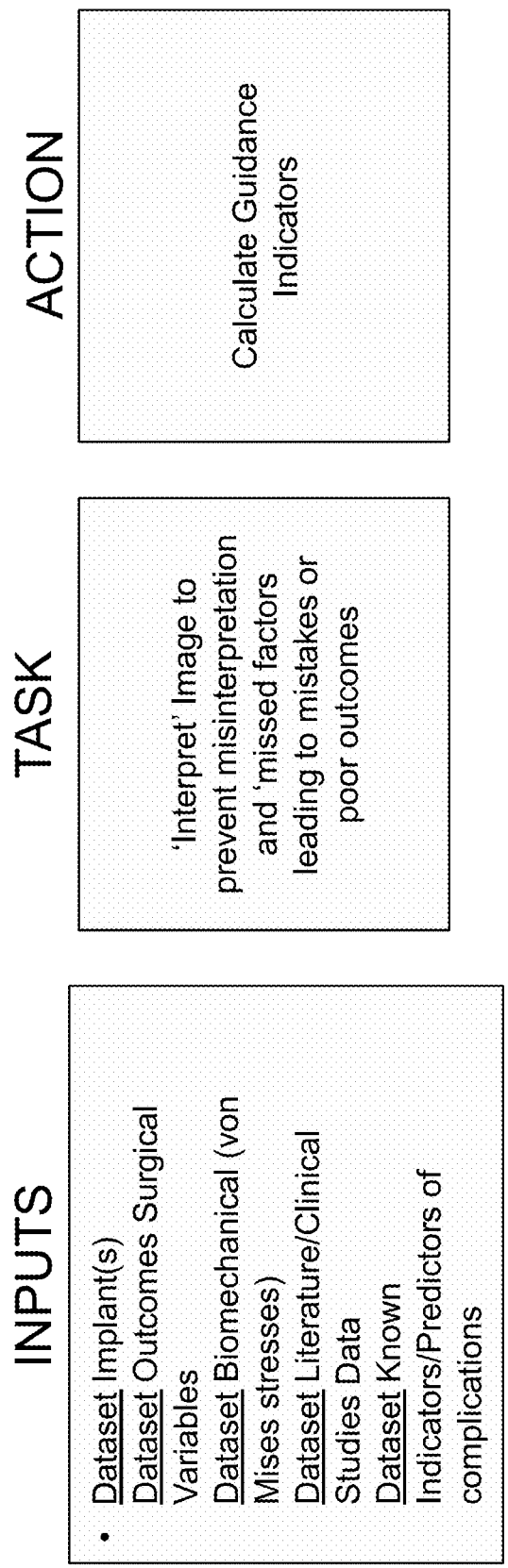

FIG. 17B shows user inputs, task and actions related to the datasets.

Figure 18A:
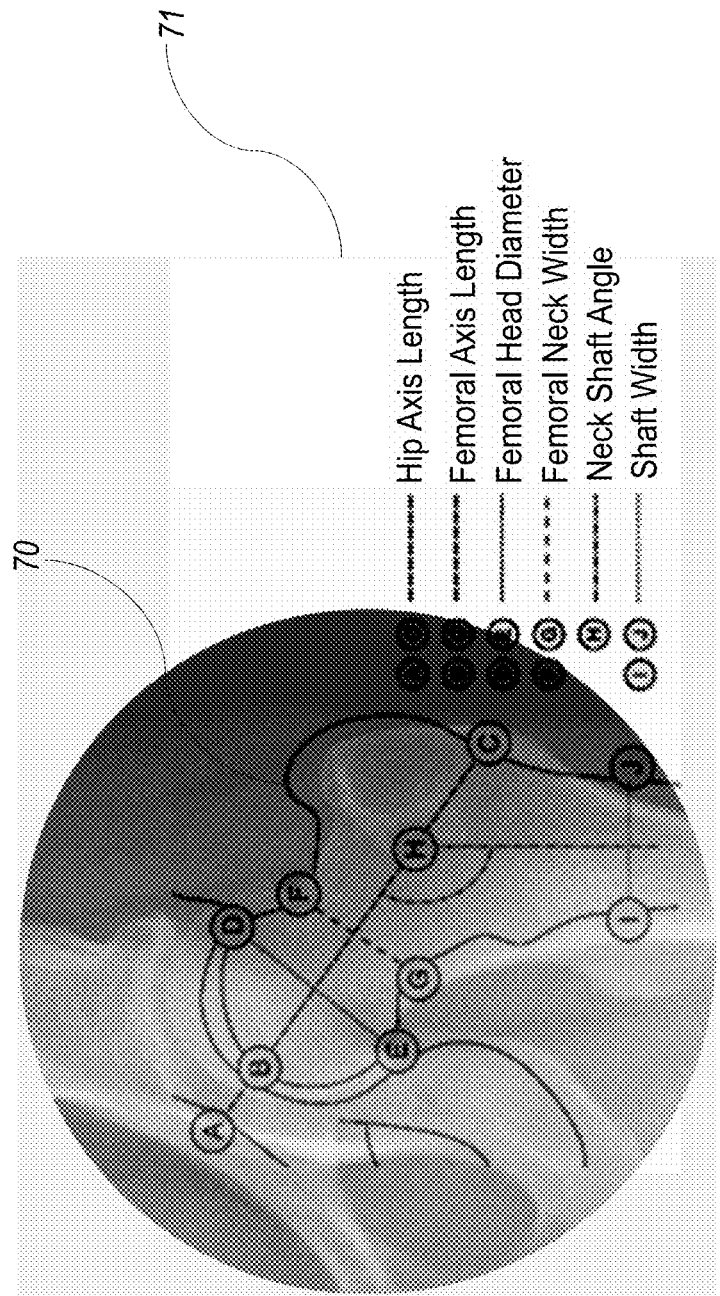

FIG. 18A is a graphical user interface instrument guidance.

Figure 18B:
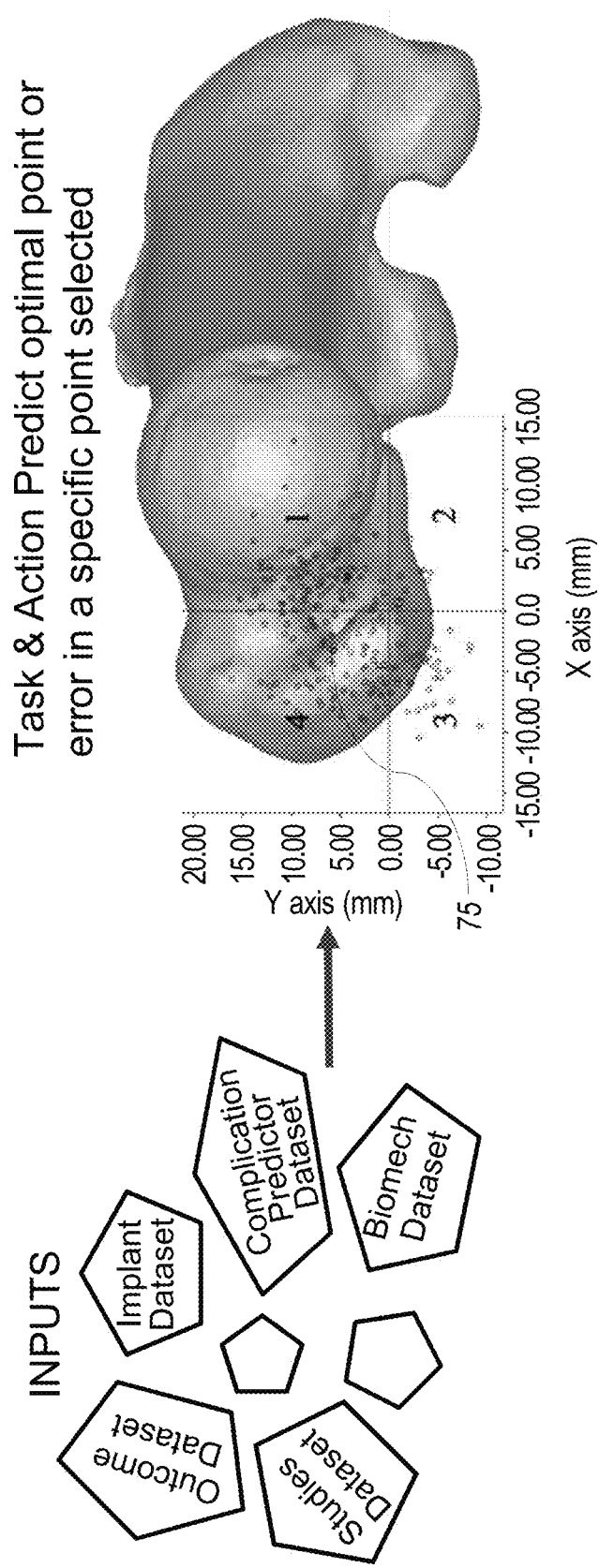

FIG. 18B shows user inputs, task and actions related to the datasets.

Figure 18C:
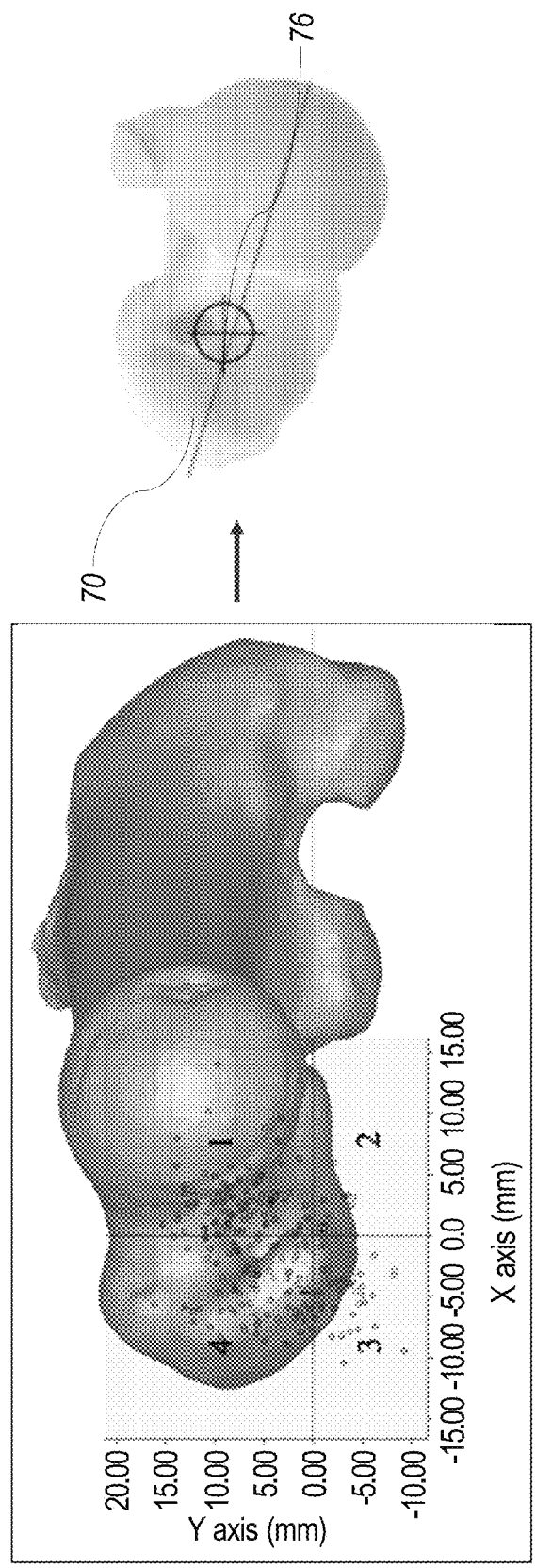

FIG. 18C shows various outputs

Figure 18D:
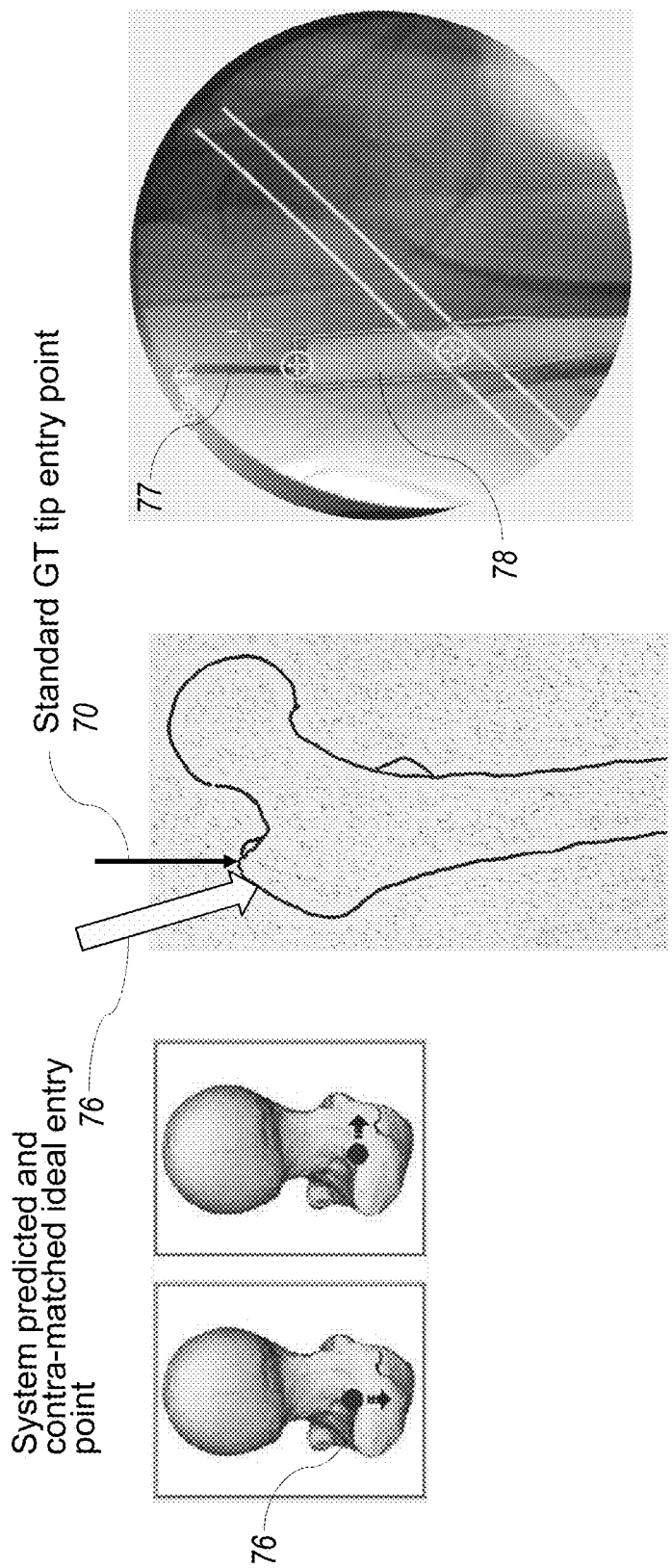

FIG. 18D shows the predictive and contra-side matched ideal entry point.

Figure 19A:
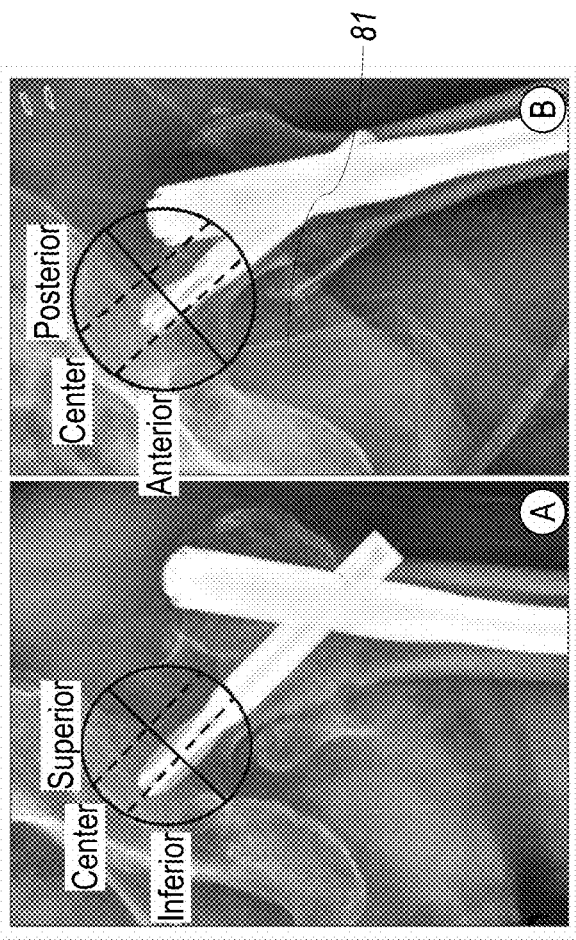
Figure 19A:
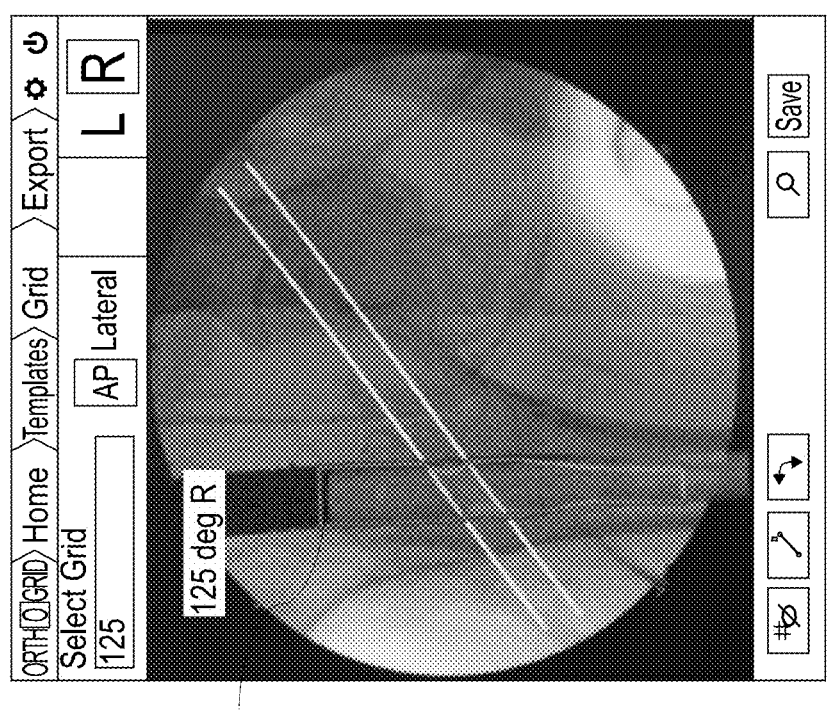

FIG. 19A is a graphical user interface showing instrument guidance and or virtual implant placement.

Figure 19B:
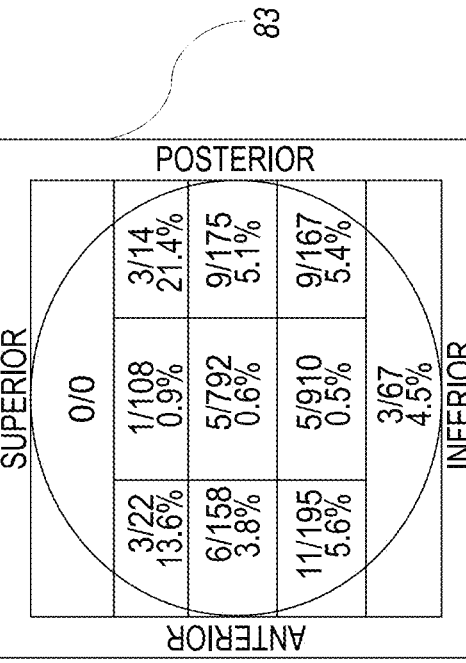
Figure 19B:
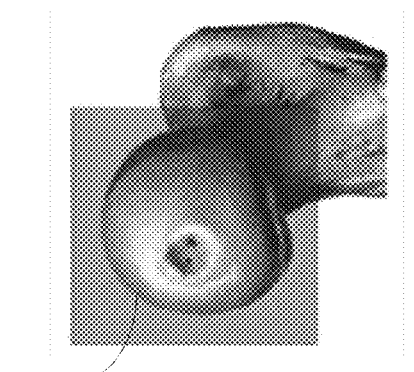
Figure 19B:
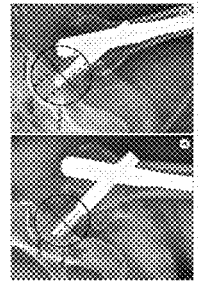

FIG. 19B is a graphical user interface showing instrument guidance and or virtual implant placement of lag screw placement.

Figure 20A:
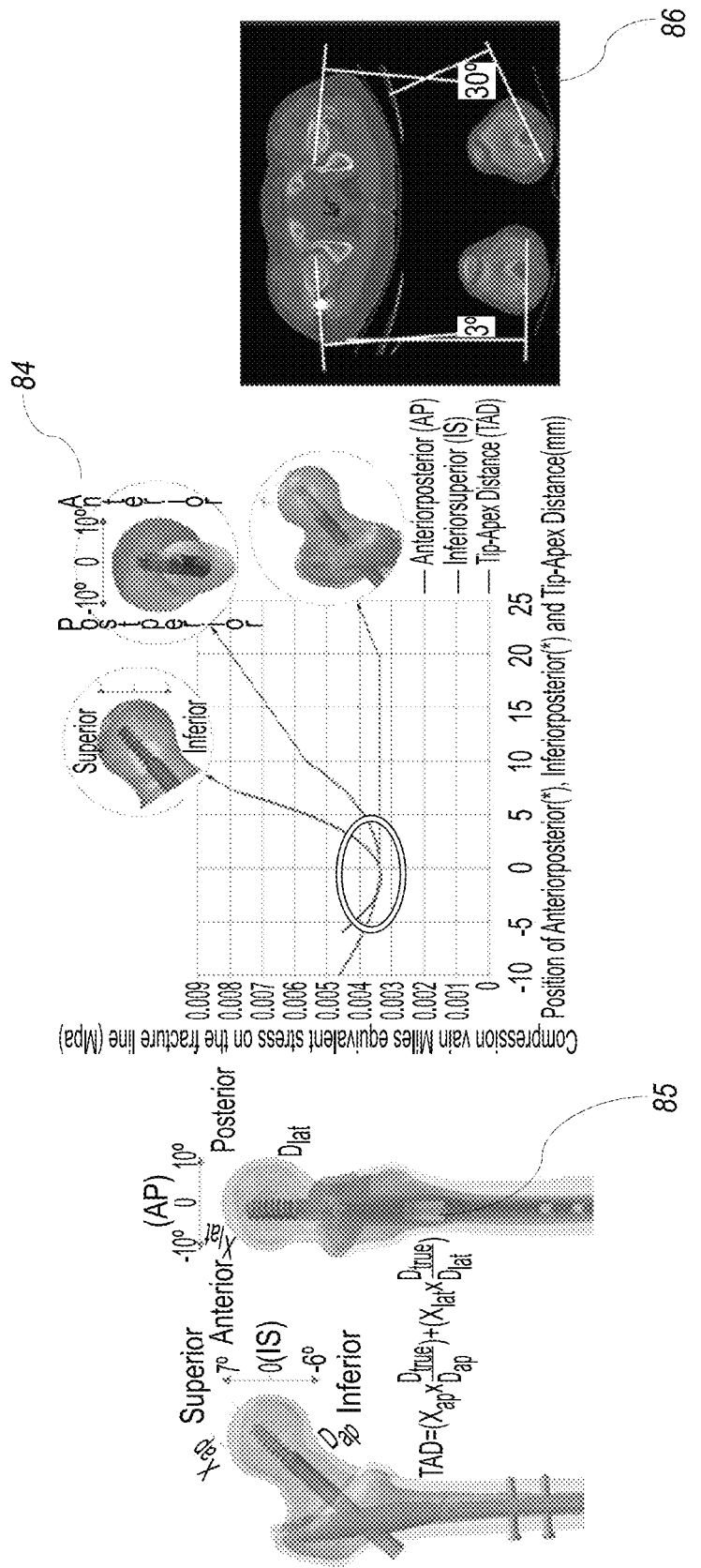

FIG. 20A shows user output related to lag screw placement.

Figure 20B:
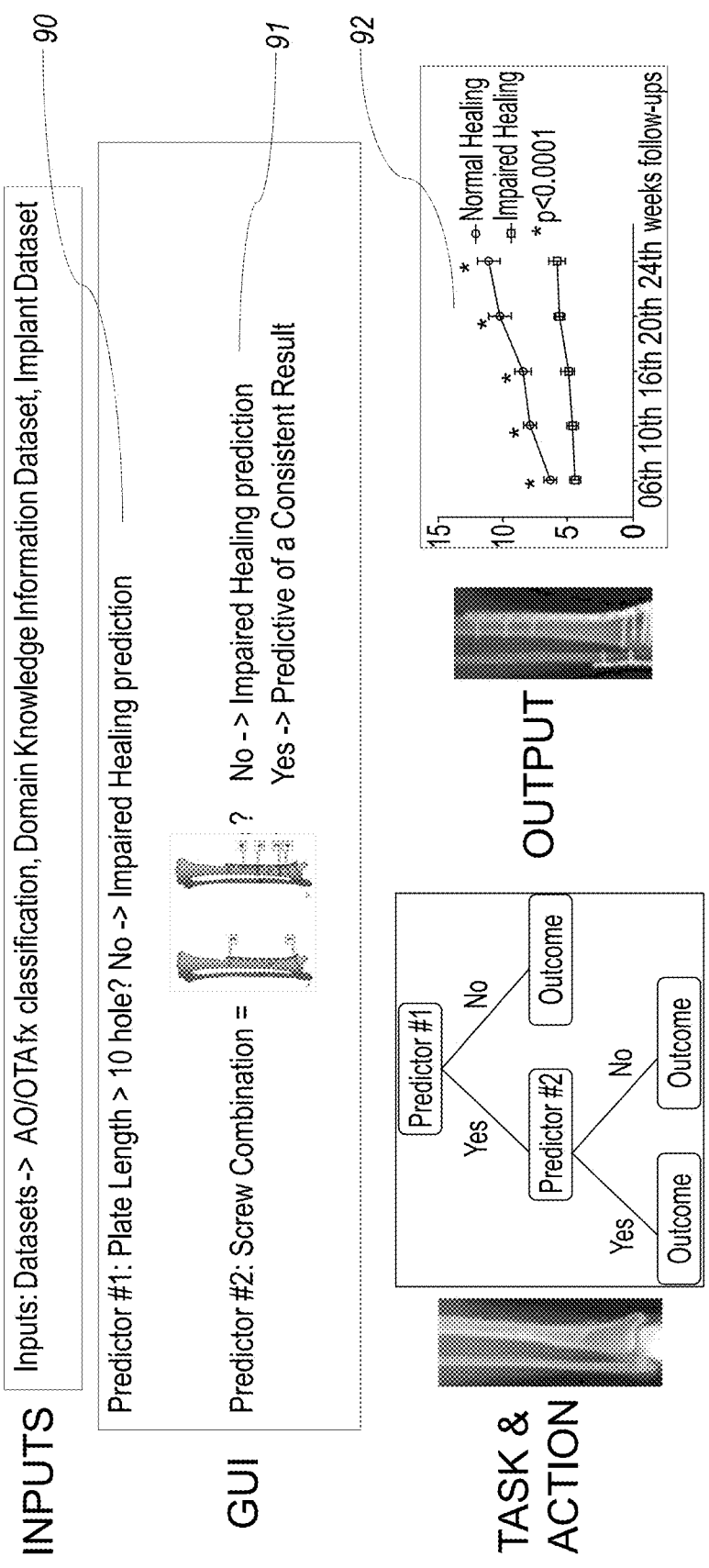

FIG. 20B shows predictor variable using a domain knowledge related to lag screw placement.

Figure 21:
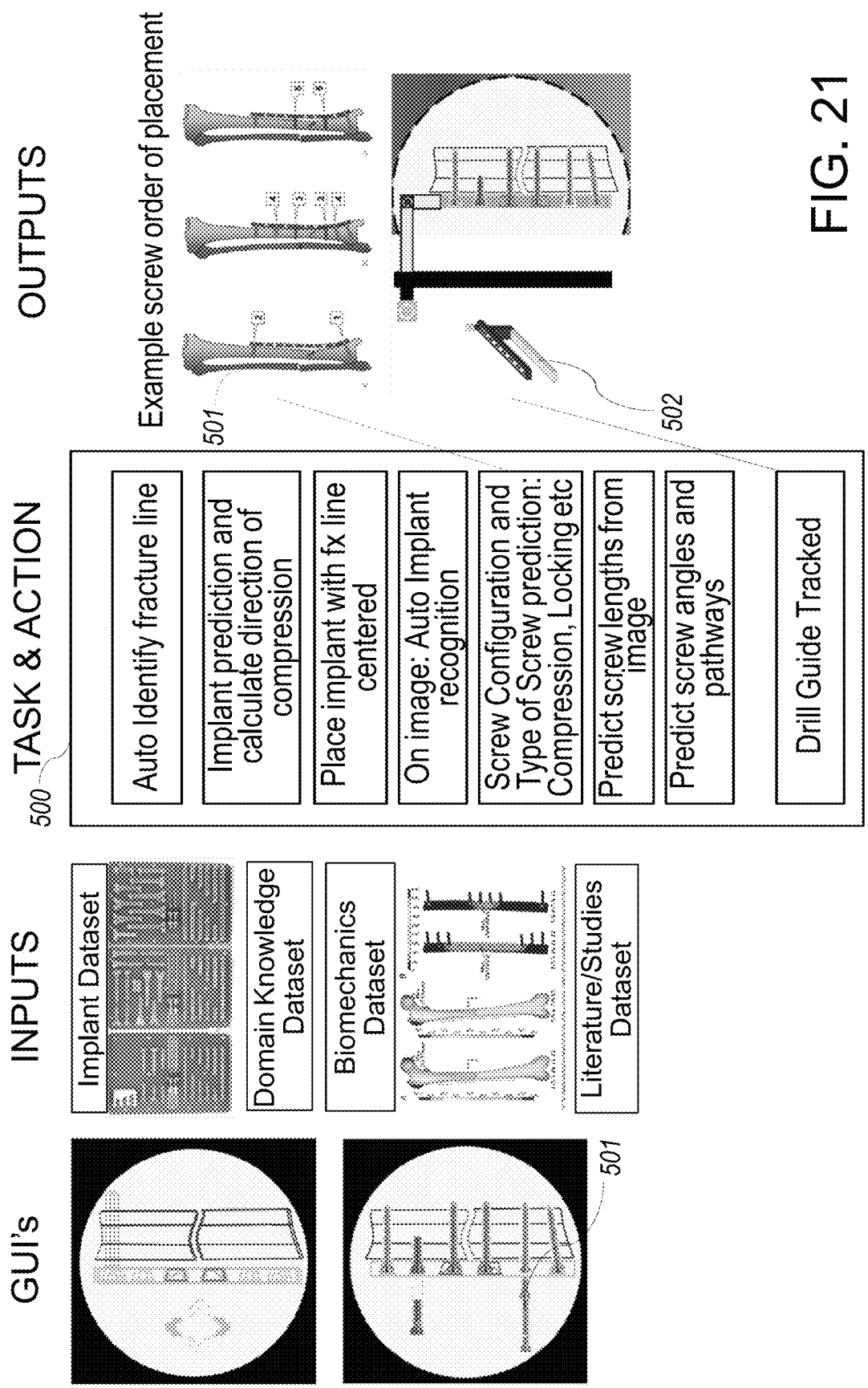

FIG. 21 shows user output related to lag screw placement using Intraoperative, Real-time Situational Guidance.

Figure 22:
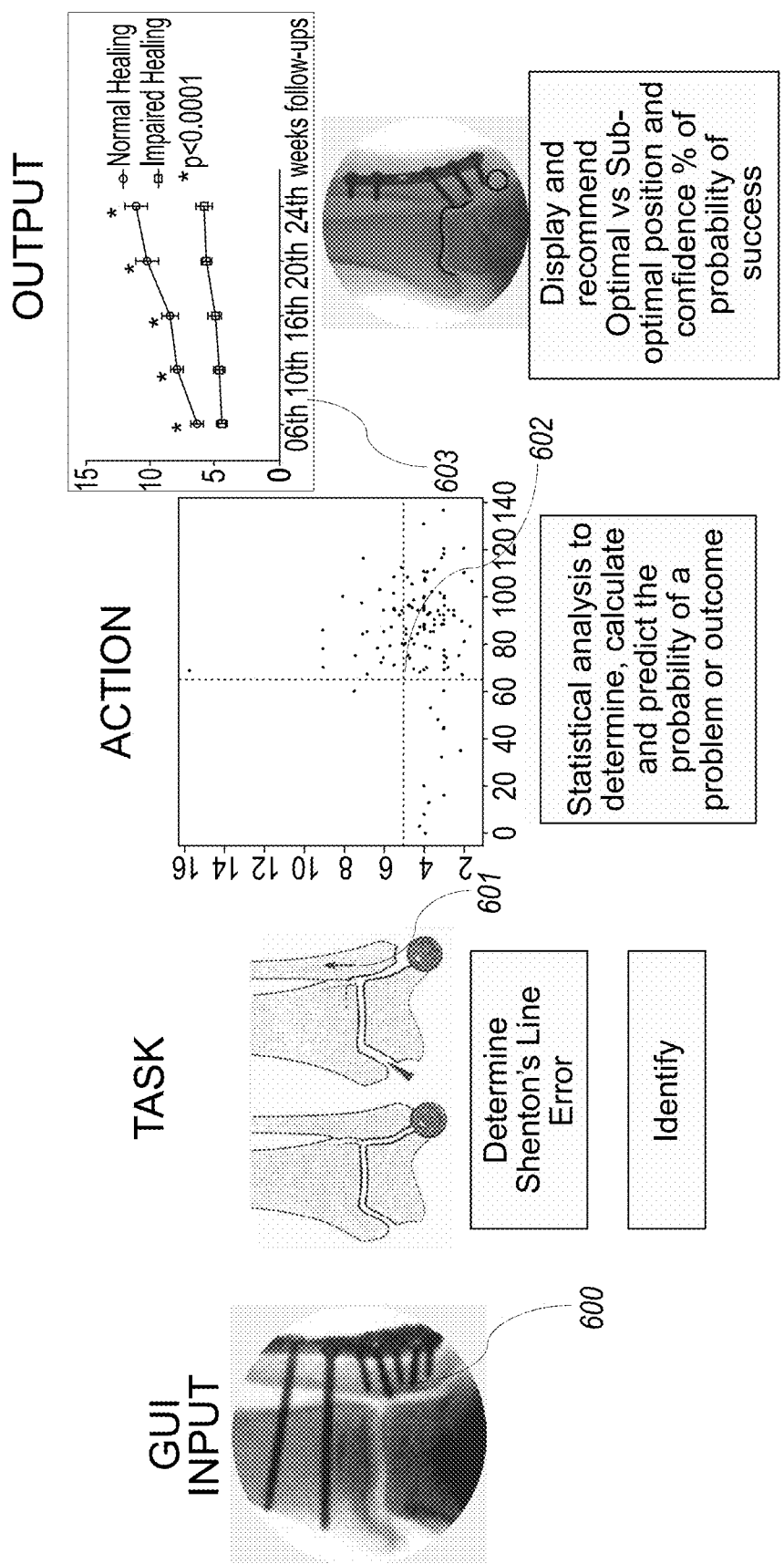

FIG. 22 shows a graphical user interface, user inputs, task and actions relating to problem prediction related to an ankle problem.

Figure 23:
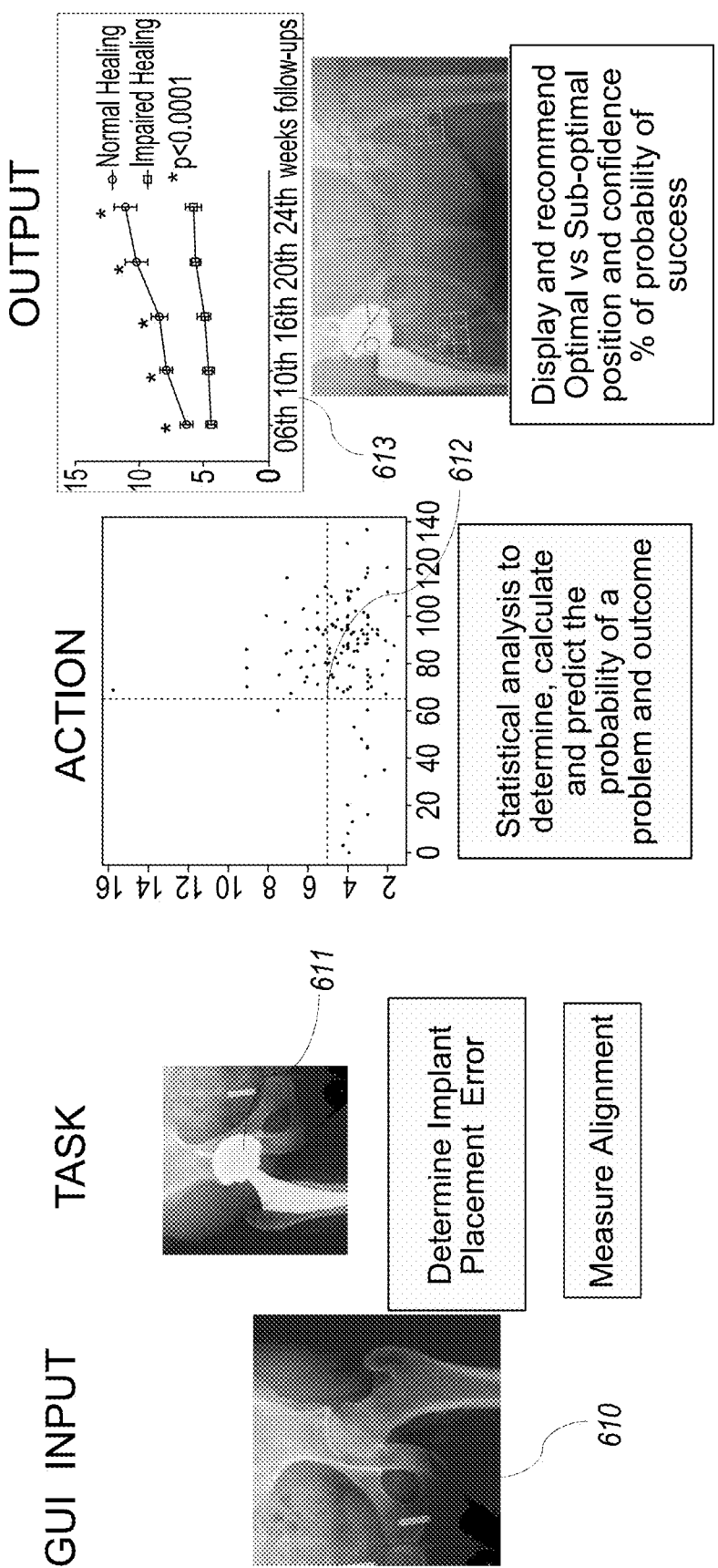

FIG. 23 shows a graphical user interface, user inputs, task and actions relating to problem prediction related to a hip arthroplasty.

Figure 24:
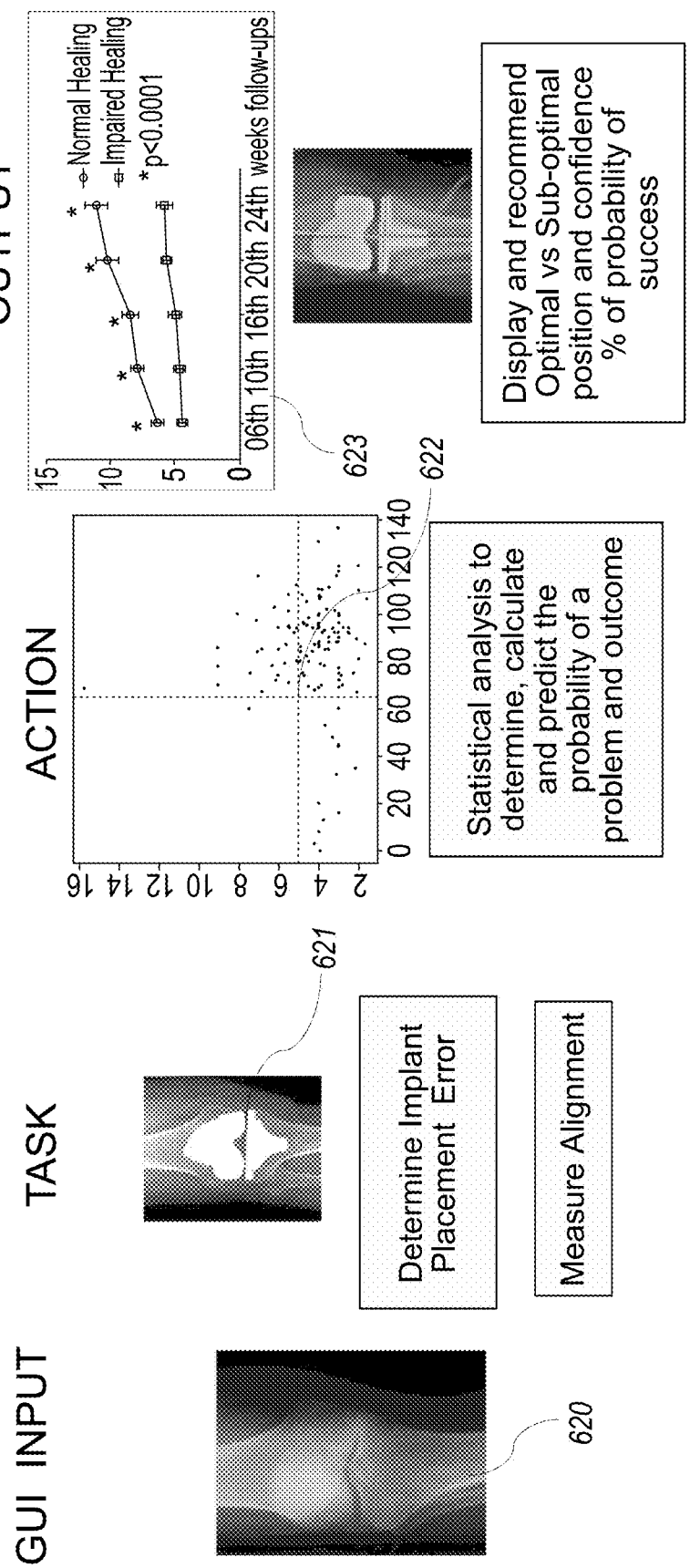

FIG. 24 shows a graphical user interface, user inputs, task and actions relating to problem prediction related to a knee arthroplasty.

Figure 25:
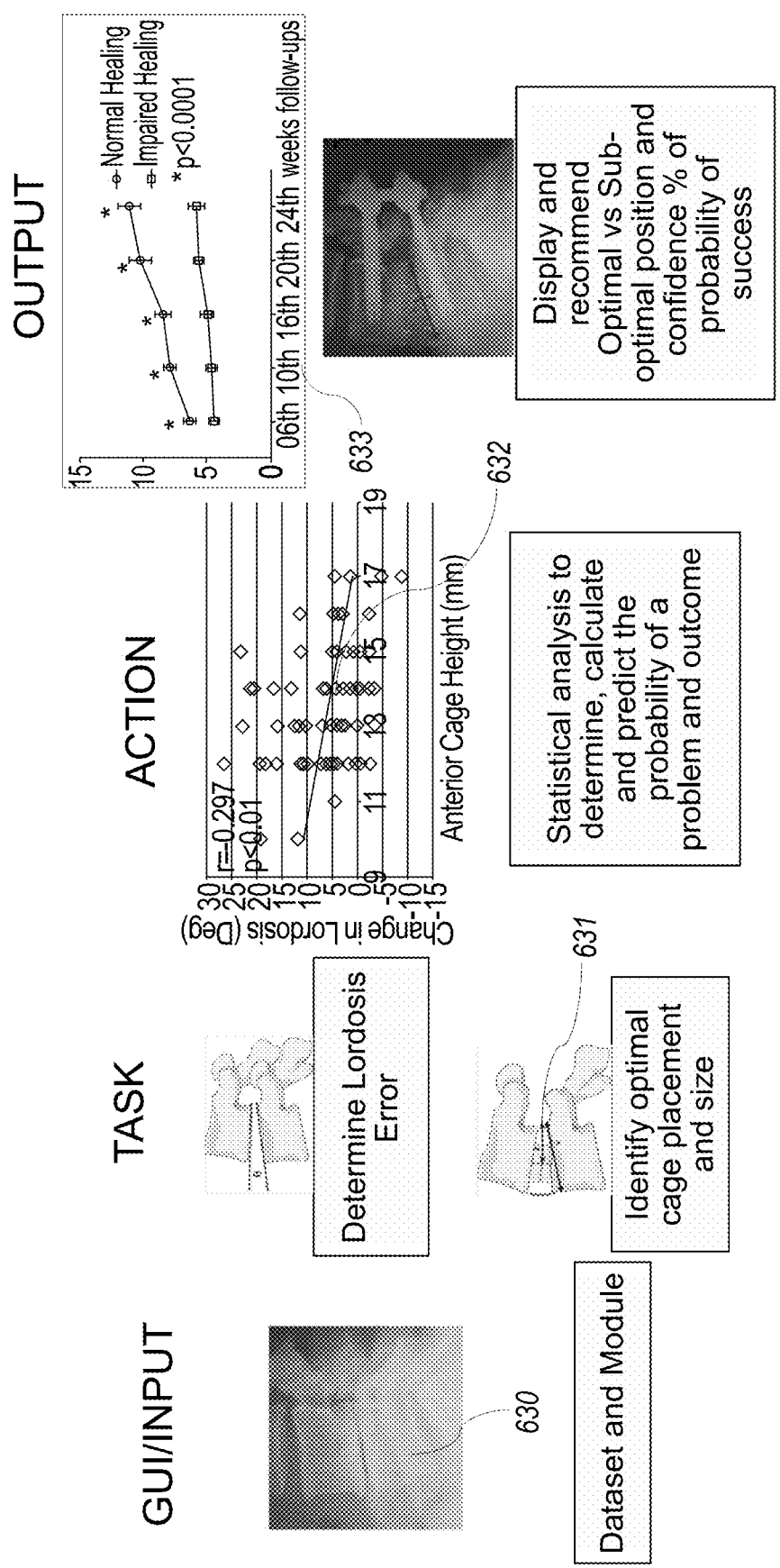

FIG. 25 shows a graphical user interface, user inputs, task and actions relating to problem prediction related to a spine.

Figure 26A:
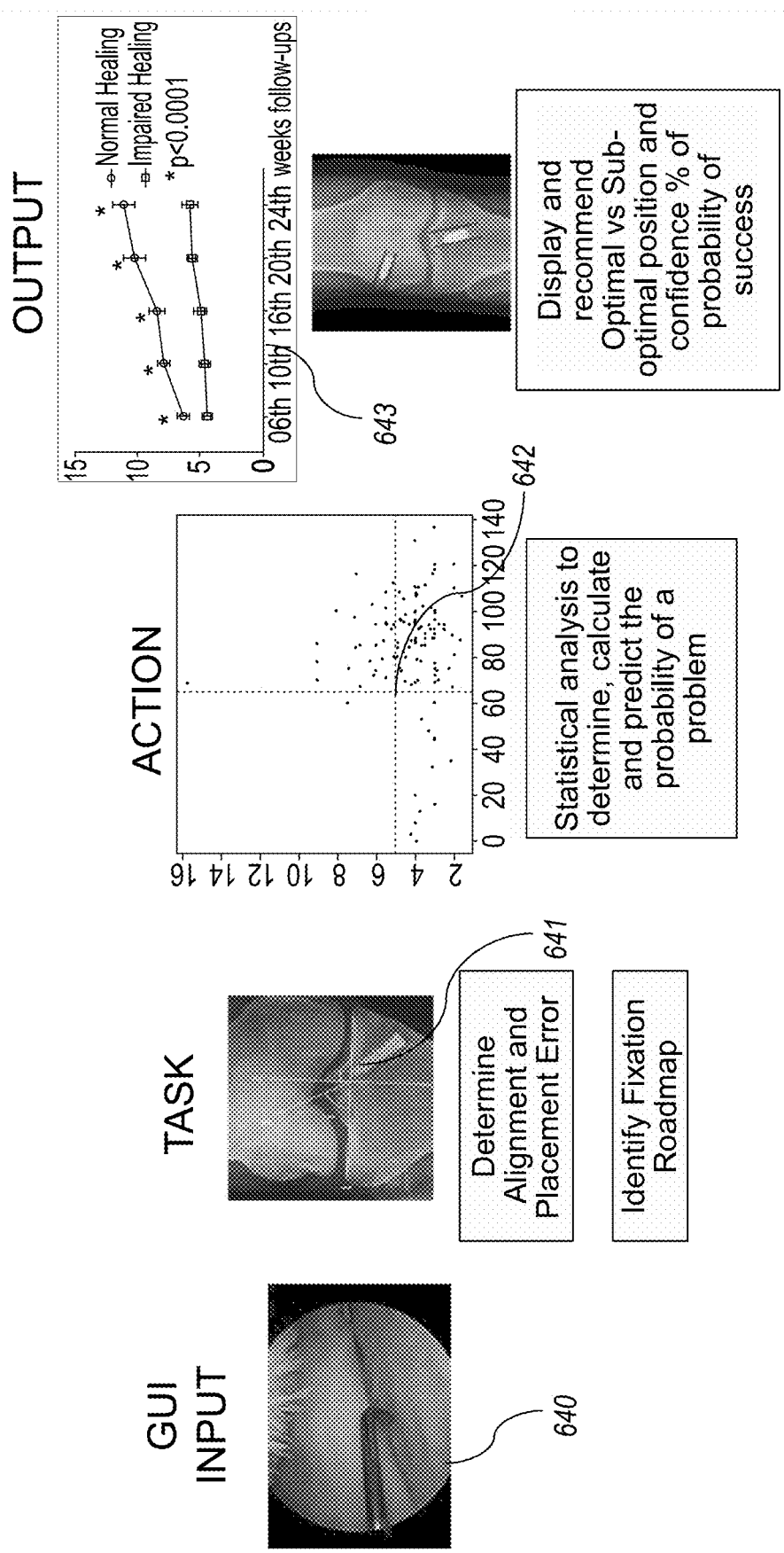

FIG. 26A shows a graphical user interface, user inputs, task and actions relating to problem prediction related to a sports medicine example.

Figure 26B:
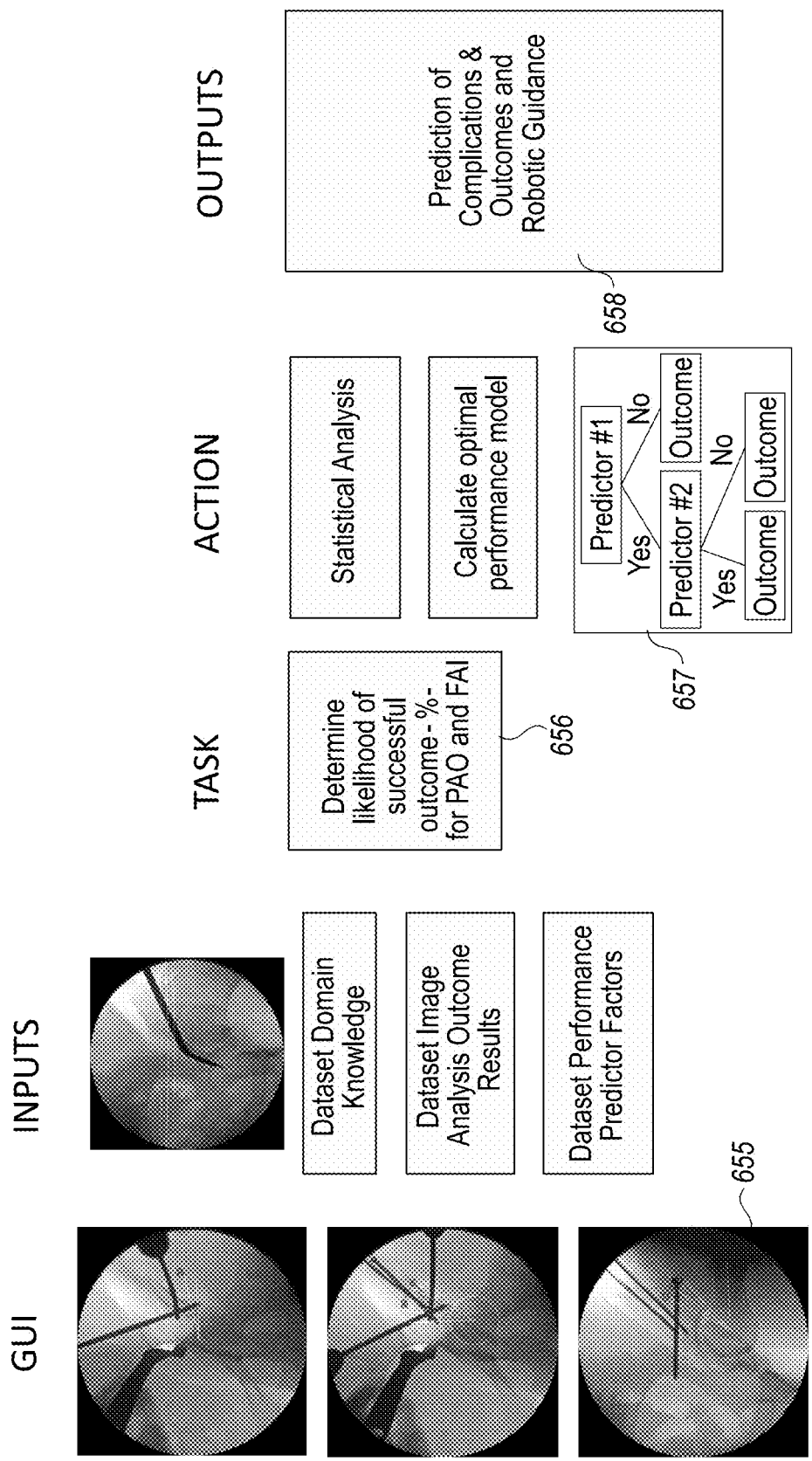

FIG. 26B shows a graphical user interface, user inputs, task and actions relating to problem prediction related to a hip preservation (PAO or FAI) example.

Figure 27:
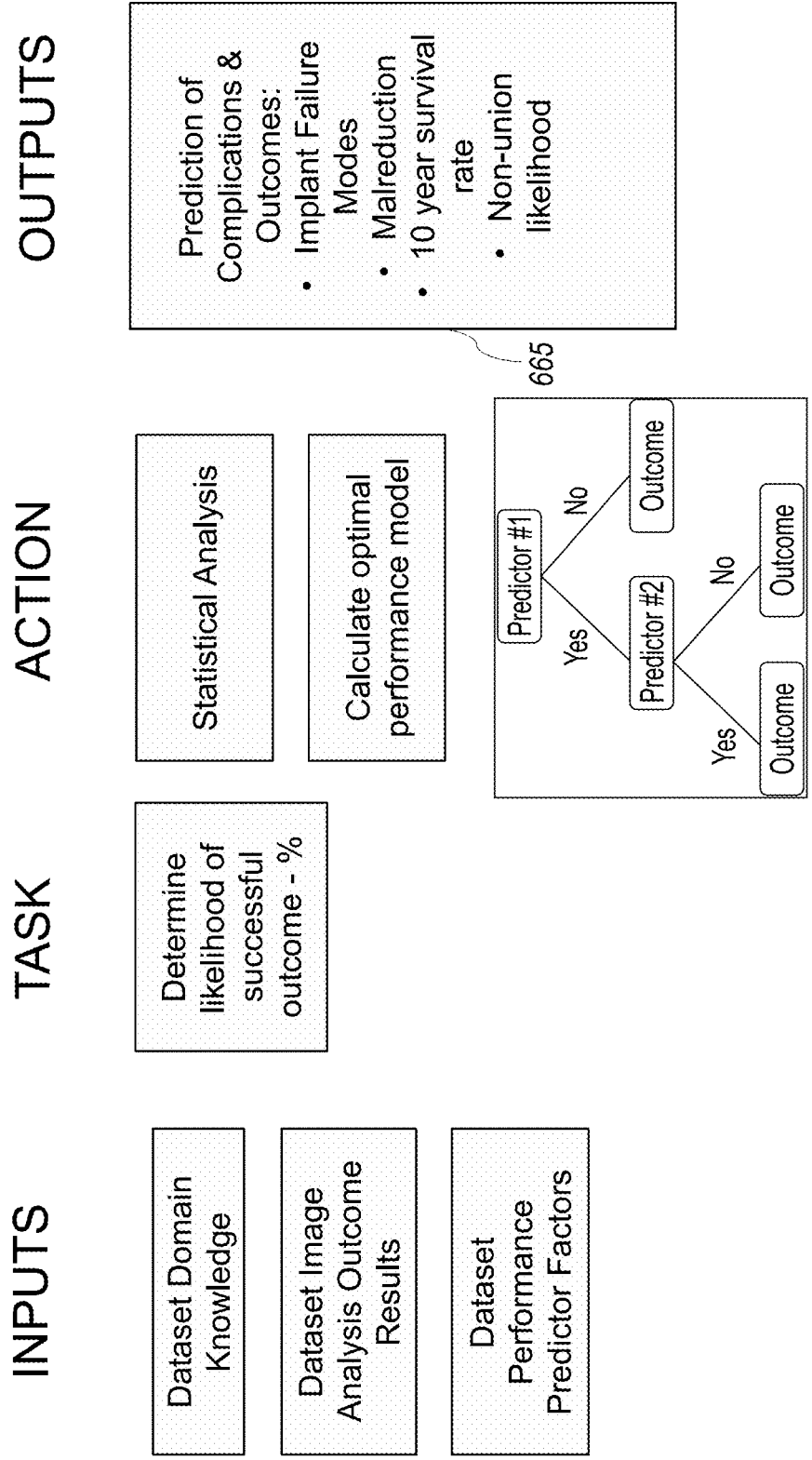

FIG. 27 shows input and output relating to problem prediction.

Figure 28A:
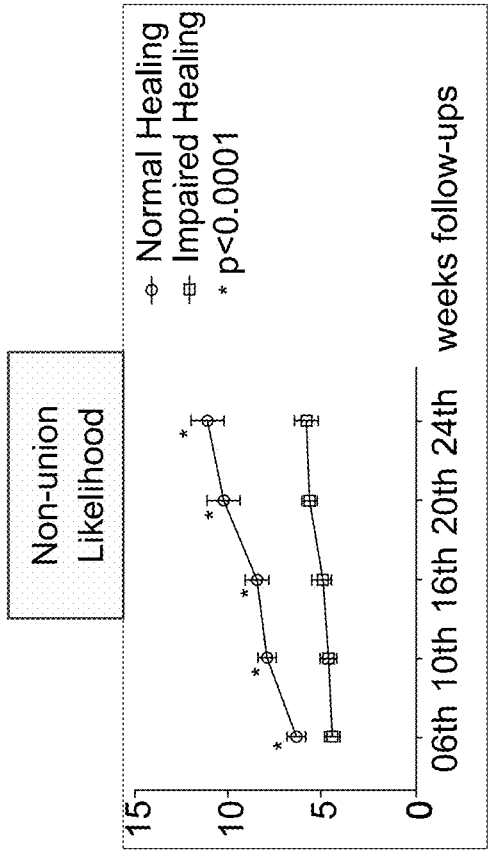

FIG. 28A shows a graphical user interface showing implant and percent performance.

Figure 28B:
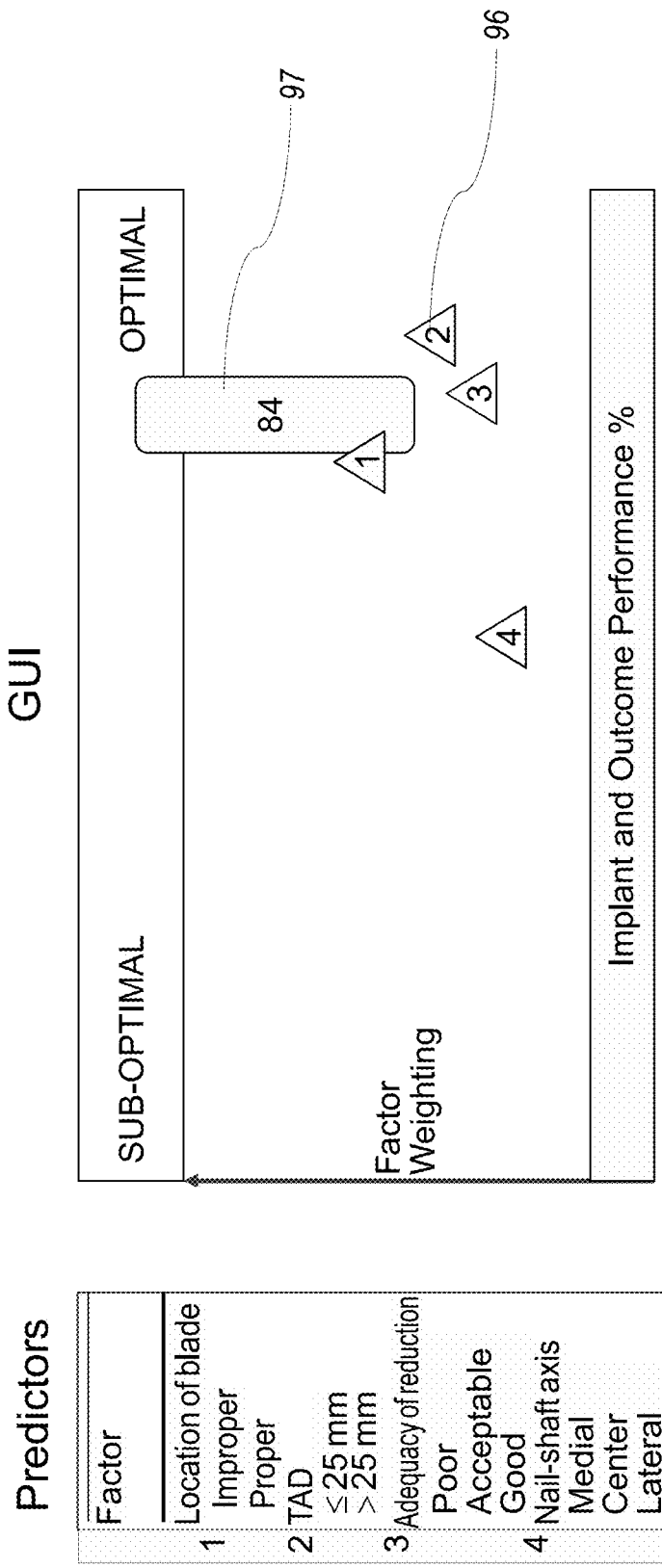

FIG. 28B Graphical interface demonstrating the prediction of an optimal versus sub-optimal outcome.

Figure 28C:
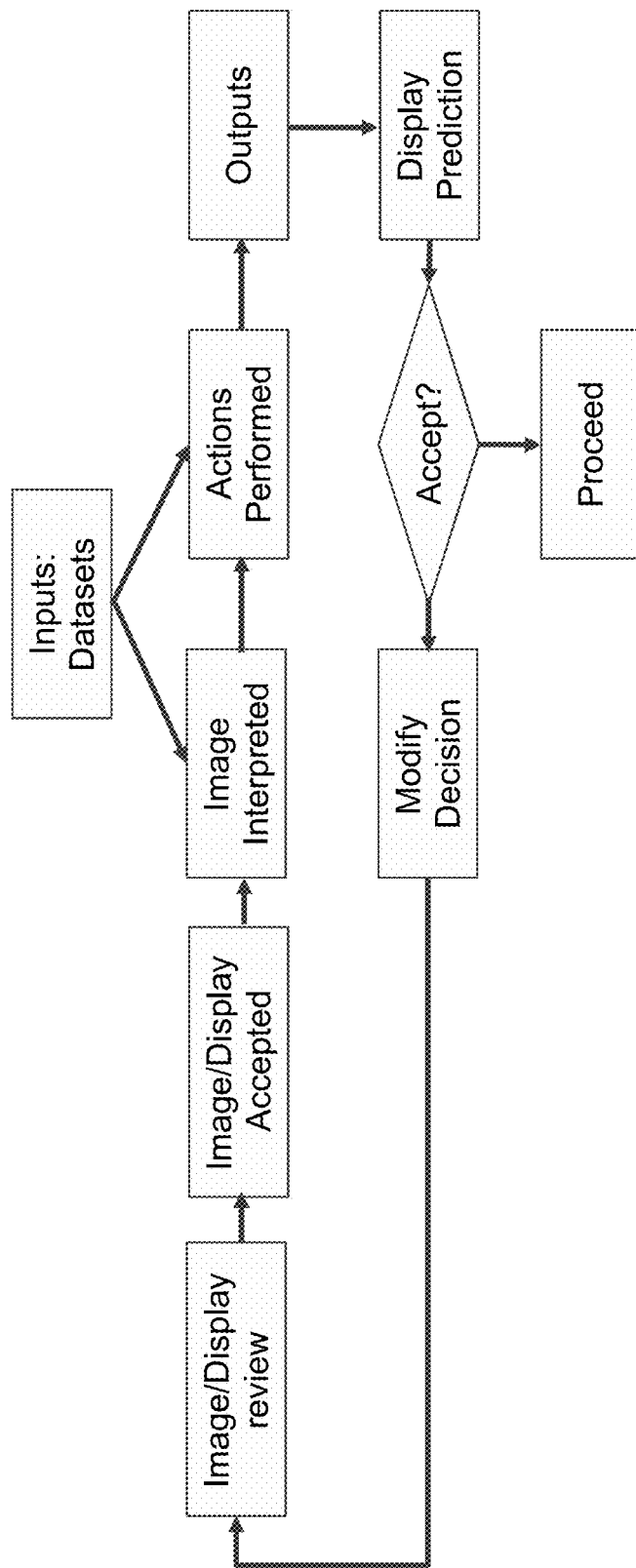

FIG. 28C illustrates a representative example for task workflow demonstrating decision support process with the AI model.

Figure 29:
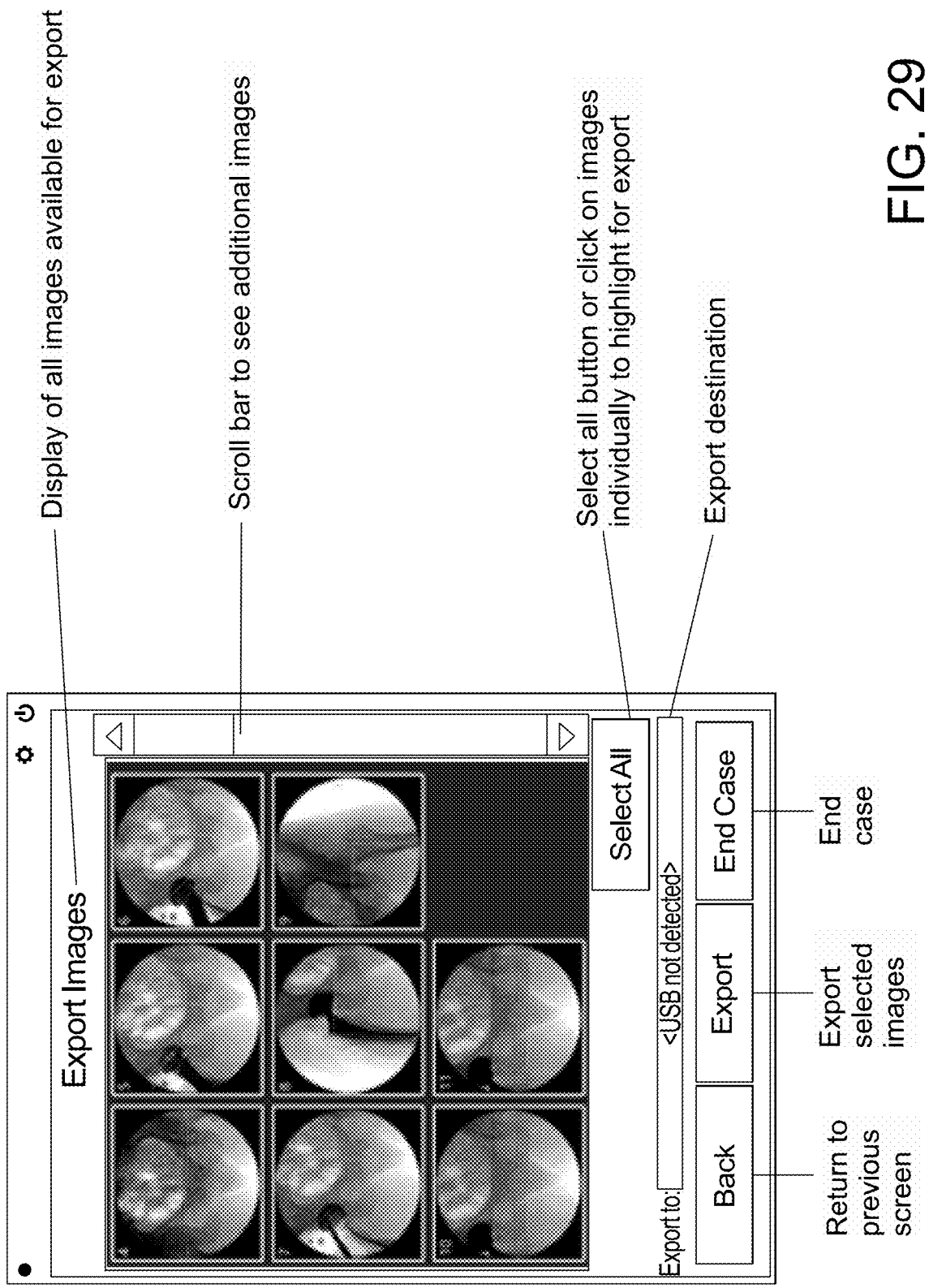

FIG. 29 shows an output relating to image interpretation performed on input images.

Figure 30:
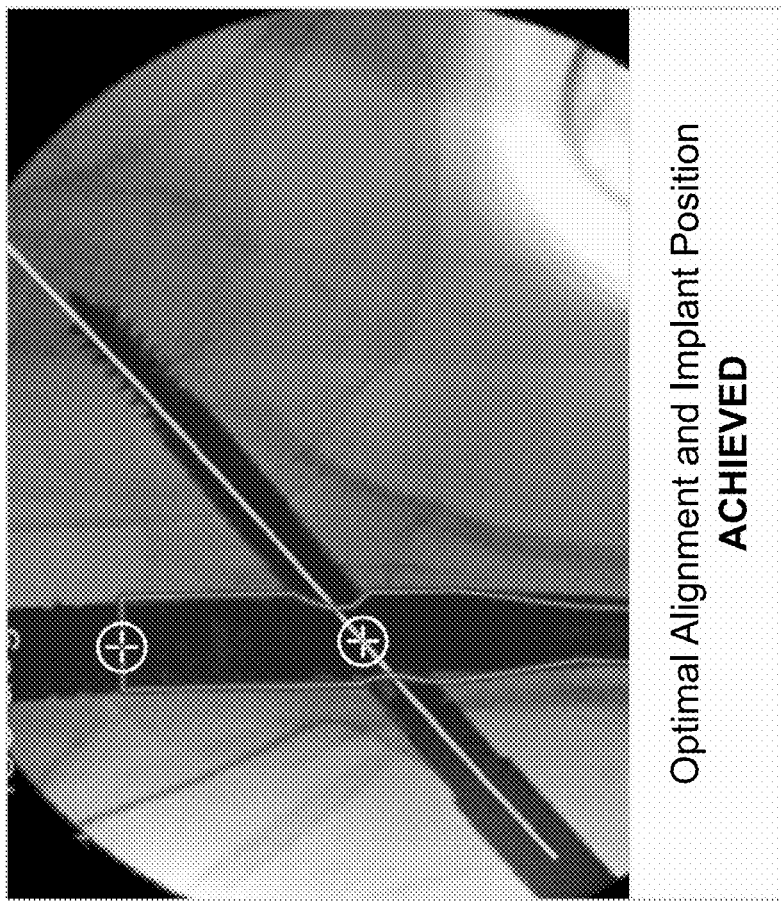
Figure 31:
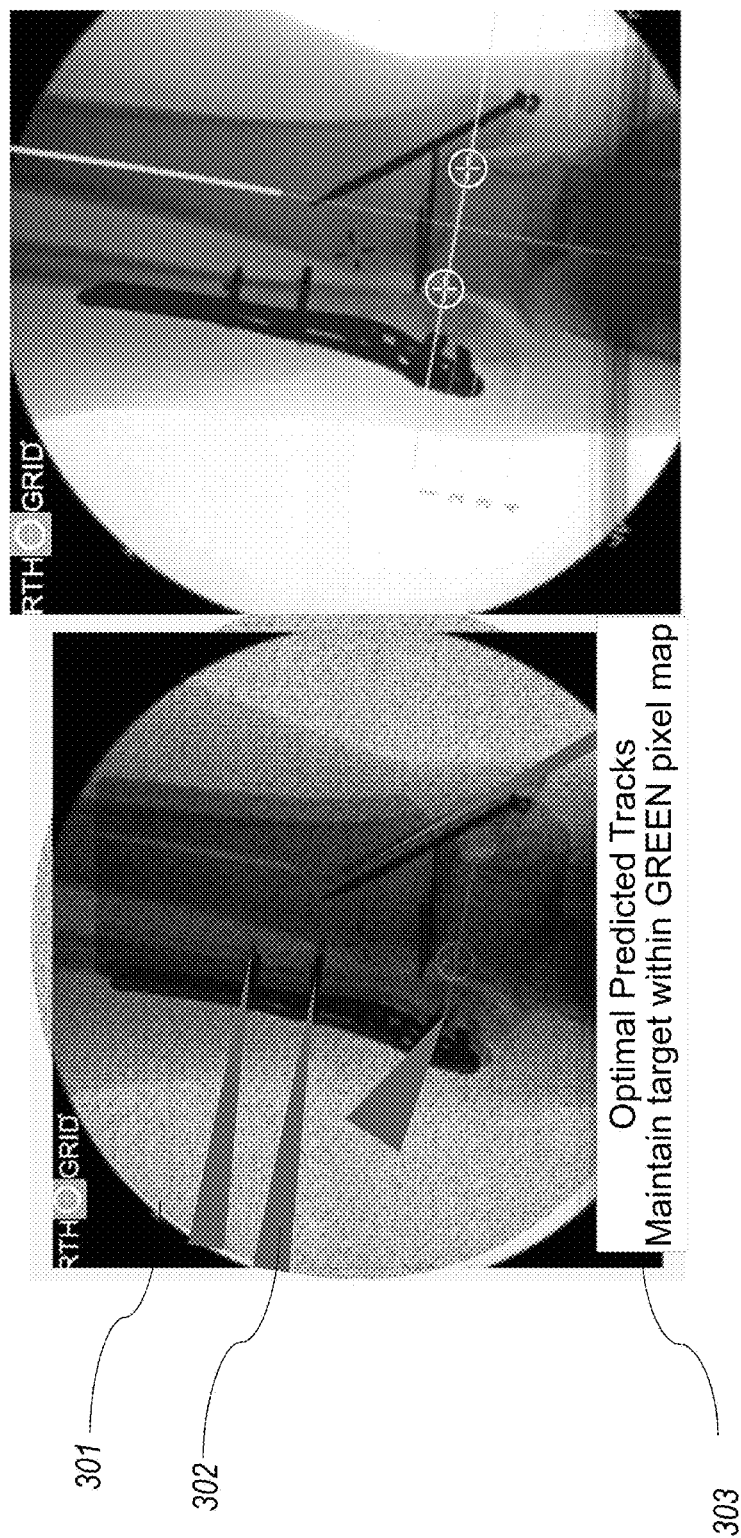

FIG. 30 shows the optimal alignment and Implant position achieved based on image analysis and interpretation FIG. 31 shows a "heat map" where sub-optimal positioning regions on the grid map are indicated in red and optimal positioning regions indicated with green to guide the surgical process.

DESCRIPTION OF EXEMPLARY EMBODIMENTS

The present invention can be understood more readily by reference to the following detailed description of the invention. It is to be understood that this invention is not limited to the specific devices, methods, conditions or parameters described herein, and that the terminology used herein is for describing embodiments by way of example only and is not intended to be limiting of the claimed invention. Also, as used in the specification including the appended claims, the singular forms "a," "an," and "the" include the plural, and reference to a numerical value includes at least that value, unless the context clearly dictates otherwise. Ranges can be expressed herein as from "about" or "approximately" one value and/or to "about" or "approximately" another value. When such a range is expressed, another embodiment includes from the one value and/or to the other value. Similarly, when values are expressed as approximations, by use of the antecedent "about," it will be understood that the value forms another embodiment. All combinations of method or process steps as used herein can be performed in any order, unless otherwise specified or clearly implied to the contrary by the context in which the referenced combination is made. These and other aspects, features and advantages of the invention will be understood with reference to the detailed description herein and will be realized by means of the various elements and combinations particularly pointed out in the appended claims. It is to be understood that both the foregoing general description and the following detailed description of the invention are exemplary and explanatory of preferred embodiments of the inventions and are not restrictive of the invention as claimed. Unless defined otherwise, all technical and scientific terms used herein have the same meaning as commonly understood by one of ordinary skill in the art to which this invention belongs.

The following system and method generally relate to a computing platform having a graphical user interface for displaying subject image data and apply data science techniques such as machine and deep learning to: calculate surgical decision risks, to predict a problem and provide guidance in real-time situations. The system autonomously displays recommended actions through a display such as graphical user interface to provide an optimized implant and subject outcome by calculating the probability of a successful procedural outcome (ex. Implant guidance, fracture reduction, anatomical alignment). The inventive subject matter is directed to an artificial intelligence intra-operative surgical guidance system and method of use. The system in its most basic form included: a computer executing one or more automated artificial intelligence models trained on at least intra-operative surgical images, to calculate surgical decision risks, and to provide an intra-operative surgical guidance, and a visual display configured to provide the intra-operative surgical guidance to a user.

Artificial Intelligence is the ability of machines to perform tasks that are characteristics of human intelligence. Machine learning is a way of achieving Artificial Intelligence. AI is the ability of machines to carry out tasks in an intelligent way. Machine learning is an application of Artificial Intelligence that involves a data analysis to automatically build analytical models. Machine learning operates on the premise that computers learn statistical and deterministic classification or prediction models from data; the computers and their models adapt independently as more data is inputted to the computing system. Misinterpretation of data can lead to mistakes and ultimately a failed outcome. Artificial Intelligence can integrate and infer from a much larger and smarter dataset than any human can discerning patterns and features that are difficult to appreciate from a human perspective. This becomes particularly relevant in the alignment of anatomy and correct placement of implants. The system analyzes and interprets the information and provides guidance based upon a correlation to a known set of patterns and inference from novel sets of data. The artificial intelligence intra-operative surgical guidance system is made of a computer executing one or more automated artificial intelligence models trained on data layer datasets collections to calculate surgical decision risks, and provide intra-operative surgical guidance; and a display configured to provide visual guidance to a user.

Figure 1A:
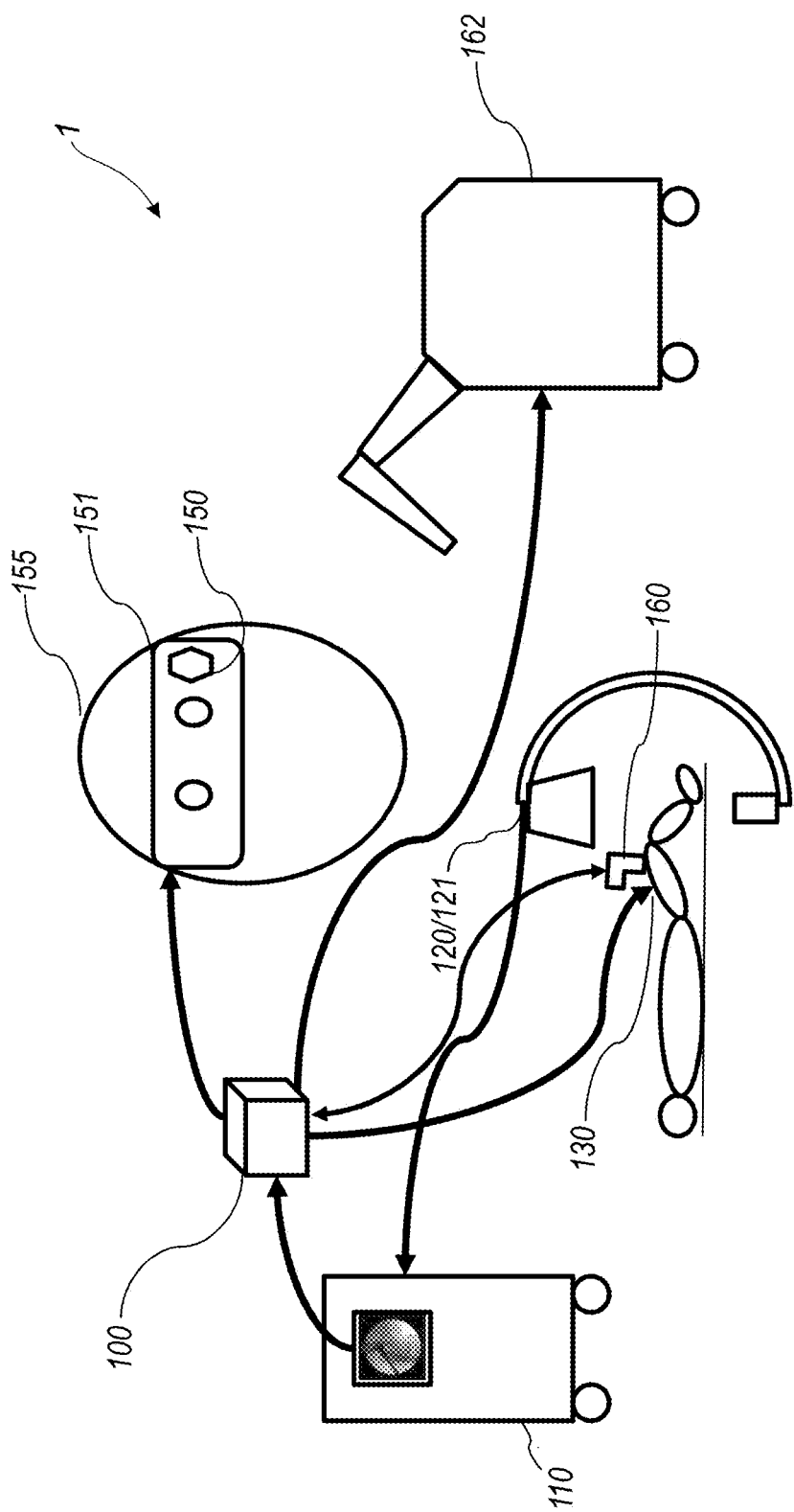
FIG. 1A is a diagram of the system for automated intra-operative surgical guidance.
Figure 1B:
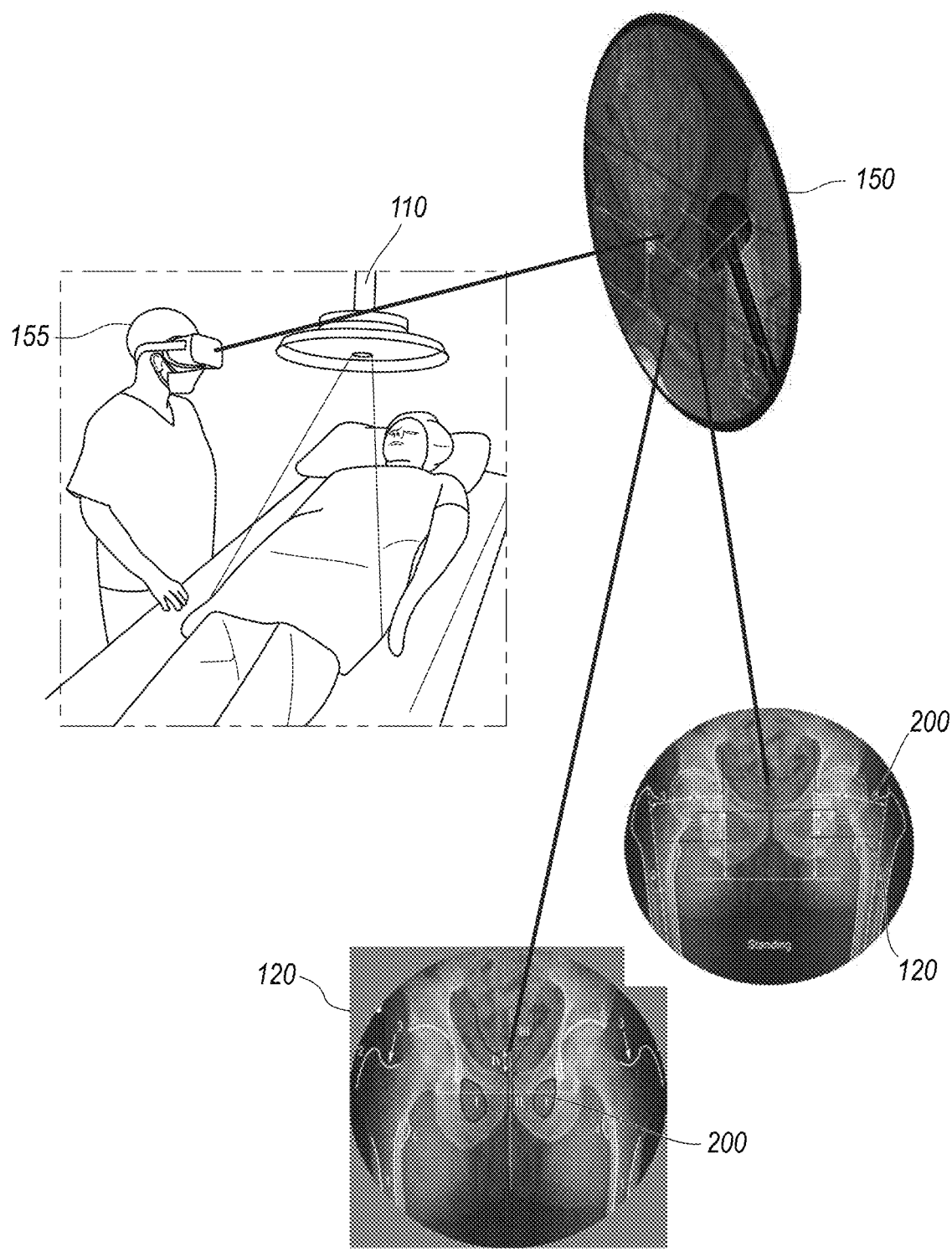
FIG. 1B shows an exemplary view of a head-up display image of the system.

Now referring to FIGS. 1A and 1B, the artificial intelligence intra-operative surgical guidance system 1 includes an imaging system 110. The imaging system 110 receives subject image data such as images 120 (radiographic, ultrasound, CT, MRI, 3D, terahertz) of a subject's anatomy. Exemplary medical images that can be analyzed for intra-operative surgical guidance can include a radiographic image such as an image generated by portable fluoroscopy machine called a C-arm. In some embodiments, the computing platform 100 can be configured to perform one or more aspects associated with automated intraoperative surgical guidance in medical images. For example, computing platform 100 and/or a related module can receive an inter-operative surgical image, e.g., a fluoroscopic image of the knee.

The artificial intelligence intra-operative surgical guidance system 1 includes an input of a series of x-ray or fluoroscopic images of a selected surgical site, a computing platform 100 to process the surgical images and an overlay of a virtual, augmented, or holographic dimensioned grid, with an output to an electronic display device 150. The electronic display device 150 provides a displayed composite image and graphical user interface 151. The graphical user interface 151 is configured to: allow manipulation of a dimensioned grid 200 by a user 155, such as a surgeon, physician assistant, surgical scrub nurse, imaging assistant and support personnel. The computing platform 100 is configured to synchronize with a sensor 130 to (a) provide intraoperative anatomical (for example, bone) or implant positional information; and (b) provide postoperative anatomical or implant or external alignment and correction device information to an Artificial Intelligence Engine for guidance.

The computing platform 100 is configured to synchronize with a surgical facilitator 160 such as a robot or a haptic feedback device 162 to provide the same predictive guidance as described throughout as an enabler for robotic surgery. The computing platform 100 is configured to synchronize with an intelligence guided trackable capable of creating augmented grids or avatars of implants, instruments or anatomy to provide the same predictive guidance as described throughout as an enabler for intelligence guided artificial reality trackable navigation.

The system components include an input of a series of x-ray or fluoroscopic images of a selected surgical site, a dynamic surgical guidance system 1 to process the surgical images and an overlay of a virtual, augmented, or holographic dimensioned grid 200 with an image 120, with an input device to provide manipulation of the dimensioned grid 200 by a user 155, such as a surgeon. In one embodiment, the electronic display device 150 is an electronic display device, such as a computer monitor, or a heads-up display, such as GLASS (Google). In another embodiment, the electronic display screen 150 is a video fpv goggle. An out-put to an electronic display device 150 is provided for the user 155 to image the overlay of the series of images and the dimensioned grid 200.

The augmented reality or holographic dimensioned grid 200 can be manipulated by the user 155 by looking at anatomic landmarks, the shown on the electronic display device 150 that will facilitate locking on the correct alignment/placement of surgical device. The artificial intelligence intra-operative surgical guidance system 1 allows the user 155 to see critical work information right in their field-of-image using a see-through visual display and then interact with it using familiar gestures, voice commands, and motion tracking. The data can be stored in data storage. The artificial intelligence intra-operative surgical guidance system 1 allows the user 155 to see critical work information in their field-of-image using a see-through visual display device 150 and then interact with it using familiar gestures, voice commands, and motion tracking through a graphical user interface 151 such as by an augmented reality controller. The graphical user interface 151, such as augmented reality or holographic dimensioned grid, can be manipulated by the user 155 by looking at anatomic landmarks, then shown on the electronic display device 150 that will facilitate locking on the correct alignment/placement of surgical device.

Figure 2A:
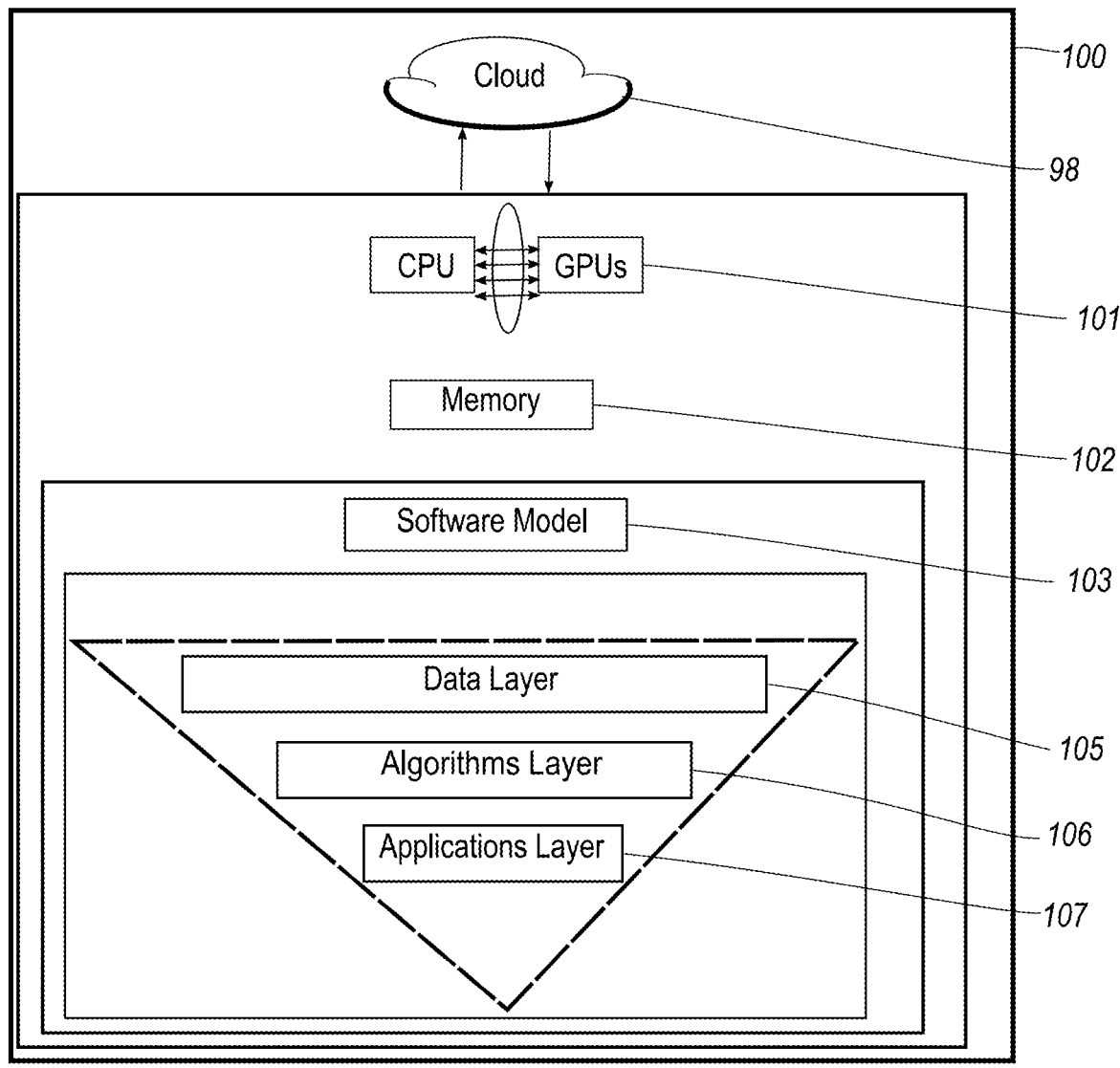
FIG. 2A is a diagram of the computing platform.
Figure 2B:
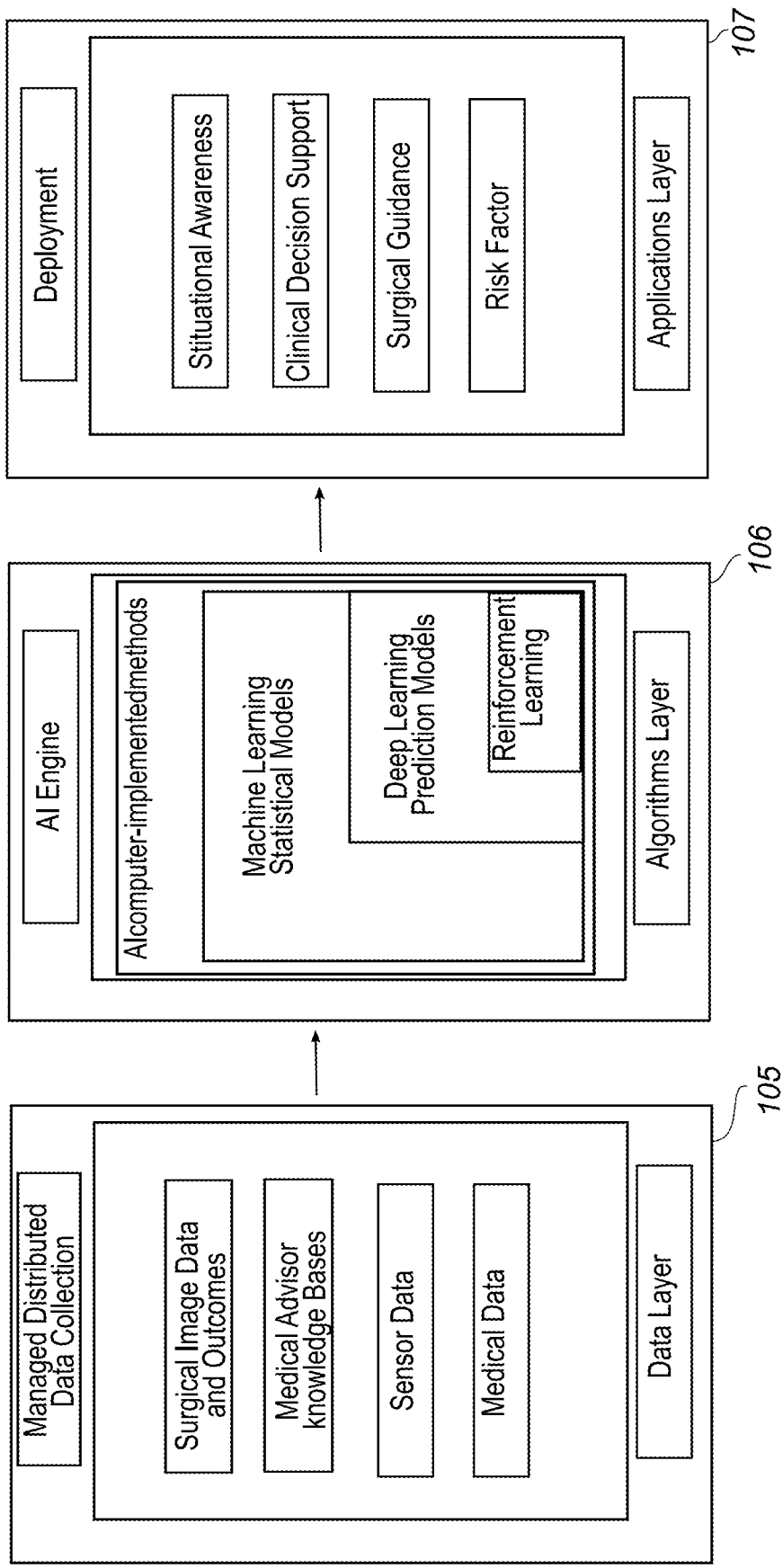
FIG. 2B is a diagram of an artificial intelligence computing system.

FIGS. 2A & 2B are diagrams illustrating an exemplary artificial intelligence surgical guidance system 1 including a computing platform 100 for dynamic surgical guidance according to an embodiment of the subject matter described herein. A computer platform is a system that includes a hardware device and an operating system that an application, program or process runs upon.

The subject matter described herein can be implemented in software in combination with hardware and/or firmware. For example, the subject matter described herein can be implemented in software executed by at least one processor 101. In one exemplary implementation, the subject matter described herein can be implemented using a computer readable medium having stored thereon computer executable instructions that when executed by the processor of a computer platform to perform the steps. Exemplary computer readable media suitable for implementing the subject matter described herein include non-transitory devices, such as disk memory devices, chip memory devices, programmable logic devices, and application specific integrated circuits. In addition, a computer readable medium that implements the subject matter described herein can be located on a single device or computing platform or can be distributed across multiple devices or computing platforms. As used herein, the terms "function" or "module" refer to hardware, firmware, or software in combination with hardware and/or firmware for implementing features described herein.

The computing platform 100 includes at least one processor 101 and memory 102. The computing device can invoke/request one or more servers from the Cloud Computing Environment 98 other clinical metadata can be efficiently retrieved from at least one server from the Cloud Environment if it is sorted in only one server or from separate servers if the dataset was sorted partially in different servers; some outcomes derived from the AI engine can be directly sent and sorted in one or more servers in the Cloud platform (privacy is preserved).

The computing platform 100 analyzes an image for risk factors that the user cannot see due to their human inability to interpret an overwhelming amount of information at any specific moment. If the implant placement and the alignment does not match this data pattern, it will create an awareness in this specific situation and provide a hazard alert to the user. Essentially, identifying and predicting problems ahead of the user encountering them. This can lead to avoidance of complications and prevention of errors. The computing platform 100 includes a plurality of software modules 103 to receive and process medical image data, including modules for image distortion correction, image feature detection, image annotation and segmentation, image to image registration, three-dimensional estimation from two-dimensional images, medical image visualization, and one or more surgical guidance modules that use artificial intelligence models to classify images as predictive of optimal or sub-optimal surgical outcomes. The term dynamic or dynamically means automated artificial intelligence and can include various artificial intelligence models such as for example: machine learning, deep learning, reinforcement learning or any other strategies to dynamically learn. In a trauma event, such as fracture reduction or deformity correction, or in an arthroplasty event such as hip or knee anatomical alignment or bone cut guidance, or in the event of a spine procedure with implant alignment correction, or in a sports medicine event with ACL reconstruction alignment, these surgical procedure specific datasets coupled with domain knowledge that are useful to an event can be accessed. They will be used to interpret critical failure mode factors of an implant or anatomical alignment and combined will provide the user with a Failure Risk Score with the output to the user as a confidence percentage recommendation of a suboptimal or optimal performance metric. This will be presented to the user in the form of intelligent predictors and scores to support decisions encountered in a real time event.

The software module 103 includes a plurality of layers. The data layer 105 is made of a collection of data from various managed distributed data collection networks. This collection of data represents the knowledge that is necessary to address specific tasks. Data layer (detailed in FIG. 2B) is the collection of data which is the input for algorithm layers 106, and it contains data sets from different systems which makes Data layer 105 a rich source information needed for the different deployment tasks. These data layers 105 include surgical image data and related outcomes, medical advisor knowledge base and sensor data.

The algorithm layer 106 includes computer-implemented methods specially designed to target application layer using inputs provided in Data Layer 105. The algorithm layer 106 can also be referred to as an AI engine. The algorithm layer 106 includes various image processing algorithms which use different machine learning techniques (engineering features) and artificial intelligence techniques (hierarchical learning features/learned representation of the features). All algorithms are designed to solve different tasks such as image enhancement, edge detection, segmentation, registration, etc. With the help of Algorithm layer 105, these tasks will be performed automatically, which will contribute to the understating of the high-level complexity of medical data and also to the understanding of dependencies among the data provided in Data Layer. The algorithm layer 106 also includes learning algorithms such as statistical models and prediction models. Representative examples include image quality scoring algorithm, Deep Learning algorithm, Machine Learning based algorithms, and image registration algorithms.

The computing platform 100 is configured to execute one or more automated artificial intelligence models. The one or more automated artificial intelligence models are trained on data from the data layer 105. The data layer 105 includes at least a plurality of surgical images. The artificial intelligence intra-operative surgical guidance system 1 includes a computing platform trained to calculate intra-operative surgical decision risks by applying an at least one classifier. More specifically the computing platform is trained to perform the classification of intra-operative medical images of implants fixation into discrete categories that are predictive of surgical outcomes, for instance, optimal and sub-optimal. The automated artificial intelligence models are trained to calculate intra-operative surgical decision risks and to provide an intra-operative surgical guidance, and a visual display configured to provide the intra-operative surgical guidance to a user. The application layer 107 includes but is not limited to: clinical decision support, surgical guidance, risk factor and other post processing actions such as image interpretation a and visual display.

Now referring to FIGS. 3A & 3B example of automated artificial intelligence models are shown. The computing platform 100 is configured to execute one or more automated artificial intelligence models. These one or more automated artificial intelligence models are trained on data from a data layer 105.

These automated artificial intelligence models include: Deep Learning, machine learning and reinforcement learning based techniques. For example, a Convolutional Neural Network (CNN) is trained using annotated/labeled images which include good and bad images to learn local image features linked to low-resolution, presence of noise/artifact, contrast/lighting conditions, etc. The CNN model uses the learning features to make predictions about a new image. The CNN model can include a number of conventional layers and a number of pooling layers which proceed to subsampling (or down sampling) of each feature map while retaining the most informative feature. The stack of the layers can include various Conventional Kernels of size N×M; N and M are positive integers and stand respectively for Kernel width and height.

FIG. 3A illustrates a deep learning model architecture. The AI deep CCN architecture shown in FIG. 3A is for the classification for surgical outcomes (optimal vs suboptimal) with a score quantifying this classification using Convolutional Neural Networks. This architecture comprises several (deep) layers involving linear and non-linear learnable operators which enable building high-level information making the process of construction of discriminative information automated. The first input layer of the deep learning network learns how to reconstruct the original dataset which is the collection of data layer 105. The subsequent hidden layers learn how to reconstruct the probability distributions of the activations of the previous layer. The number of the hidden layers define the depth level of the deep learning architecture. The output layer of a neural network is tied to the overall task.

As illustrated in the figure FIG. 3A, the classification CNN provides an output probability score for surgical outcome. This score quantifies the quality of positioning of an implant and/or bone alignment. CNN hyperparameters including the number of layers as well as the filter sizes were derived empirically upon testing the performance of the designed network on data collection from Data Layer. The CNN architecture is adjustable in a way to provide high sensitivity detection for the positioning of the implant.

FIG. 3B is a schematic illustration of multi-scale reinforcement leaning (RL) as applied to the task of intraoperative screw insertion. This type of reinforcement learning can intraoperatively illustrate insertion trajectory and pedicle screw trajectories.

Now referring to FIGS. 4A-4B, the software is organized into modules and each module has at least one function block as shown in this figure. The non-transitory computer-readable storage medium is coupled to a microprocessor, wherein the non-transitory computer-readable storage medium is encoded with computer-readable instructions that implement functionalities of the following modules, wherein the computer-readable instructions are executed by a microprocessor.

The computing platform 100 of the artificial intelligence intra-operative surgical guidance system 1 can include the following modules. Module 5 is made of an image quality scoring algorithm to assess the quality of an acquired medical image for its intended use. The image quality scoring algorithm is an image processing algorithm that is based on Machine Learning or Deep Learning from a good and bad medical image training dataset for a specific application. For Machine Learning based algorithms, image quality score of a given image is computed based on quality metrics which quantify the level of accuracy in which a weighted combination of technical image factors (e.g., brightness, sharpness, etc.) relate to how clearly and accurately the image captures the original anatomical structures of an image. These weighed combinations of factors are known predictors of optimal or sub-optimal outcomes or performance measures. Examples: "adequacy of reduction" (FIG. 28B). The weighted combination of technical factors is a parametrized combination of key elements which quantify how good the image is. It can be seen as an indicator of relevancy of the image, and determines if the acquired image is sufficient to work with or not. In this invention, it is used to define the quality metric/image score For Deep Learning based techniques, a Convolutional Neural Network (CNN) is trained using annotated/labeled images which include good and bad images to learn local image features linked to low-resolution, presence of noise/artifact, contrast/lighting conditions, etc. The CNN model uses the learning features to predict, for a new image, its image quality score.

As can be seen in FIG. 3A, the CNN model can include a number of conventional layers and a number of pooling layers which proceed to subsampling or down sampling of each feature map while retaining the most informative feature. The stack of the layers can include various Conventional Kernels of size N×M; N and M are positive integers and stand respectively for Kernel width and height. Module 5 maximizes the performance of further computer vision and image processing tasks. Module 5 can also include a grid-based pose guide to assist the user in acquisition of a better image as appropriate to the application.

Module 6 includes one or more algorithms to detect and correct for distortion inherent in medical imaging modalities, for example the fluoroscopic distortion inherent in intraoperative C-arm imaging.

Module 7 is an image annotation module that includes image processing algorithms or advanced Deep Learning based techniques for detecting anatomical landmarks in a medical image and identifying contours or boundaries of anatomical objects in a medical image, such as bone or soft tissue boundaries. Anatomical Landmark detection stands for the identification of key elements of an anatomical body part that potentially have a high level of similarity with the same anatomical body part of other patients. The Deep Learning algorithm encompasses various conventional layers and its final output layer provides self-driven data, including, but not limited to, the system coordinates of important points in the image. In the current invention, landmark detection can be also applied to determine some key positions of anatomical parts in the body, for example, left/right of the femur, and left/right of the shoulder. The Deep Neural Network output is the annotated positions of these anatomical parts. In this case, the Deep Learning algorithm uses a training dataset which needs to meet some requirements: the first landmark in the first image used in the training must be consistent across different images in the training dataset. Identifying contours of anatomical objects refers to providing an edge map consisting of rich hierarchical features of an image while preserving anatomical structure boundaries using Deep Learning techniques. A variety of highly configurable Deep Learning architectures with an optimized hyperparameters tuning are used to help with solving specific tasks. The trained Conventional Neural Network in one embodiment includes tuned hyperparameters stored in one or many processor-readable storage mediums and/or in the Cloud Computing Environment 98.

Module 8 is a preoperative image database including computer algorithms and data structures for storage and retrieval of preoperative medical images, including any metadata associated with these images and the ability to query those metadata. Preoperative images can include multiple imaging modalities such as X-ray, fluoroscopy, ultrasound, computed tomography, terahertz imaging, or magnetic resonance imaging and can include imagery of the nonoperative, or contralateral, side of a patient's anatomy.

Module 9 is the Image Registration which includes one or more image registration algorithms.

Module 10 is composed of computer algorithms and data structures for the reconstruction and fitting of three-dimensional (3D) statistical models of anatomical shape to intraoperative two-dimensional or three-dimensional image data. Module 11 is composed of image processing algorithms and data structures for composing multiple medical images, image annotations, and alignment grids into image-based visualizations for surgical guidance.

Module 12 is an Artificial Intelligence Engine that is composed of image processing algorithms based on Machine and/or Deep Learning techniques for the classification of intraoperative medical images of reduction and alignment procedures into discrete categories that are predictive of differing surgical outcomes, such as suboptimal or optimal outcomes. Classifications produced by Module 12 can also include an associated score that indicates a statistical likelihood of the classification and is derived from the model underlying the image classifier algorithm, i.e a classifier.

Module 13 is an Artificial Intelligence Engine that is made of image processing algorithms which uses Machine Learning or Deep Learning methods for the classification of intraoperative medical images of implant fixation procedures into discrete categories that are predictive of differing surgical outcomes, such as suboptimal or optimal. Classifications produced by Module 13 can also include an associated score that indicates a statistical likelihood of the classification and is derived from the model underlying the image classifier algorithm.

Module 14 is a postoperative image database made of computer algorithms and data structures for storage and retrieval of postoperative medical images, including any metadata associated with these images and the ability to query those metadata. Postoperative images can include images acquired during routine follow-up clinic visits or surgical revisions.

Module 15 is an Artificial Intelligence Engine that is made of image processing algorithms for the classification of a time series of postoperative medical images into discrete categories that are predictive of differing surgical outcomes, such as suboptimal or optimal outcomes. Classifications produced by Module 15 can also include an associated score that indicates a statistical likelihood of the classification and is derived from the model underlying the image classifier algorithm.

Module 16 is a fracture identification and reduction module with access to an AO/OTA Classification Dataset interprets the image and makes a classification of the bone, bone section, type and group of the fracture.

Now referring to FIG. 2B, the computing platform 100, which includes one or more Artificial Intelligence (AI) Engines, including FIG. 4A, Modules 12, 13, and 15, and information from a series of datasets. Here deep neural networks and other image classifiers are trained to analyze and interpret visual features in one or more images to anticipate problems and predict outcomes in a surgery or in a postoperative follow-up period. Training relies on one or more medical image datasets with associated known outcomes data. A trained neural network in this context can thus be thought of as a predictive model that produces a surgical outcome classification from an input set of medical image features.

The outcome classification is typically also accompanied by a statistical likelihood that the classification is correct. Together, the classification and its likelihood can be thought of as an outcome prediction and a confidence level of that prediction, respectively. In the case of a suboptimal outcome prediction, we can consider the confidence level to be a Failure Risk Score for a suboptimal outcome. The classification and Failure Risk Score can thus be used by the surgeon to support decisions that lead to optimal outcomes and avoid suboptimal outcomes. Any number of classical machine learning approaches can be used, as well as more modern Deep Learning networks [LeCun, Yann, Yoshua Bengio, and Geoffrey Hinton. "Deep learning." nature 521.7553 (2015): 436], such as Convolutional Neural Networks [e.g. Lawrence, Steve, et al. "Face recognition: A convolutional neural-network approach." IEEE transactions on neural networks 8.1 (1997): 98-113.] A surgical outcomes classifier with a confidence score can also be constructed using any number of methods in multivariate statistics, including a Cox proportional hazards model or other common regression-based time-to-failure models constructed from clinical research data. In the case of a classifier constructed using a multivariate statistical model, the inputs include at least in part feature sets derived from the medical image data. For instance, in order to identify surgical outcomes using "non-image" datasets, for example diagnosis reports derived from datasets (e.g. "Dataset Outcomes Surgical Variables" in FIG. 4B), Natural Language Processing (NPL) can be used to process clinical text data.

The systems and methods describe uses for the artificial intelligent platform, such as the ability to read and interpret subject image data, and calculate surgical decision risks, and provide the end user with a confidence score of the probability of an optimal outcome and predictor of performance metrics for implants and surgical factors. This occurs by dynamically updating, by the computing platform, the composite image with the at least one surgical guidance.

The computing platform 100, which includes an artificial intelligence engine, utilizes and analyzes the information from the datasets. These information sets have been analyzed and structured and based upon the specific surgical application can include: procedural medical image datasets, such as intraoperative fluoroscopic images and pre- and postoperative x-ray, MRI or computed tomography data; an AO/OTA Danis-Weber fracture classification dataset; Lauge-Hansen classification system dataset; implant 3D CAD model datasets, biomechanical testing such as Von Mises Stresses failure modes datasets; medical image feature datasets and learned models for anatomical feature tracking; best-pose grid datasets; fracture reduction image datasets with associated outcomes data; other surgical outcomes datasets: peer-reviewed literature and clinical studies datasets; known predictors and indicators of complications datasets; 3D statistical models of human anatomy datasets; other medical image datasets; an expert physician domain knowledge datasets; bone quality index datasets; failure risk score datasets; subject HER information data; and outcomes surgical variables datasets such as trauma outcomes data, arthroplasty outcomes scoring data, ACL outcome rating scales, and spine scoring systems.

In addition to these surgical and procedure specific datasets, information from subject health records such as comorbidity data, the presence of deformity, and bone quality index scores can be accessed. These datasets are configured to include information that will potentially have an impact on the outcome of the procedure. The datasets are used to interpret critical failure mode factors of an implant or anatomical alignment and when used to train an outcomes classifier for an Artificial Intelligence Engine provides the user with a prediction of optimal or suboptimal outcome and an associated Failure Risk Score. The AI engine include multiple CNNs based classifiers which can be selected using the specific dataset (one or more dataset, most importantly uncorrelated data that make the CNN learn new relevant features) from Data Layer for solving a well-defined task, for example, determine the position of implants, etc.

The information from independent datasets can be accessed at any given time, or alternatively a situation during the event can require the input from various datasets simultaneously. In this situation information from the relevant datasets will be selected for inclusion in the Artificial Intelligence (AI) Engine in the form of multiple trained classifiers, each with a weighted contribution to the final surgical outcome prediction. In this case, Machine and/or Deep Learning techniques are intended to identify relevant image features from input space of these datasets and the AI Engine seeks an individual customized software solution to a specific task, for example a decision regarding implant positioning or surgical guidance, and datasets involved to solve that task. This multiple prediction model utilizes information from datasets that have a relationship from the perspective of sharing uncorrelated or partially correlated predictors of a specific outcome. The AI Engine can further weight the outcome prediction data based upon the relative level of criticality regarding performance or failure. The model outputs decision support and outcome predictions for example the probability of a successful and optimal long-term outcome.

The computing platform 100 is configured to synchronize with a Computer Assisted Surgery (CAS) system to provide the same predictive guidance as described throughout as an enabler for computer assisted surgery. The dynamic surgical guidance system 1 described herein, has the capability to provide predictive guidance or act as an enabler for subject specific, or custom, matched-block guided technology. For example, the present invention can be applicable to other musculoskeletal applications such as arthroplasty surgery for hip, knee, ankle and shoulder as well as trauma surgery for musculoskeletal repair and for spine applications. Typical applications include hip, knee, shoulder, elbow, and ankle arthroplasty, trauma fractures and limb deformity correction, spine, and sports medicine procedures such as femoroacetabular impingement/(FAI)/Periacetabular Osteotomy (PAO). The artificial intelligence intra-operative surgical guidance system 1 is configured to implement a method including the steps of: obtaining subject image data; dynamically displaying the subject image data on a graphical user interface; selecting an anatomical structure within the subject image data and mapping a grid template to the anatomical structure to provide a registered image data; providing an artificial intelligence engine and at least one dataset configured to generate surgical guidance; providing as a data output, the registered image data, to the artificial intelligence engine to generate at least one surgical guidance; and dynamically updating, by the computing platform, the composite image of the registered image data with the at least one surgical guidance. The surgical guidance is related to: deformity correction, an anatomy alignment, a fracture reduction and an anatomy reduction. The process of surgical guidance will be discussed in the following section for these applications. The method further includes the step of generating a trackable location and orientation guided by the grid template. These steps will be more fully described as they are implemented in FIGS. 5A-31.

Now referring to FIGS. 4A, & 5A-5C, an over image of the use of an artificial intelligence engine and the data sets applied to registered pre-, intra-, and postoperative images yields a graphical user interface for use in reduction and alignment and implant fixation procedures. The preoperative workflow is provided. The workflow proceeds as follows. The imaging system 110 of the artificial intelligence intra-operative surgical guidance system 1 receives subject image data such as one or more preoperative images and computes an image quality score using Image Quality Scoring and Pose Guide Module 5. The user is presented with a choice to either accept or reject the image based on the image quality score and pose guide guidance. If the image is rejected, the operator tries again to acquire an acceptable image. If accepted, distortion in the image is detected and corrected using the Distortion Correction Module 6. The image is then annotated with anatomical landmarks and image segmentations using the Image Annotation Module 7. Images are then stored for later use in the intraoperative and postoperative workflows via the Preoperative Image Database Module 8. The process is then repeated to acquire any number of images necessary for later reference in the intraoperative and postoperative workflows.

Now referring to FIGS. 4A & 5B, the intraoperative workflow is provided. The process proceeds as follows. The artificial intelligence intra-operative surgical guidance system 1 receives one or more preoperative images and computes an image quality score using Image Quality Scoring and Pose guide Module 5. The user is presented with a choice to either accept or reject the image based on the image quality score and pose guide guidance. If the image is rejected, the operator tries again to acquire an acceptable image. If accepted, distortion in the image is detected and corrected using the Distortion Correction Module (6). The image is then annotated with anatomical landmarks and image segmentations using the Image Annotation Module 7. The artificial intelligence intra-operative surgical guidance system 1 then registers the image to the best matching corresponding image in Preoperative Image Database module 8 and computes a matching score using the Image Registration Module 9. The user accepts or rejects the image and registration based on the registration match and quality score. If accepted, three-dimensional anatomical shape information can be computed using the 3D Shape Modeling Module 10 followed by a registration (mapping) of an alignment grid to annotated image using the Image Registration Module 9.

The step of registration is the process of transforming images of preoperative of nonoperative side (the fixed image, f(x),) and intraoperative of the operative side (the current moving image, m(x),) to a common coordinate system so that corresponding pixels represent homologous biological points. This means recovering the transform, T(x), which maps points in f(x) to m(x). This is accomplished by the steps of: (1) define the transformation model, (2) determine the similarity metrics describing the objective function to be minimized, and (3) the optimization algorithm that solves the minimization problem. The effective alignment of these images will allow the surgeon to highlight different characteristics and therefore establish a better comparison of these images. It should be noted that the images that are registered do not have to be imaged from the same modality; it can be MRI to CT or CT to CT, and so on.

The computing platform 100 of the artificial intelligence intra-operative surgical guidance system 1 produces a composite image or images for display to the user using any combination of the current acquired image, the aligned preoperative image, the registered alignment grid using the Image Composition Module 11. Here different processes are followed depending on the type of procedure. For reduction & alignment, the system computes an outcome classification and Failure Risk Score using the Reduction and Alignment Outcomes Prediction Module 12. For implant fixation, the system computes an outcome classification and Failure Risk Score using the Implant Fixation Outcomes Prediction Module 13.

The artificial intelligence intra-operative surgical guidance system 1 then annotates the displayed composite image and graphical user interface with the outcome classification and Failure Risk Score, along with any surgical guidance information. Surgical guidance directives can then be communicated to a surgical facilitator 160 such as a haptic feedback device, a robot, a trackable guide such as tracked Implant or object, a cutting block, a computer assisted surgery device, IoT device and a mixed reality device.

Now referring to FIGS. 4A & 5C, the postoperative workflow is provided. The process proceeds as follows. The artificial intelligence intra-operative surgical guidance system 1 receives one or more postoperative images and computes an image quality score using Image Quality Scoring and Pose guide Module (5). The user is presented with a choice to either accept or reject the image based on the image quality score and pose guide guidance. If the image is rejected, the operator tries again to acquire an acceptable image. If accepted, distortion in the image is detected and corrected using the Distortion Correction Module 6. The image is then annotated with anatomical landmarks and image segmentations using the Image Annotation Module 7. The artificial intelligence intra-operative surgical guidance system 1 then registers the image to all preceding time series images in the Postoperative Image Database 14 and computes matching scores using the Image Registration Module 9. The user accepts or rejects the image and registration based on the registration match and quality score. If accepted, three-dimensional anatomical shape information can be computed using the 3D Shape Modeling Module 10, followed by a registration (mapping) of an alignment grid to annotated image using the Image Registration Module 9.

The artificial intelligence intra-operative surgical guidance system 1 produces a composite image or images for display to the user using any combination of the current acquired image, the aligned preoperative image, the registered alignment grid using the Image Composition Module 11. The system then computes an outcome classification and Failure Risk Score using the Postoperative Outcomes Prediction Module 13. The artificial intelligence intra-operative surgical guidance system 1 then annotates the displayed composite image and graphical user interface with the outcome classification and Failure Risk Score, along with any guidance information.

Now referring to FIG. 6, the subject is prepared and positioned for a medical or surgical event in a standard manner as indicated for the specific procedure, for example, joint replacement, orthopedic trauma, deformity correction, sports medicine, and spine. The preoperative image 115 or data is imported and is shown as FIG. 6. The preoperative image 115 shows a grid template 200 super imposed over the subject's anatomical image.

A grid template 200 has a plurality of dimensioned radio-opaque lines, e.g. 230 relating to surgical variables. The portion of the grid template 200 that is not opaque is radiolucent. The grid template 200 can include any shape or pattern of geometric nature or text to reference angles, length positioning or targeting. The grid template 200 can be a single line, a geometrical pattern, number, letter or a complex pattern of multiple lines and geometries that correspond to surgical variables. The grid patterns can be predesigned or constructed intraoperatively in real-time based upon the surgeon's knowledge of anatomy and clinical experience including interpretation of morphometric literature and studies identifying key relationships and dimensions between anatomical landmarks and its application in supporting good surgical technique as it relates to specific procedures. With respect to a digital dimensioned grid, this form of the grid template 200 is generated by the application software.

The subject is prepared and positioned for a medical or surgical event in a standard manner as indicated for the specific procedure, for example, joint replacement, orthopedic trauma, deformity correction, sports medicine, and spine. The procedure specific information for the respective application is extracted from the preoperative image 115 or data and mapped into live intraoperative images 120. Mapping is defined as computing a best-fit image transformation from the preoperative to the intraoperative image space. The transformation is made of the composition of a deformation field and an affine or rigid transformation. The best fit transformation is computed using a variety of established methods, including gradient descent on mutual information, cross-correlation, or the identification of corresponding specific anatomical landmarks in preoperative 115 and intraoperative images 120. See, e.g. U.S. Pat. No. 9,610,134 specifically incorporated by reference in its entirety.

Now referring to FIGS. 7A, a new image 120 of the unaffected anatomy is acquired and transmitted (can be wirelessly) to the computing platform 100. At the beginning of the procedure, the user will use the software of the computing platform 100 to assist with anatomical positioning, namely the Image QS and Pose module as shown in FIG. 4A. The computing platform 100 identifies landmarks on the intraoperative image 120 and determine an optimal pose for the image to be taken. Landmarks are identified based on classifiers learned from the medical image datasets. Outcome classifiers can take the form of a deep neural network, a template matching algorithm, or a rule-based classifier or decision tree.

Now referring to FIG. 7B, the is computing platform 100 provides a real-time guide template 250 of good pose estimation. The guide template 250 is a guide for the user to acquire a best-fit opportunity for the artificial intelligence intra-operative surgical guidance system 1 to match subsequent new images 120 with the dataset of optimal-pose-images as shown on an electronic display device 150. For example, in an ankle, once a pose is selected, the lateral image can be segmented into specific anatomical features and a guide template 250 mapped to these features—tibia, fibula, and talus.

FIGS. 8A-C shows the overlay mapping of images and pose guide template 250 to provide a pose-guide image 260. Once the user has acquired the preferred or correct image pose, then that image and/or guide template 250 can be used as the guidance pose-guide image 260 for the remainder of the procedure. The guidance pose-guide image 260 can be that of a contralateral or unaffected side of the body, or a best-fit image from a dataset, or a statistical shape model, or a geometric virtual grid.

The user takes subsequent images until satisfied it matched the guidance pose-guide image 260 required or a threshold is detected. The correct pose can be acquired in two ways, 1) by adjusting position of anatomy (subject), or 2) by adjusting pose/angle of imaging equipment (ex C-arm). This process can be manually instructed by the user or autonomously performed by the software module of the computing platform 100. The computing platform 100 attempts to determine whether the matched image 270 is a good match for one of the images 120 in the preoperative image database. Here the computing platform 100 uses the Image Registration Module 9 as shown in FIG. 3A.

This process involves a multi-scale image-based registration metric that can be quickly applied to the image pairs. If a match above a threshold is detected, the computing platform 100 attempts to automatically identify relevant anatomical landmarks in the new image using any of the techniques for image landmark classifiers. Landmark information and optionally other image information is used to compute a transformation T of the new image to the coordinate space of the preoperative image.

Now referring to FIG. 8B, auto landmarking and smart image registration occur at this time whereby the computing platform 100 attempts to automatically identify relevant anatomical landmarks, such as posterior distal fibula 271, in the matched image 270. Any of the aforementioned techniques for landmark classifiers can be used. In addition, image nail approaches based on edge and feature recognition, landmark identification, statistical atlas registration, and deformable models can be used to segment relevant areas of anatomy from the image, such as the talus 272. In these images, the matched image 270 is a template that acts a pose guide 250 in this situation.

Now referring to FIG. 8C the best image pose guidance good side with image registration module 9 and pose guide module 5 in addition to expert domain knowledge dataset is accessed as shown. Once the best pose image is accepted, the image registration module 9 identifies the application specific feature(s) 280, for example the talus in an ankle fracture procedure. The output is an automatic identification and selection of the desired anatomical features and a grid template 200 positioned relative to these features 280 displaying image and grid alignment.

Now referring to FIGS. 4A and 5, in the image registration module 9, a user such as a surgeon, selects at least one anatomical landmark in the anatomical image on the graphical user interface 151. Anatomical landmark selection can be accomplished by a various methods including but not limited to: auto-segmentation where the software of the computing platform 100 uses feature/pattern recognition process to auto-detect known and targeted anatomical landmarks; use of a remote infrared device, such as a gyro mouse; voice command; air gestures; gaze (surgeon uses gaze and direction of eye or head motion to control targeting) or touching the visualization screen at the selected anatomical landmarks.

In one illustrative embedment, the surgeon inputs the selection of the anatomical landmarks to the workstation manually or using a variety of input devices such as, an infrared wand or an augmented reality device. The application software of the computing platform 100 registers a grid template 200 with the selected anatomical landmarks. The method includes the step of registering an anatomical image to a grid template 200 by selecting at least one anatomical landmark to provide a grid template 200 with at least one grid indicator 280. A grid indicator 280 is an anatomical feature defined and located on an image that correlates with a known position on a virtual grid template 200 for purposes of registration. If needed a registration procedure is used to either unwarp the image or warp the digital grid indicators according to the image warping.

The software of the computing platform 100 identifies and recognizes calibration points that are radiopaque in the image. These are of known dimensioned geometries. A grouping of these points is a distortion calibration array. The distortion calibration array is placed on the image intensifier or in the field of image of any imaging system so that the known distortion calibration array lines/points are identified when an image is taken and captured. These known patterns are saved for use in the distortion adaptation/correction process. The distortion calibration array is removed from visualization on the display medium to not obscure and clutter the image with unnecessary lines/points. A distortion calibration array can be made a series of lines or points that are placed to support the distortion adaptation of the grid template 200. The distortion calibration array points or lines are radiopaque so that the distortion process can calculate the location of these points/lines relative to the anatomy and quantify the amount of distortion during each image taken. Once these points/lines are identified and used in the distortion process, there is another process that removes the visualization of these points/lines from the anatomical image so that they are not obstructing the surgeon's image when he or she sees the grid template 200 and the anatomical image.

In one embodiment, the registration process involves manually or automatically detecting grid landmarks (such as grid line intersections, points, and line segments) on the grid template 200 superimposed on the anatomical image and then aligning those landmarks via an Affine Registration and a deformation field with corresponding landmarks on a distortion calibration array of known geometry, which is a represented digitally. The method includes the step of deforming the calibrated dimensioned grid to correct for the distortion of the anatomical image to generate a deformed calibrated dimensioned grid image. Known radiopaque lines/points (from distortion calibration array) are used to provide a measure of EM distortion in each anatomical image. The distortion is quantified and then the software of the computing platform 100 generated virtual grid is adapted to match the distorted anatomy in each anatomical image.

The distortion calibration array is of non-uniform design, such that the selected anatomical landmarks are clustered more densely in regions of interest to the surgeon, in order that the deformation correction can be estimated with greater precision in those regions. The deformation estimation proceeds as follows: once selected anatomical landmarks have been identified (either manually or automatically) on the array image, an Affine Transformation that produces the best mapping between corresponding selected anatomical landmarks from the grid template 200 to the array image is computed. Following transformation of the grid points by the Affine Transformation, which adjusts the landmarks for translation, rotation, and scaling with respect to the array image landmarks in the Deformation Field (which is the residual difference between transformed grid points and the array image points) is modeled using Thin-Plate Splines or any other suitable radial basis functions. Parameters of the Thin-Plate Splines or radial basis functions are estimated by solving a linear system of equations. U.S. patent application Ser. No. 15/383,975 (hereby specifically incorporated by reference). The array image becomes the reference image or the calibrated image.

Once the deformation field has been computed, the dimensioned grid is adapted in real-time intraoperatively to fit the subject anatomy, thus producing a distorted grid indicator, such as lines curving that can be used to match or fit the musculoskeletal anatomy or the shape of the implant. The deformation of the grid indicators is then applied in real-time by first applying the Affine Transformation and then warping the grid indicators along the Deformation Field. A grid pattern based upon the anatomical points that was defined and targeted in landmark identification is generated. The software of the computing platform 100 is configured to compute the amount of distortion in each image and it quantifies this amount relative to the anatomical image and then displays the calculated grid/Image relationship displaying an image of the subject's anatomy with the quantitatively distorted dimensioned grid image. These deformed grids are tracked in real time with each new image taken. The deformed grid can be positioned relative to anatomy, implant, and fractures auto or manually by the user such as a surgeon. Numerous equations and formulas are used within the algorithms to calculate: measurements, differences, angles, grid and implant positions, fracture deviations to determine at least one measurement of surgical variables involving the implant or trauma.

In auto-segmentation, the at least one anatomical landmark selected by the surgeon is automatically selected for each successive anatomical image. Auto-segmentation allows a surgeon to work more rapidly. Auto-segmentation is accomplished through a combination of one or more of the following techniques: intensity thresholding; feature detection on the intensity edges in the image, including shape detection via the Hough Transform or other methods; feature detection followed by registration of a 2D or 3D anatomical atlas with predefined landmark positions.

Now referring to FIGS. 9A-B and 10, an intraoperative image with anatomical features defined is shown as a graphical user interface. A grid template 200 is mapped to the identified anatomical object or implant feature to form a matched grid map image 290. In this image the object is a lateral talus 280. The computing platform 100 is configured to auto track features and calculate new coordinate positions and integrated grid map of anatomy, objects, and implants.

The graphical user interface is i) locked for auto tracking of subsequent images and, ii) auto integrate and position an alignment grid. Using the graphical user interface, an alignment grid 350 is positioned in the matched image. The user adjustments are accepted and the computing platform 100 is configured to provide a matched grid map 290.

Now referring to FIGS. 11A-B, an image 121 of the affected side is obtained. The affected side could show a deformed, injured or diseased limb. The process previously described for the good side is repeated for the affected side. In this process, the best pose and auto identify anatomical features, objects and implants occurs by matching to the good side of the subject. The inputs to the process are: affected side image, good-side pose guide data and feature identification of the data set. The task conducted by the computing platform 100 is to estimate the best pose match with the good side and auto map the feature and the grid map. The action required is calculate the best pose, auto identify features and calculate the matched grid map. The output is the good side (contralateral) and afforded side are matched with the alignment grid is positioned on the image.

Now referring to FIGS. 12A-B, a fracture identification and reduction module 16 with access to an AO/OTA Classification Dataset interprets the image and makes a classification of the bone, bone section, type and group of the fracture. As shown in FIG. 12A as a graphical user interface, the user then can accept the classification. In an exemplary embodiment, in the event that the procedure involves a fracture of the bone, the affected side image is analyzed for a fracture and the type of fracture classified 45 according to the AO/OTA classification system. For example, an ankle fracture selection classified as metaphyseal complex (43-A3). Next if the classification is accepted, then the task and actions include providing the treatment option 47.

As shown in FIGS. 12 B-C, a treatment option 47 is provided based on the classification selected. Treatment option 47 is shown as a graphical user interface. Here a trauma plate implant 49 is shown for use in this fracture situation. This is accomplished by the computing platform 100 configured to acknowledge the selection of fracture type from the relevant dataset, and algorithmic modules are accessed for a treatment plan analysis and suggestion for the user 155. The treatment option 47 will include a determination of the recommended implants for fixation of this type of fracture classification, for example an implant plate with specific screw configurations and selections 49. Automatic fracture identification can be accomplished using a classifier trained with various machine learning approaches, including deep convolutional neural networks or rule-based classifiers.

More specifically, the CNN model is trained on datasets which include images with one or more fractures and other images without fractures. Then, the CNN model determines whether there is a fracture or not and also localizes the region of interest which contains the identified fracture and/or the abnormality. Precise identification of the fracture area in the image is critical information required to support the classification, in addition to providing evidence regarding the fixation process for the type of fracture. In practice, the input image is processed by a CNN model (representative architecture is illustrated in FIG. 3A, which includes various conventional and max-pooling layers, in order to produce feature maps. At the last layer, the network is modified to target a candidate 'fracture region of interest' on the image based upon feature map information giving the location and size of the region of interest. Candidate regions, including all fracture location and suspected abnormality detections, marked by the CNN model are then shown.

Now referring to FIGS. 13A-B, a guidance pose-guide image 260 can also be used as the good-side reference image to be used throughout the procedure as a template image for the similarity evaluation and mapping module whereby the anatomy of the good, or unaffected, side is matched with the image of the affected side anatomy 121. This is accomplished by the computing platform 100 configured to use image analysis and segmentation techniques to autonomously perform a similarity evaluation to identify and register bony anatomical features, in real-time, of the affected and contralateral images. This technique is identified as ghosting. In ghosting, an overlay image 50 is obtained by overlaying the good-side image 120 versus the bad side image 121 with reference to the guidance pose-guide image 260. Matching of the operative and contralateral-side images is accomplished by computing a best-fit image transformation. The transformation can include the composition of a deformation field and an affine or rigid transformation. The best fit transformation can be computed using a variety of established methods, including gradient descent on mutual information, cross-correlation, or the identification of corresponding specific anatomical landmarks in preoperative and intraoperative images.

More specifically, as shown in FIGS. 5A-5C, the ghosting procedure involves the steps of: 1) Before the surgery, operating room personnel acquires preoperative image(s) of the nonoperative side of the patient's or subject's anatomy. For example, in an ankle fracture case, standard anterior-posterior, lateral, and mortise images of the uninjured ankle would be taken. These images might also be ordered by a surgeon to be acquired by radiology using standard x-ray before the case and then loaded onto our device before the surgery. 2) The nonoperative-side images acquired in step 1 are processed by the computing platform 100 to identify key landmarks that will later be used for image registration with the operative side. Additionally, these images may be corrected for distortion and may have a grid template overlaid. 3) During the reduction phase of the surgery, images of the operative side are acquired that the surgeon uses for reduction of the fractured anatomy. These operative side images are processed to identify key landmarks that will be used for image registration with the nonoperative side. Additionally, these images may be corrected for distortion. 4) The computing platform 100 identifies the best-matching nonoperative side image to the current operative side image using an image similarity metric. The best-matching nonoperative side image is registered to the current operative side image. The registration process computes an image transformation with is made of a transformation matrix (affine or rigid), a deformation grid, or both. 5) The computing platform 100 uses the image transformation to align the non-operative-side image with the current operative-side image and produce an image overlay that illustrates the difference in the anatomical positioning of the non-operative and operative-side images. This overlay image is a guidance pose-guide image 260 that is a template that the surgeon can use to restore the patient's normal anatomy on the operative side (based on the non-operative side anatomical positioning). 6) Any dimensioned grids or other annotations placed on the non-operative side image can be transformed to their corresponding position on the operative-side image to augment the registered composite image.

Now referring to FIG. 14A, a similarity evaluation 52 is performed and the registration match confidence is calculated based in the Image Registration Module 9, which includes one or more image registration algorithms. The similarity evaluation 52 shows similarity evaluation and mapping.

In FIGS. 14B-C, the grid similarity mapping of the confidence percentage is shown in a graphical user interface display by aligning the non-operative-side image with the current operative side. A rendering display of the 'ghosting' or good vs bad mapping/matching/overlay of difference 53 that has been calculated by the computing platform 100. The key color is the red showing the area difference between the two images. Using the highlighted guide, the match measurement 54 are shown to the user to accept or decline the information provided. In the user confirms good-side acceptable for use in for example alignment.

In FIGS. 15A-C, a graphical user interface displays the match measurement 54 for the user to accept or decline the information provided. In an exemplary example, a fibula length match of −5.5 mm is shown. In FIG. 15 B, an example of a graphical user interface display shows an ankle. The good side is over-laid with the grid alignment and measurements. A ghosting interpretation of an ankle 55 is shown. FIG. 15C is an example of a hip graphical user interface demonstrating a ghosting interpretation of a hip 56 on the good side overlay with grid alignment and measurements for a nail example.

In FIG. 16, the output of the Shape Modeling Module 10 is data for intraoperative calculation and guidance based on the 3D to 2D registration (or fitting) of a statistical shape model of the application anatomy to the 2D. A statistical shape model is used to predict the rotation in nailing applications. A statistical shape model is a representation of the variability of anatomy in a population that is encoded as one or more sample mean shapes plus modes of variability. A variety of image processing methods exist whereby a statistical shape model can be fit to images of patient anatomy in order to augment missing information in the medical image. For example, the three-dimensional pose, including rotation, of a two-dimensional fluoroscopic image of an implant such as an intertrochanteric nail can be inferred using a statistical model of implant nail geometries. The pose inference is computed by a simultaneous fitting of the statistical model to the two-dimensional image and an iterative registration of the two-dimensional image with simulated projects of the statistical model of the anatomy.

Now referring to FIGS. 17A-B for example, the computing platform 100 identifies a varus reduction 60 of the femoral head during a procedure and provides the user with a varus reduction warning 61 indicating a high risk of failure based upon the calculations of the weighted intelligence model. A grid template of an optimal reduction can be provided to provide guidance and assist the user in obtaining a satisfactory outcome.

The computing platform 100 is configured to analyze and interpret the information and provide guidance based upon a correlation to a known set of patterns and inference from datasets as set out in FIGS. 4A & 4B. The outputs related to surgical guidance include implant selection recommendations, implant placement, performance predictions, probability of good outcomes, and failure risk scores. The structure of the deep learning platform demonstrating the different layers is indicative of the configuration of the flow of information and how the information is applied. The data layer is made of a collection of data from various networks. In a trauma event, such as fracture reduction or deformity correction, or in an arthroplasty event such as hip or knee anatomical alignment or bone cut guidance, or in the event of a spine procedure with implant alignment correction, or in a sports medicine event with ACL reconstruction alignment, these surgical and procedure specific datasets coupled with domain knowledge and information from subject health records that are critical to an event can be accessed. The data set are used to interpret critical failure mode factors of an implant or anatomical alignment and combined will provide the user with a Failure Risk Score with the output to the user as a confidence percentage recommendation of a suboptimal or optimal performance metric. The output is presented to the user in the form of intelligent predictors and scores to support decisions encountered in a real time event.

The is computing platform 100 analyzes an image for risk factors that the user cannot see due to their human inability to interpret an overwhelming amount of information at any specific moment. If the implant placement and the alignment does not match this data pattern, it will create an awareness in this specific situation and provide a hazard alert to the user. Essentially, identifying and predicting problems ahead of the user encountering them. This can lead to avoidance of complications and prevention of errors. The surgical guidance is related to: deformity correction, an anatomy alignment, a fracture reduction and an anatomy reduction. The process of surgical guidance will be discussed in the following section for these applications. The following sections show how the computing platform 100 interprets the information and provides guidance based upon a correlation to a known set of patterns and inference from data sets as applied to different surgical procedures.

TRAUMA EXAMPLE—HIP FRACTURE. The most frequent fractures hospitalized in US hospitals in 2015 were for those of the hip, according to data from the HCUP (Healthcare Cost and Utilization Project of the Agency for Healthcare Research and Quality (AHRQ)). There are known reasons for the failure modes of these procedures. For example, it is documented that determining and utilizing the correct entry point for nailing of a bone can prevent malreduction of the fracture and ultimately failure of the implant or the compromising of an optimal outcome.

Subject anatomy is unique and using a single-entry point for all subjects is not desirable. Once the subject has been prepared for surgery in a standard manner, the artificial intelligence intra-operative surgical guidance system 1 is turned on and the platform is now activated. A new image of the subject's anatomy is taken. The image is of the contralateral unaffected, or good, side of the subject. The platform is instructed, or will determine, if the information it receives is 3D or 2D. If the information is 3D, then the artificial intelligence intra-operative surgical guidance system 1 will call the relevant module to perform a 2D to 3D registration or utilize the 3D model for statistical inference. If the image is 2D, the artificial intelligence intra-operative surgical guidance system 1 will capture the image and an initial grid pose module will analyze the image and determine if the pose of the image is adequate for use as a 'true' image. A true image is a datum or base image that will be utilized throughout the procedure as a good anatomical reference image that the software algorithm is able to reproducibly recognize. With each new image acquired during this step of the procedure, the algorithm will access a dataset of annotated good anatomy pose images and provide a virtual grid pose template to guide the user to establish the correct pose. An example of the grid pose in this situation would be to advise the user to 'internally rotate the hips 15 degrees in the AP image with the beam centered at the teardrop'. Once the correct image is accepted, the computing platform 100 accessed the automated image segmentation algorithm to identify the relevant anatomical features. In this specific application (FIG. 18A), the anatomical features to be identified can include the tip of the greater trochanter (GT) 70, femoral shaft axis identified by center of canal 71, and the femoral neck axis identified by center of femoral head and center of neck 71. The neck-shaft angle 71 is measured as the medial arc between the shaft and neck axes. The affected side image is now taken with a similar matching image pose. The feature recognition and segmentation algorithm are accessed as well. The image registration module 9 is accessed here and a good-side match model is calculated. A good vs bad grid map similarity evaluation provides the user with a match confidence percentage. This step involves: mapping a grid template to the anatomical structure to register an image for the nonoperative side of the subject's anatomy with an image of the intraoperative image of the operative side of the subject's anatomy to provide a registered composite image. The registered composite image is provided to the artificial intelligence engine to generate an at least one graphical surgical guidance In this step, the implant dataset is accessed. The dataset includes information on the three-dimensional geometry of the implant options. The machine learning algorithm associated with this dataset analyzes, measures, and calculates the relevant variables and has the capability to identify suboptimal outputs and provide the user with situational awareness and hazard alerts leading to complication avoidance and error prevention. The output is presented to the user as surgical guidance, such as an optimal or sub-optimal risk score for failure if the user proceeds with the pathway along which he intends follow.

The computing platform 100 predicts performance based upon these pathways and can also provide the user with a probability of an optimal or sub-optimal outcome. The computing platform 100 provides the user with an implant recommendation based upon the known predictors of a successful outcome. The computing platform 100 dynamically updates the registered composite image with the at least one graphical surgical guidance as the surgeon changes interoperative variables. The surgical variable depends upon the ongoing surgery and includes the position of the patient, the pose estimation, the implant position or the nail entry point in a femur fracture surgical procedure.

Now referring to FIGS. 1A, 4A &. 18B, the correct nail entry-site prediction information is now accessed within the known indicators and predictors of complications dataset. The dataset uses information from industry gold-standard or historical peer-literature reviewed studies to perform analytical calculations and determine optimal and suboptimal performance predictions. In addition, the computing platform 100 determines if there is a probability of an error occurring by a specific placement of an entry-site or orientation of a guidewire or reamer 75. The optimal entry point prediction utilizes a combination of the various algorithmic modules for information.

In this application, the relevant landmarks are identified using the segmentation machine learning algorithm, the implant dataset is used for subject best entry-point grid templating, the nail grid template is optimally auto-placed on the image using the deep learning algorithm with access to the known-literature and study dataset, the distances between the various features are measured and the output values will predict an outcome using the literature and study dataset with known optimal versus suboptimal risk values.

Now referring to FIG. 18C, for example, the user can want to use an entry-point at the GT (Greater Trochanter of Femur) tip 70, but the implant design and subject's anatomy predicts this pathway will likely result in a valgus malreduction. Once an optimal entry point is quantified 76, it is displayed on all subsequent images acquired. The entry point is dynamically tracked image to image by the anatomical and implant segmentation tracking module. The updated entry point is calculated relative to the known and selected anatomical feature tracking points.

Now referring to FIG. 18D, a new image is acquired and the guidewire 77 or starter reamer is recognized on the image. An ideal system predicted entry point is recommended and displayed 76, and if the user accepts these suggestions, the user then places and orientates the guidewire or reamer in the positions guided by the accepted and displayed virtual or augmented grid or avatar 78. The user completes this step of the procedure with imaging or CAS (traditional Computer Assisted Surgery system) tracking and intelligence guidance from the systems' algorithmic modules.

Now referring to FIG. 19A, this step is defined by the lag-screw placement. The lag-screw module will calculate and provide guidance on the depth, and rotation, of nail placement 80. Once the nail is begun to be inserted, the lag-screw placement 81 will be used as the determinant of the depth the nail needs to be seated in the bone. When an image is acquired, the artificial intelligence intra-operative surgical guidance system 1 uses the hip application segmentation machine learning module to identify the relevant anatomical, instrument, and implant features such as the nail alignment jig, and nail and lag-screw.

In addition, the artificial intelligence intra-operative surgical guidance system 1 provides an automatic determination of screw trajectories and more generally in situations of instrumentation trajectories. For example, to determine if the instrumentation is within the right plane while simultaneously tracking anatomical, implant and instrument considerations in different views. This is achieved using deep learning techniques, more specifically, a Reinforcement Learning (RL) technique. RL strategies are used to train an artificial RL agent to precisely and robustly identify/localize the optimal trajectory/path by navigating in an environment, in our case the acquired fluoroscopic images. The agent makes decisions upon which direction it has to proceed towards an optimal path. By using such a decision-making process, the RL agent learns how to reach the final optimal trajectory. An RL agent learns by interacting with an environment E. At every state (S), the region of interest in this situation, a single decision is made to choose an action (A), which consists of modifying the coordinates of the trajectory, from a set of multiple discrete actions (A). Each valid action choice results in an associated scalar reward, defining the reward signal (R). The agent attempts to learn a policy to maximize both immediate and subsequent future rewards. The reward encourages the agent to move towards the best trajectory while still being learnable. With these considerations, we define the reward R=sgn(ED(Pi−1, Pt)−D(Pi, Pt)), where D is a function taking the Euclidean distance between plane parameters. Pi (Px, Py, Pz) is the current predicted trajectory coordinate at step 1 and Pt is the target ground truth coordinates. The difference of the parameter distances, between the previous and current steps, signifies whether the agent is moving closer to or further away from the desired plane parameters. Finally, the terminate state is reached once the RL agent reaches the target plane coordinates. The task is to learn an optimal policy that maximizes the intermediate rewards but also to subsequent future rewards.

Now referring to FIG. 19B, the nail is tracked in real-time using sensors or images and is guided to the correct depth and the lag-screw configuration and placement information is provided as an input for interpretation. The location of the lag-screw in the specific anatomy 82 is analyzed to statistically determine its probability of cutting out of the femoral head 83.

Now referring to FIG. 20A, the failure mode and a risk score is calculated and can be displayed to a user. Based upon the calculations, the artificial intelligence intra-operative surgical guidance system 1 predicts an optimal position of the implant and provide guidance for placement 85. In the event of a malrotation situation in a nailing procedure, predictive support and guidance can be quantified for optimal rotational correction and implant placement 86.

Now referring to FIG. 20B, in the event of a fracture or deformity correction situation that requires plating and screw fixation, the use of multivariate relationship datasets can provide the user with impaired healing predictions 90 such as in the case of which plate to use. Or alternatively a screw combination calculation can provide the user with a prediction 91 of a consistent result if a specific guidance is followed. This can provide a predictive output of a normal healing or abnormal healing expectation 92.

Now referring to FIG. 21, the real-time situational guidance workflow of a plate and screw application is depicted displaying the inputs, tasks and actions performed, and the outputs with a graphical user interface display. As the user/subject navigates through the procedure, the artificial intelligence intra-operative surgical guidance system 1 provides awareness support to situations encountered and provides performance and complication avoidance recommendations at critical points in the workflow 500. Specific decision points in the workflow can be, for example, the screw order and placement position in the plate implant 501. This can provide surgical guidance to the user/subject, for example, for tracking to a drill guide 502.

Example—ankle injury. Now referring to FIG. 22, a problem prediction and error prevention workflow is depicted for an ankle procedure. Now referring to FIG. 3, the information from independent datasets can be accessed at any given time, or alternatively a situation during the event can require the input from various datasets simultaneously. In this situation information from the relevant datasets are selected for inclusion in the weighted multivariate relationship data model. This model utilizes information from datasets that have a relationship from the perspective of sharing predictors for example of a specific outcome. The model further weights the data based upon the level of criticality regarding performance or failure for example. The model outputs decision support and outcome predictions for example the probability of a successful and optimal long-term outcome. In the event of a fracture or syndesmosis or fibula minus situation 600 that requires fixation 601, the use of multivariate relationship datasets and outcomes prediction modules can provide the user with impaired healing predictions 602 such as in the case of which implant to use. Or alternatively an implant combination calculation can provide the user with a prediction of a consistent result if a specific guidance is followed. This can provide a predictive output of an optimal implant position or normal healing/abnormal healing expectation and probability of success 603.

Example—Hip Arthroplasty. Now referring to FIG. 23, in the event of a hip replacement situation 610 that requires implant fixation 611, the use of multivariate relationship datasets and outcomes prediction modules can provide the user with impaired healing predictions 612 such as in the case of which implant to use. Or alternatively an implant orientation calculation can provide the user with a prediction of a consistent result if a specific guidance is followed. This can provide a predictive output of an optimal implant position or normal healing/abnormal healing expectation and probability of success 613.

Example—Knee Arthroplasty. Now referring to FIG. 24, in the event of a knee replacement situation 620 that requires implant fixation 621, the use of multivariate relationship datasets, sensor information, multi-modality medical images, and outcomes prediction modules can provide the user with hazard and failure predictions 622 such as in the case of what resection or balancing needs to be performed. Or alternatively an implant alignment calculation can provide the user with a prediction of a consistent result if a specific guidance is followed. This can provide a predictive output of an optimal implant position or normal healing/abnormal healing expectation and probability of success 623.

Example—Spine. Now referring to FIG. 25 in the event of a spine situation 630 that requires fixation 631, the use of multivariate relationship datasets and outcomes prediction modules can provide the user with impaired healing predictions 632 such as in the case of which implant to use. Or alternatively an implant placement calculation can provide the user with a prediction of a consistent result if a specific guidance is followed. This can provide a predictive output of an optimal implant position or normal healing/abnormal healing expectation and probability of success 633.

Example—Sports Medicine. Now referring to FIG. 26A in the event of a sports medicine situation 640 that requires alignment or fixation guidance 641, the use of multivariate relationship datasets and outcomes prediction modules can provide the user with impaired healing predictions 642 such as in the case of which implant to use. Or alternatively an implant placement calculation or soft tissue management can provide the user with a prediction of a consistent result if a specific guidance is followed. This can provide a predictive output of an optimal implant position or normal healing/abnormal healing expectation and probability of success 643.

Now referring to FIG. 26B in the event of a PAO/FAI situation 655 that requires alignment and fixation 656, the use of multivariate relationship datasets and outcomes prediction modules can provide the user with impaired healing predictions 657 such as in the case of which implant to use. Multivariate relationship datasets is defined as analysis performed using interaction between different fields and different datasets. Or alternatively an implant placement calculation can provide the user with a prediction of a consistent result if a specific guidance is followed. This can provide guidance for a robot or a predictive output of an optimal implant position or normal healing/abnormal healing expectation and probability of success 658.

Now referring to FIG. 27, the generic workflow of an outcome prediction demonstrates the predictive probability method in calculating the likelihood of a successful long-term outcome. Datasets configured to include information that will potentially have an impact on the outcome of the procedure are accessed. The datasets are used to interpret critical failure mode factors of an implant or anatomical alignment and when used to train an outcomes classifier for an Artificial Intelligence Engine will provide the user with a prediction of optimal or suboptimal outcome and an associated Failure Risk Score. Multiple classifiers can be constructed from multiple datasets and used in a single AI Engine.

Information from the relevant datasets are selected for inclusion in the Artificial Intelligence (AI) Engine in the form of multiple trained classifiers, each with a weighted contribution to the final surgical outcome prediction. This multiple prediction model uses information from datasets that have a relationship from the perspective of sharing uncorrelated or partially correlated predictors of a specific outcome. The AI Engine can further weight the outcome prediction data based upon the relative level of criticality regarding performance or failure. The model outputs decision support and outcome predictions for example the probability of a successful and optimal long-term outcome 665.

Now referring to FIG. 28A, the factors affecting the output of a nailing application demonstrates the calculation of the likelihood of a non-union of the bone post procedure. Now referring to FIG. 28B, the weighted model provides an at least one graphical surgical guidance through a graphical user interface output demonstrating the prediction of an optimal versus sub-optimal outcome. The weighting factors 96 can be demonstrated to the user in addition to an implant and outcome performance percentage metric 97 predicting ultimately the probability of a good outcome. Now referring to FIG. 28C, the workflow demonstrating the iterative decision making and support process by the artificial intelligence intra-operative surgical guidance system 1 and AI model interfacing with the user. The images or information can be compiled and saved to a user system or device of choice, such as a PAC's system, Cloud or RAM.

Now referring to FIG. 29, the information or images can be saved for subject demonstration post-procedure as a graphical user interface. The artificial intelligence intra-operative surgical guidance system 1 is configured to support a tool that will utilize AI to automate the detection, tracking, monitoring and performance/complication prediction for user's post-procedure.

Now referring to FIG. 30, the data from the procedure can be used for implant performance, tracking, outcome knowledge, outcome knowledge, inventory optimization, Quality Assurance, and design optimization, the data from the procedure can be saved for outcomes analysis and scoring after an event such as surgery for the following: 1) user performance and usage information, 2) tracking and monitoring performance and outcome metrics—for example IoT monitoring of alignment and reduction, and implant fixation and the prediction of a roadmap to a successful outcome, and 3) subject, event or situation predictors, indicators, factors, and variables. Surgical guidance such as measurements and data can also be sent to: a surgical facilitator 160 such as a feedback device, a robot, a tracked Implant or object, a cutting block, a CAS and a IoT device Measurements and data can also be sent to a touch/force sensor to a mixed/augmented/holographic reality device 167 showing visualization, alignment, and placement of instruments, bones or implants in 2D/3D .mixed/augmented/ holographic reality image/shape model with the dimensioned grid in a surgical environment in real-time intraoperatively by projecting mixed/augmented reality grid data and image measurements for live dynamic mixed/ augmented reality tracking of the dimensioned grid, surgical instruments and implant.

Now referring to FIG. 31 a grid data predictive map 301 is shown. The computing platform 100 identifies a best-matching nonoperative side image as compared to a current operative-side image using an image similarity metric; registering the best-matching non-operative side image to the current operative side image; and aligning the non-operative-side image with the current operative side image to provide a guidance pose-guide image, wherein the guidance pose-guide image graphically illustrates the difference in the anatomical positioning of the non-operative and operative-side images as shown. A grid data predictive map 301 is a grid of points of interest in the image i.e., the coordinates position of landmarks.

The grid data predictive map 301 is an overlay image wherein the red-green-blue pixel values of the overlay are computed using a color map that maps surgical outcome classification values to color hues. A first color for sub-optimal positioning and second color for optimal positioning is provided. The classifications, in this case, are in reference to locations in the grid data predictive map 301 that are associated with optimal or suboptimal positioning of implants 302, instrumentation, or bone positioning in fracture reduction. In such an overlay, for example, the color mapping may be a "heat map" where suboptimal positioning regions on the grid map are indicated in red and optimal positioning regions indicated with green. Such a grid data predictive map 301 can be used for example, to guide optimal position of a nail entry point. Other examples may include screw trajectories 303 and implant positioning.

In practice a grid map of pixels/voxels contributes to predictive class by providing real-time situation awareness/ decision support and generating a Risk Factor Score and predicts outcomes. A method for providing surgical guidance to a user is provided including the steps of: receiving an intra-operative image of a subject; generating a grid data predictive map; wherein the grid data predictive map is generated by an artificial intelligence engine made of: computer algorithms and data structures for storage and retrieval of post-operative medical images and associated metadata; aligning the intra-operative image with the grid data predictive map to generate a graphical surgical guidance indicator. The graphical surgical guidance indicator is dynamic in that as the intraoperative images change to reflect changes in positioning the color of the guidance indicator changes. In one exemplary embodiment, grid data predictive map is made of a first color for sub-optimal positioning and second color for optimal positioning.

The foregoing detailed description has been presented for purposes of illustration and description. It is not intended to be exhaustive or to limit the invention to the precise form disclosed. Many modifications and variations are possible considering the above teachings. The described embodiments were chosen to best explain the principles involved and their practical applications, to thereby enable others skilled in the art to best utilize the various embodiments and with various modifications as are suited to the use contemplated. It is intended that the scope of the invention be defined by the claims appended hereto.

We claim:

1. An artificial intelligence based intra-operative surgical guidance system configured to provide intra-operative surgical decision risks comprising:
 a non-transitory computer-readable storage medium encoded with computer-readable instructions which form a software module and a processor to process the instructions, wherein the software module is comprised of a data layer, an algorithm layer and an application layer, wherein the artificial intelligence based intra-operative surgical guidance system is trained to calculate intra-operative surgical decision risks by applying an at least one classifier algorithm, wherein the algorithm layer is comprised of an at least one image processing algorithm for the classification of a plurality of intra-operative fluoroscopic medical images, wherein the computing platform is comprised-of an at least one of: an at least one image processing algorithm for the classification of a plurality of intra-operative medical fluoroscopic images of a reduction or an alignment procedure into at least one discrete category, and an at least one image processing algorithm for the classification of a plurality of an intra-operative medical fluoroscopic images of an implant fixation procedure into an at least one discrete category; and a visual display configured to show a surgical outcome prediction based on calculated intra-operative surgical decision risks to a user, wherein the algorithm layer comprises:

an Image Quality Scoring Module configured to compute an image quality score for a plurality of acquired fluoroscopic medical images;

a Distortion Correction Module configured to correct distortion in the acquired fluoroscopic medical image;

an Image Annotation Module configured to annotate an at least one anatomical landmark in a pre-operative fluoroscopic image to provide an at least one annotated pre-operative fluoroscopic image;

a preoperative image database configured to store the at least one annotated pre-operative fluoroscopic image;

a 3D Shape Modeling Module configured to estimate a three-dimensional shape of an implant or an anatomy;

an Artificial Intelligence Engine comprised of an image processing algorithm for the classification of an intra-operative fluoroscopic medical image;

an Image Registration Module configured to map an alignment grid to the annotated image features to form a composite fluoroscopic image and an outcome module configured to intra-operatively provide a surgical outcome prediction to a user.

2. The artificial intelligence based intra-operative surgical guidance system of claim 1 wherein the image quality score is computed based on one or more automated artificial intelligence models quantifying a level of accuracy of an acquired fluoroscopic image.

3. The artificial intelligence based intra-operative surgical guidance system of claim 2 wherein the algorithm layer is comprised of an at least one algorithm for registering fluoroscopic images of a preoperative nonoperative side and fluoroscopic images of an intra-operative operative side to a common coordinate system.

4. The artificial intelligence based intra-operative surgical guidance system of claim 1, further comprising an outcome classifier for an artificial intelligence engine trained by a deep learning model on at least one dataset used to interpret a plurality of critical failure mode factors of an implant or an anatomical alignment.

5. The artificial intelligence based intra-operative surgical guidance system of claim 1 further comprising an outcome classifier for an artificial intelligence engine trained by a reinforcement learning model on datasets to interpret critical failure mode factors of an implant.

6. The artificial intelligence based intra-operative surgical guidance system of claim 1 further comprising an outcome classifier for an artificial intelligence engine trained by a reinforcement learning model on datasets to determine screw trajectories.

7. The artificial intelligence based intra-operative surgical guidance system of claim 1 further comprising an outcome classifier for an artificial intelligence engine trained by a reinforcement learning model on datasets to interpret critical failure mode factors of screw placement.

8. An artificial intelligence based intra-operative surgical guidance system comprising: a computing platform comprised of an at least one image processing algorithm for the classification of a plurality of intra-operative fluoroscopic medical images, said computing platform configured to execute one or more automated artificial intelligence models wherein the one or more automated artificial intelligence models comprises a neural network model providing a score for the classification for surgical outcomes, wherein the one or more automated artificial intelligence models are trained on data from a data layer, wherein the data layer includes at least a plurality of fluoroscopic surgical images, wherein the automated artificial intelligence models are trained to calculate intra-operative surgical decision risks and a visual display configured to show a surgical outcome prediction based on calculated intra-operative surgical decision risks to a user wherein the computing platform is configured to derive the surgical outcome prediction from a prediction information dataset and a prediction of known complications dataset on the data layer; wherein the algorithm layer includes a segmentation machine learning algorithm that identifies anatomical landmarks on the intra-operative fluoroscopic image;

wherein the segmentation machine algorithm utilizes information from an implant database;

wherein an algorithm on the algorithm layer registers a subject best entry-point grid template on the intra-operative fluoroscopic image;

and wherein the computing platform is configured provide on the visual display the subject best entry-point grid template for a nail-entry site and further includes an at least one performance prediction of nail-entry site.

9. The artificial intelligence based intra-operative surgical guidance system of claim 8 wherein a deep learning algorithm on the algorithm layer registers the subject best entry-point grid template on the intra-operative fluoroscopic image.

10. The artificial intelligence based intra-operative surgical guidance system of claim 8 the computing platform is configured to synchronize with a surgical facilitator.

11. The artificial intelligence based intra-operative surgical guidance system of claim 10 wherein the surgical facilitator is a sensor for providing input data to the data layer of the computing platform.

12. The artificial intelligence based intra-operative surgical guidance system of claim 10 wherein the computing platform configured to synchronize with a surgical facilitator is configured to communicate at least one of a surgical guidance directive to the surgical facilitator.

13. The artificial intelligence based intra-operative surgical guidance system of claim 5 further comprising a preoperative image database.

* * * * *